US007825267B2

(12) United States Patent
Koide et al.

(10) Patent No.: US 7,825,267 B2
(45) Date of Patent: Nov. 2, 2010

(54) SYNTHESIS OF FR901464 AND ANALOGS WITH ANTITUMOR ACTIVITY

(75) Inventors: Kazunori Koide, Pittsburgh, PA (US); Brian J. Albert, Pittsburgh, PA (US); Ananthapadmanabhan Sivaramakrishnan, Jamestown, NC (US)

(73) Assignee: University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 411 days.

(21) Appl. No.: 11/852,278

(22) Filed: Sep. 8, 2007

(65) Prior Publication Data

US 2008/0096879 A1 Apr. 24, 2008

Related U.S. Application Data

(60) Provisional application No. 60/843,230, filed on Sep. 8, 2006, provisional application No. 60/952,326, filed on Jul. 27, 2007.

(51) Int. Cl.
*C07D 315/00* (2006.01)
(52) U.S. Cl. .................. 549/415; 549/419; 514/456
(58) Field of Classification Search ................. 549/415, 549/419; 514/456
See application file for complete search history.

(56) References Cited

U.S. PATENT DOCUMENTS

| | | | |
|---|---|---|---|
| 5,010,176 | A | 4/1991 | Barton |
| 5,156,840 | A | 10/1992 | Goers et al. |
| 5,272,253 | A | 12/1993 | Koppel et al. |
| 5,514,794 | A | 5/1996 | Barton |
| 5,607,915 | A | 3/1997 | Patton |
| 5,643,573 | A | 7/1997 | Barton et al. |
| 5,665,358 | A | 9/1997 | Barton et al. |
| 5,795,560 | A | 8/1998 | Reed |
| 2005/0276812 | A1 | 12/2005 | Ebens, Jr. et al. |

OTHER PUBLICATIONS

Charlotte F. McDonagh et al., "Engineered antibody-drug conjugates with defined sites and stoichiometries of drug attachment", Protein Engineering Design & Selection, vol. 19, No. 7, pp. 299-307, 2006.
Christopher F. Thompson et al., "Total Synthesis of FR901464. Convergent Assembly of Chiral Components Prepared by Asymmetric Catalysis", J. Am. Chem. Soc. 2000, 122, 10482-10483.
Ari M.P. Koskinen et al., "A new Access to Enantiomerically Pure Deoxy Aminohexoses: Methyl 4-Amino-4,6-Dideoxygulopyranoside and *epi*-Tolyposamine", Tetrahedron. vol. 53, No. 18, pp. 6473-6484, 1997.
Leo A. Paquette et al., "A Convenient Method for Removing All Highly-Colored Byproducts Generated during Olefin Metathesis Reactions", Organic Letters, vol. 2, No. 9, 2000, pp. 1259-1261.

Shatrughan P. Shahi et al., "A Mild Mehtod for the preparation of γ-Hydroxy-α,β-Acetylenic Esters", Angew. Chem. Int. Ed. 2004, 43, 2525-2527.
Christopher T. Meta et al., "Trans-Selective Conversions of γ-Hydroxy-α,β-Alkynoic Esters to γ-Hydroxy-α,β-Alenoic Esters", Organic Letters, vol. 6, No. 11, 1785-1787, 2004.
Hidenori Nakajima et al., "New Antitumor Substances, FR901463, FR901464 and FR901465", The Journal of Antibiotics, vol. 50, No. 1, Jan. 1997, pp. 96-99.
Christopher F. Thompson et al., "FR901494: Total Synthesis, Proof of Structure, and Evaluation of Synthetic Analogues", J. Am. Chem. Soc. 2001, 123, 9974-9983.
Richard C. Larock et al.., "Mercury in Organic Chemistry. 24.[1]-Mercuration and Subsequent Carbonylation of 4-Hydroxy-2-alkyn-1-ones: A Novel Route to Furans", J. Org. Chem. 1983, 48, 2151-2158.
Roderick W. Bates et al., "Assessment of Butene-1,4-Diols As Starting Materials for the Preparation of π-Allyltricarbonyliron Complexes", Tetrahedron vol. 46, No. 11, pp. 4063-4082, 1990.
Yutaka Nakamura et al., "Dehydrooligopeptides. XVII. Practical Synthesis of All of the Diastereomers of *N,N*-Protected 2,3-Diaminobutanoic Acids from L- and D-Threonine Derivatives", Bull. Chem. Soc. Jpn. 68, 1369-1377 (1995).
Kenneth A. Giuliano et al., "High-Content Screening: A New Approach to Easing Key Bottlenecks in the Drug Discovery Process", Journal of Biomolecular Screening, vol. 2, No. 4, 1997, pp. 249-259.
D. Lansing Taylor et al., "Real-time molecular and cellular analysis: the new frontier of drug discovery", Current Opinion in Biotechnology, 2001, 12:75-81.
Peter Wipf et al., "Cellular Analysis of Disorazole $C_1$ and Structure-Activity Relationship of Analogs of the Natural Product", Chem Biol Drug Des 2006; 67:66-73.
Daisuke Kaida et al., "Spliceostatin A targets SF3b and inhibits both splicing and nuclear retention of pre-mRNA" , Nature Chemical Biology, vol. 3, No. 9, Sep. 2007, pp. 576-583.
Zhiyong Wang et al., "Structure-activity and High-content Imaging Analyses of Novel Tubulysins", Chem Biol Drug Des 2007; 70: 75-86.
Robert H.F. Peterson et al., "Alteration of Plasma Membrane Glycopeptides and Gangliosides of Chinese Hamster Cells Accompanying Development of Resistance to Daunorubicin and Vincristine", Cancer Research, 43, Jan. 1983, 222-228.
Andreas Vogt et al., "A Scalable High-Content Cytotoxicity Assay Insensitive to Changes in Mitochondrial Metabolic Activity", Oncology Research, vol. 14, No. 6, 2004,pp. 305-314.
Kathleen W. Scotto et al., "Amplification and Expression of Genes Associated with Multidrug Resistance in Mammalian Cells", Science vol. 232, May 1986, pp. 751-755.

(Continued)

*Primary Examiner*—Janet L. Andres
*Assistant Examiner*—Raymond Covington
(74) *Attorney, Agent, or Firm*—Stephen A. Bent; Foley & Lardner LLP

(57) ABSTRACT

The present invention provides novel analogs of FR901464, as well as an improved methodology for preparing FR901464 and its analogs. These compounds display an anti-cancer activity and are candidates for therapies against a number of disease states associated with dysfunctional RNA splicing.

33 Claims, 5 Drawing Sheets

OTHER PUBLICATIONS

Leonard C. Erickson et al., "DNA crosslinking and cytotoxicity in normal and transformed human cells treated with antitumor nitrosoureas", Proc. Natl. Acad. Sci. USA, vol. 77. No. 1, pp. 467-471, Jan. 1980.

Lata Dusre et al., "DNA Damage, Cytotoxicity and Free Radical Formation by Mitomycin C in Human Cells", Chem. Biol. Interactions, 71, (1989) 63-78.

Tian-Jye Hsieh et al., "Liriodenine inhibits the proliferation of human hepatoma cell lines by blocking cell cycle progression and nitric oxide-mediated activation of p53 expression", Food and Chemical Toxicology 43 (2005) 1117-1126.

Hiroki Suzuki et al., "Epidermal Growth Factor Receptor Tyrosine Kinase Inhibition Augments a Murine Model of Pulmonary Fibrosis", Cancer Research 63m 5054-5059, Aug. 2003.

W.W. Nichols et al., "Characterization of a New Human Diploid Cell Strain, IMR-90", Science, vol. 196, Apr. 1977, pp. 60-63.

Masato Horigome et al., "A synthesis of FR901464", Tetrahedron Letters 42 (2001) 8207-8210.

SYNTHESIS OF FR901464 AND ANALOGS WITH ANTITUMOR ACTIVITY

STATEMENT OF GOVERNMENT FUNDING

This invention was made with government support under Grant/Contract No. CA120792-01 awarded by the National Institute of Health. The government has certain rights in this invention.

BACKGROUND OF THE INVENTION

The natural product FR901464, isolated from the broth of a *Pseudomonas* sp. No. 2663 culture, is a transcriptional activator. It lowers the mRNA levels of p53, p21, c-myc, and E2F-1 in MCF-7 cells at 20 nM, and it induces apparent apoptosis in MCF-7 cells with the impressive LC50 of 0.5 nM. FR901464 also exhibits an antitumor activity in a mouse model at remarkably low concentrations (0.056-0.18 mg/kg).

This pharmacological profile for FR901464 has drawn considerable interest, focusing on its potential as an anticancer agent. A 1-desoxy-FR901464 analog, depicted below, has been prepared and found to have a high activity, relative to the natural product.

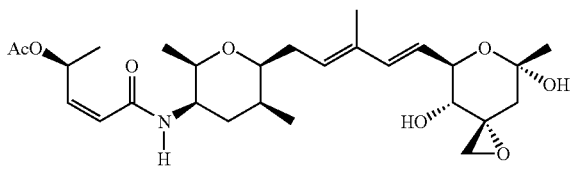

FR901464

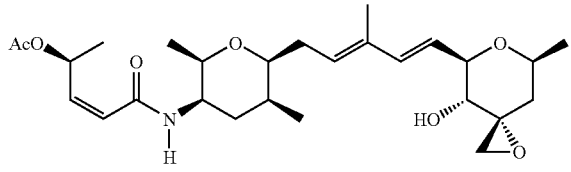

1-desoxy-FR901464

The preparation of more potent analogs has been limited by a lengthy synthesis, involving at least nineteen linear steps and typically forty or more in toto. Accordingly, the present invention provides novel analogs of FR901464, as well as new and improved methods for preparing FR901464 and its analogs.

SUMMARY OF THE INVENTION

The present invention relates to compounds and pharmaceutical compositions containing them, to their preparation, to intermediates useful in their preparation, and to uses for the compounds, primarily but not exclusively in treating cancer. According to one aspect of the invention, a compound, stereoisomer, or pharmaceutically acceptable salt or ester thereof is provided that conforms to Formula I:

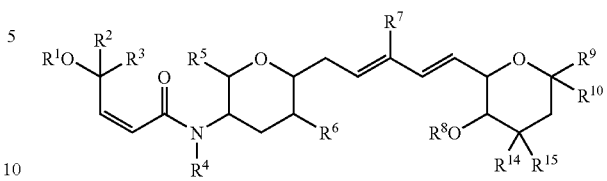

where $R^1$ and $R^8$ are independently selected from the group consisting of H, $C_{1-6}$-alkyl, halo($C_{1-6}$-alkyl), $C(O)R^{11}$, $C(O)OR^{11}$, and $C(O)NR^{12}R^{13}$, wherein each $R^{11}$ is independently H, $C_{1-6}$-alkyl or halo($C_{1-6}$-alkyl), and wherein $R^{12}$ and $R^{13}$ are selected independently from the group consisting of H, $C_{1-6}$-alkyl, and halo($C_{1-6}$-alkyl);

or $R^{12}$ and $R^{13}$, together with the nitrogen atom to which they are bound, form a 5- to 6-membered heterocyclic or heteroaromatic ring;

$R^2$, $R^3$, $R^4$, $R^5$, and $R^6$ are independently selected from the group consisting of H, $C_{1-6}$-alkyl, and halo($C_{1-6}$-alkyl);

$R^7$ is selected from the group consisting of $C_{1-6}$-alkyl and halo($C_{1-6}$-alkyl); and $R^9$ and $R^{10}$ are independently selected from the group consisting of H, $C_{1-6}$-alkyl, and $C_{1-6}$-alkyl substituted with one to three groups independently selected from halo, hydroxy, and $C_{1-6}$-alkoxy, with the qualification that, when $R^1$ is $C(O)CH_3$, $R^2$, $R^4$, and $R^8$ are hydrogen, and $R^3$, $R^5$, $R^6$, $R^7$, and $R^9$ are methyl, then $R^{10}$ is not hydrogen or OH.

DETAILED DESCRIPTION

Definitions

Figure 1:
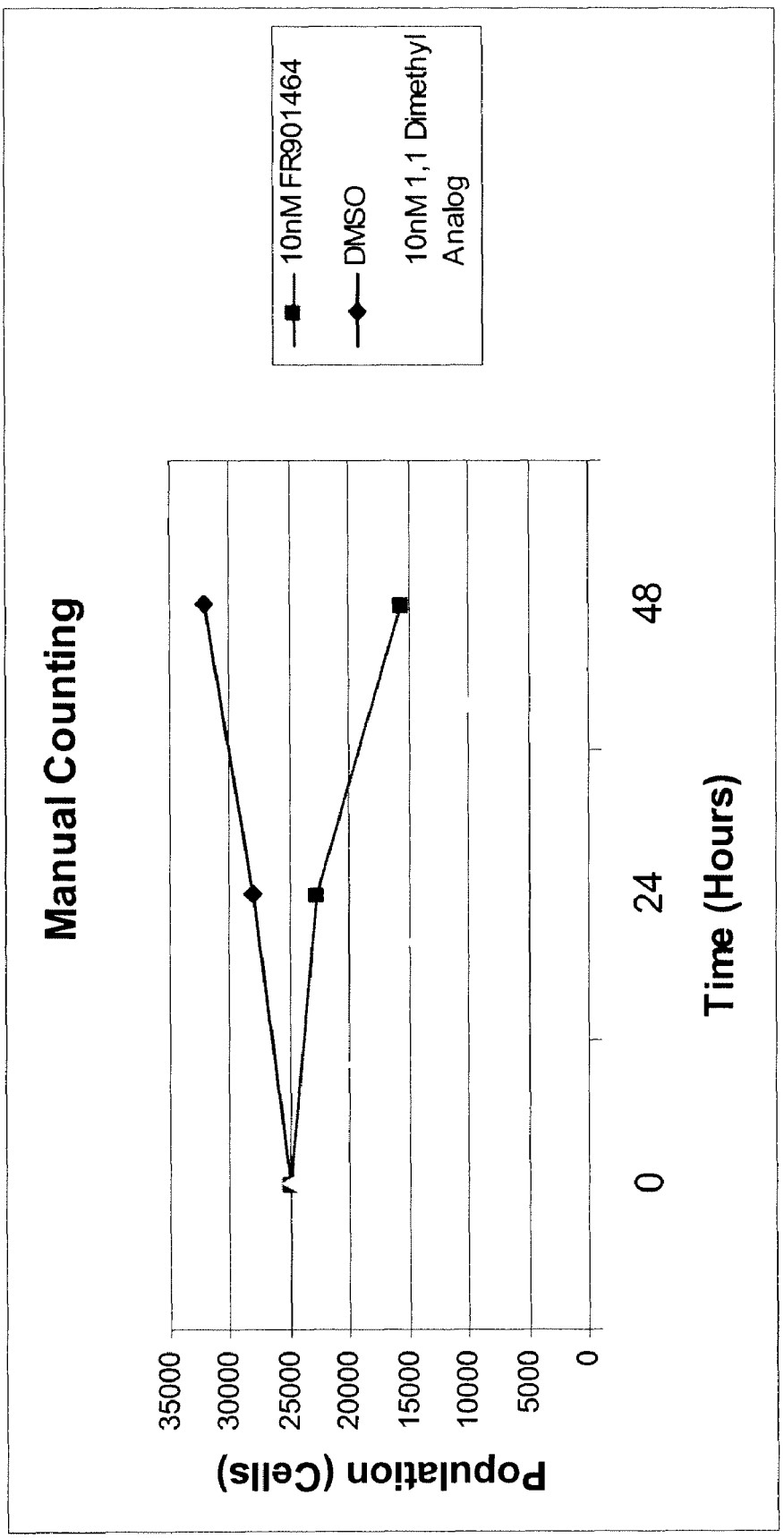
FIG. 1 is a graph that compares the viability of cells, over a 48-hour period, when they are treated with FR901464 (10 nM, compound X) versus 1,1-dimethyl-desoxy analog (10 nM compound IX).
Figure 2:
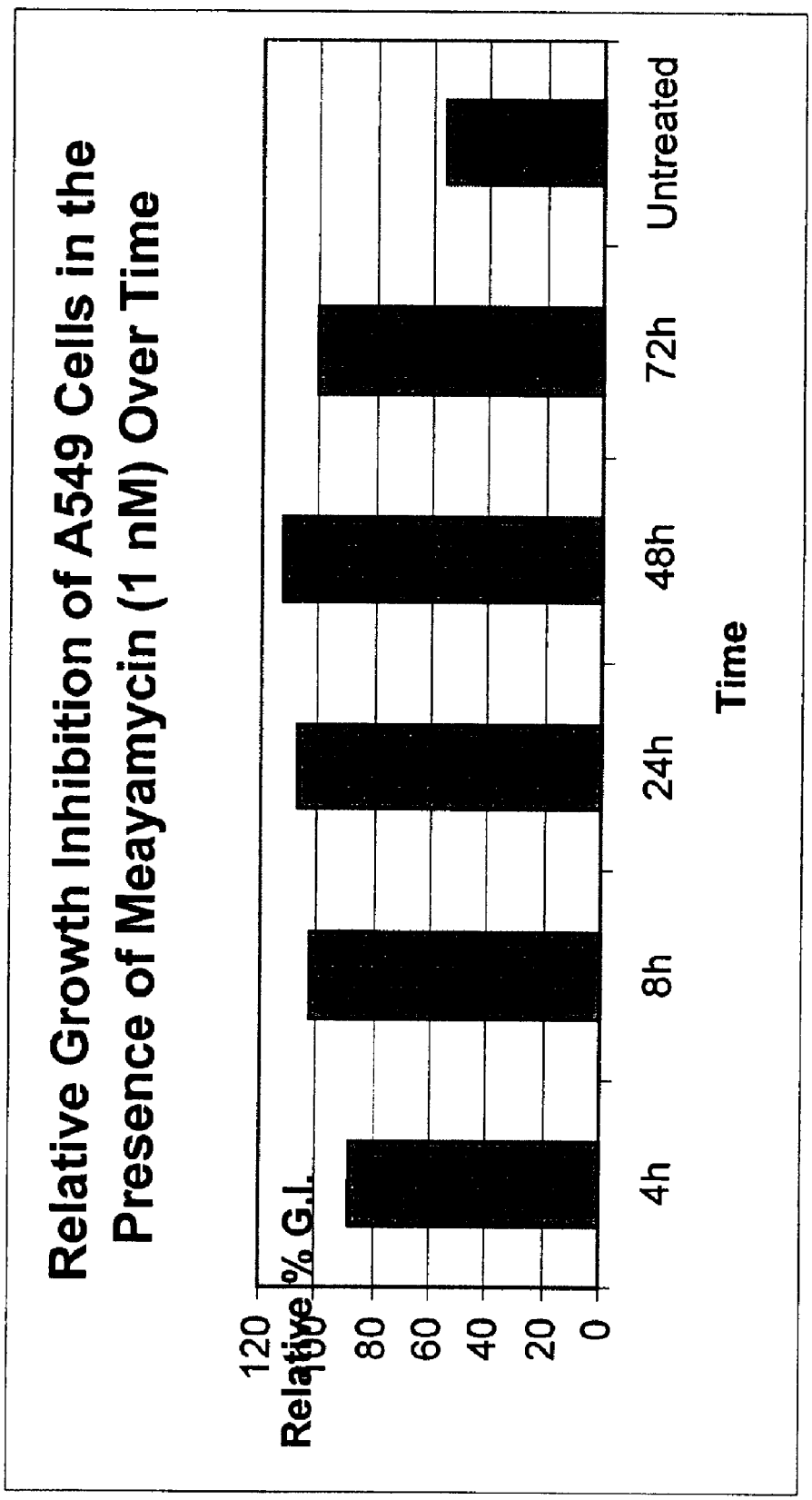
FIG. 2 shows relative growth Inhibition of A549 cells in the presence of meayamycin (1 nM) over time.
Figure 3:
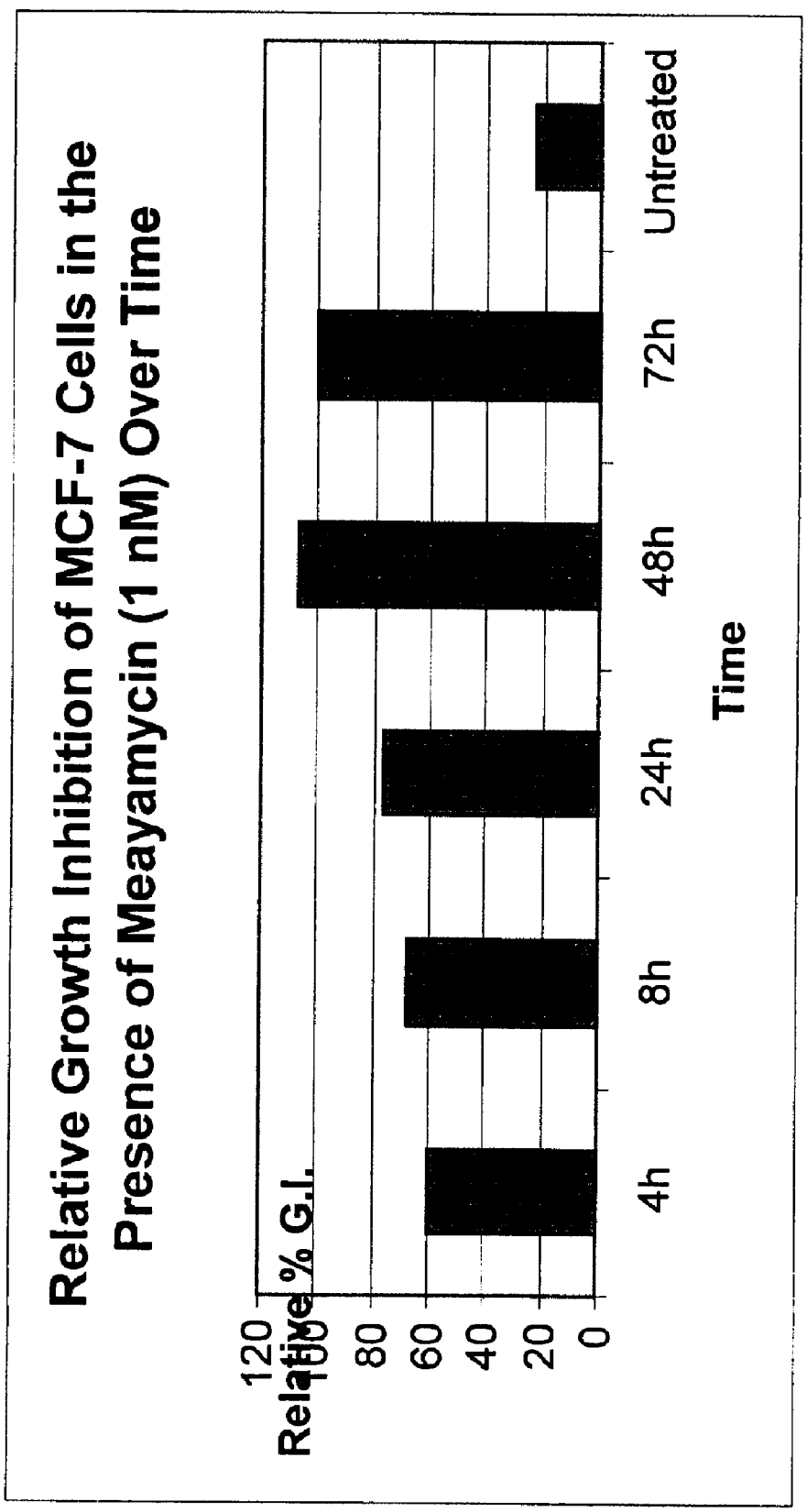
FIG. 3 shows relative growth inhibition of MCF-7 cells in the presence of meayamycin (1 nM) over time.
Figure 4:
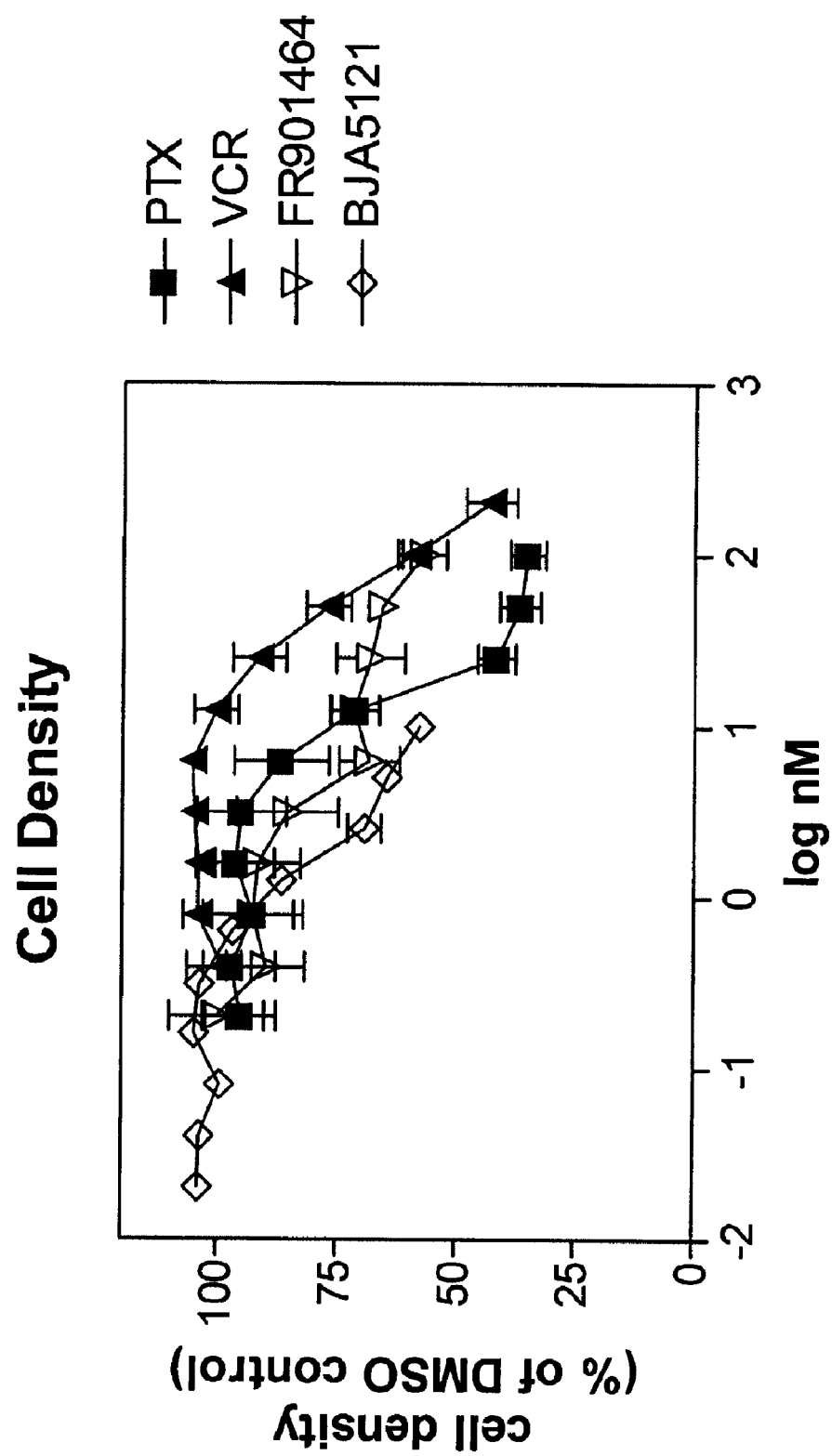
FIG. 4 shows the inhibition of A549 cells by meavamycin (BJA5121=meayamycin PTX=paclitaxel; VCR=vincristine).
Figure 5:
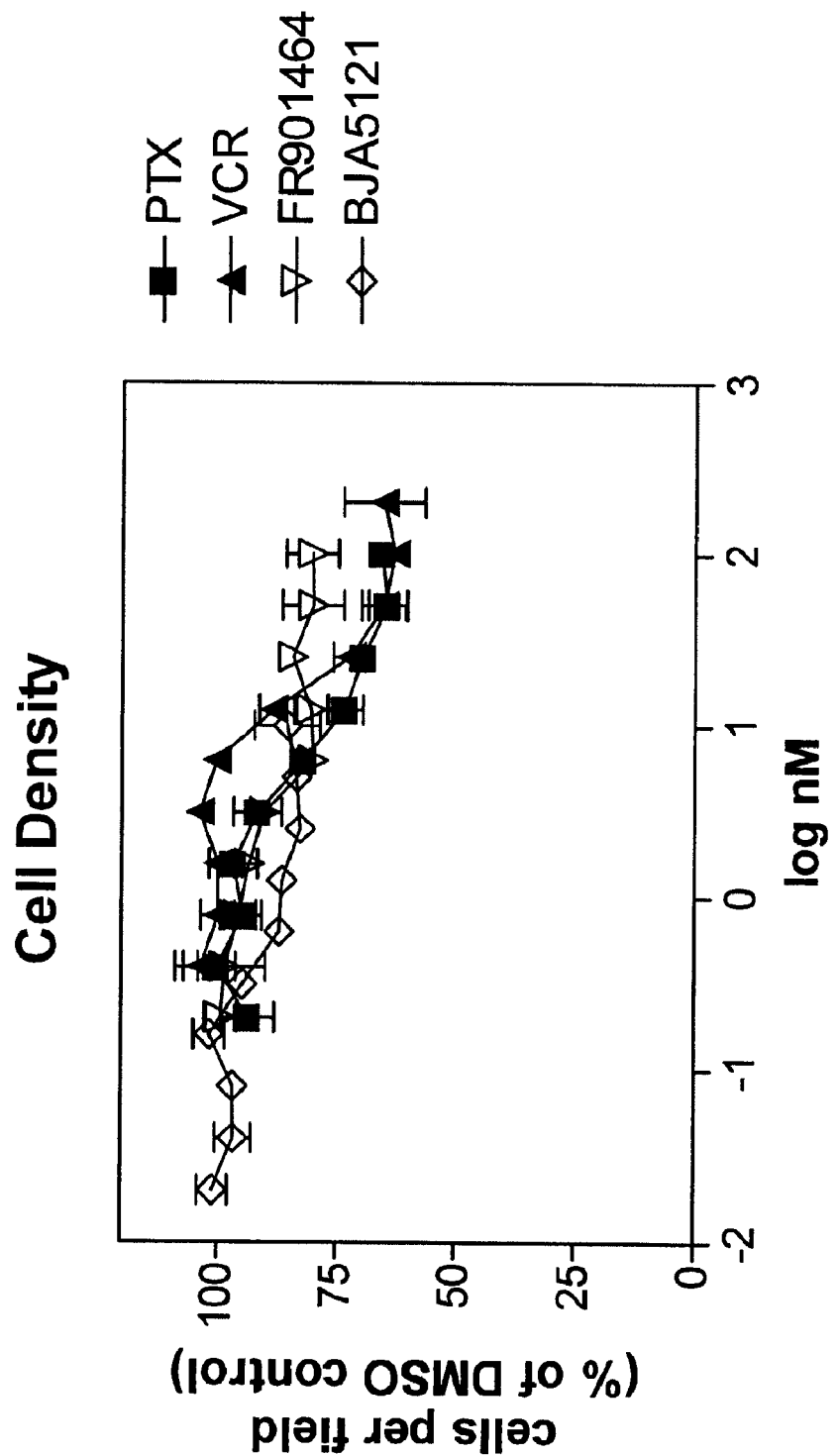
FIG. 5 shows the inhibition of IMR-90d cells by meayamycin (BJA5121=meayamycin; PTX=paclitaxel; VCR=vincristine).

It is to be understood that the terminology used herein is for the purpose of describing particular embodiments only and is not intended to limit the scope of the present invention. The following definitions shall apply unless otherwise indicated.

The phrase "cellular proliferative disorder" refers to a disease or pathology that is characterized by abnormal, uncontrolled cell division. Exemplary of such disorders and pathologies are neoplasia, including cancers, hyperplasias such as endometrial hyperplasia and benign prostatic hyperplasia, restenosis, cardiac hypertrophy, immune disorders characterized, for example, by a dysfunctional proliferation response of the cellular immune system, and inflammation. Illustrative cancers in this regard are acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor.

"$C_{1-6}$-alkyl" refers to monovalent saturated aliphatic hydrocarbyl groups having from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—).

"Halo" or "halogen" refers to fluoro, chloro, bromo and iodo.

"Halo($C_{1-6}$-alkyl)" refers to $C_{1-6}$-alkyl groups substituted with 1 to 3 or 1 to 2 halo groups, wherein $C_{1-6}$-alkyl and halo are as defined herein. The term includes, for example, $CF_3$.

The term "heteroaryl" as used herein refers to an aromatic heterocycle ring of 5 to 14 members, such as 5 to 6 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl.

The term "heterocycle" or "heterocycloalkyl" as used herein refers to 5- to 14-membered ring systems, such as 5- to 6-membered ring systems, which are either saturated, unsaturated, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles may be monocyclic, bicyclic, or tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thuiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl.

"Hydroxy" refers to the group —OH.

"Hydroxy protecting group" refers to protecting groups for an OH group. Suitable hydroxy protecting groups as well as suitable conditions for protecting and deprotecting particular functional groups are well known in the art. For example, numerous such protecting groups are described in T. W. Greene and P. G. M. Wuts, PROTECTING GROUPS IN ORGANIC SYNTHESIS, $3^{rd}$ ed., Wiley, New York. Such hydroxy protecting groups include $C_{1-6}$ alkyl ethers, benzyl ethers, p-methoxybenzyl ethers, silyl ethers, and the like.

"$C_{1-6}$-alkoxy" refers to the group —O-($C_{1-6}$-alkyl) wherein $C_{1-6}$-alkyl is defined herein. $C_{1-6}$-alkoxy includes, by way of example, methoxy, ethoxy, n-propoxy, isopropoxy, n-butoxy, t-butoxy, sec-butoxy, and n-pentoxy.

"Patient" refers to mammals and includes humans and non-human mammals.

"Pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Red-Al" refers to sodium bis(2-methoxyethoxy)aluminum hydride.

"Stereoisomer" or "stereoisomers" refer to compounds that differ in the chirality of one or more stereocenters. Stereoisomers include enantiomers, diastereomers, and racemates.

"TES" refers to triethylsilyl ($Et_3Si$—)

"Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease.

Accordingly, the present invention provides a compound, stereoisomer, or pharmaceutically acceptable salt or ester thereof having Formula I as described generally hereinabove:

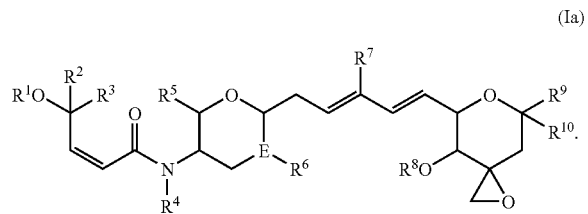

In one embodiment, provided is a compound having Formula (Ib):

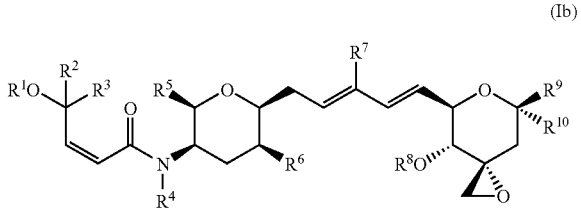

wherein $R^1$, $R^2$, $R^3$, $R^4$, $R^5$, $R^6$, $R^7$, $R^8$, $R^9$, and $R^{10}$ are as previously defined.

In another embodiment, provided is a compound having Formula (Ic):

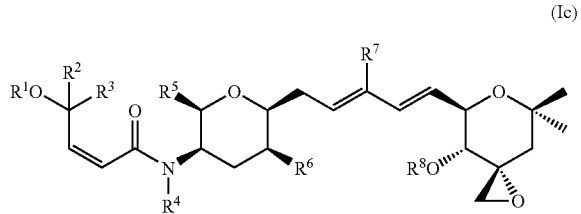

wherein $R^1$, $R^2$, $R^3$, $R^4$, $R^5$, $R^6$, $R^7$, $R^8$, $R^9$, and $R^{10}$ are as previously defined.

In some embodiments, $R^1$ is $C(O)R^{11}$ and $R^{11}$ is $C_{1-6}$-alkyl or halo($C_{1-6}$-alkyl). In some aspects, $R^1$ is $C(O)CH_3$.

In some embodiments, at least one of $R^2$, $R^3$, $R^5$, and $R^6$ is $C_{1-6}$-alkyl. In some aspects, at least one of $R^2$, $R^3$, $R^5$, and $R^6$ is $CH_3$. In some aspects, $R^3$ and $R^5$ are $CH_3$.

In some embodiments, $R^2$ is hydrogen.

In some embodiments, $R^4$ is hydrogen.

In some embodiments, $R^6$ is hydrogen.

In some embodiments, $R^7$ is $CH_3$ or $CF_3$

In some embodiments, at least one of $R^9$ and $R^{10}$ is independently selected from the group consisting of $C_{1-6}$-alkyl and $C_{1-6}$-alkyl substituted with one to three groups independently selected from halo, hydroxy, and $C_{1-6}$-alkoxy. In other embodiments, at least one of $R^9$ and $R^{10}$ is independently selected from the group consisting of $CH_3$, $CH_2I$, and $CH_2OH$.

Exemplary compounds of the present invention include:

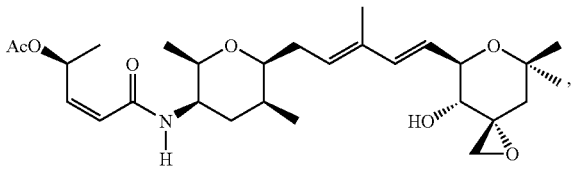

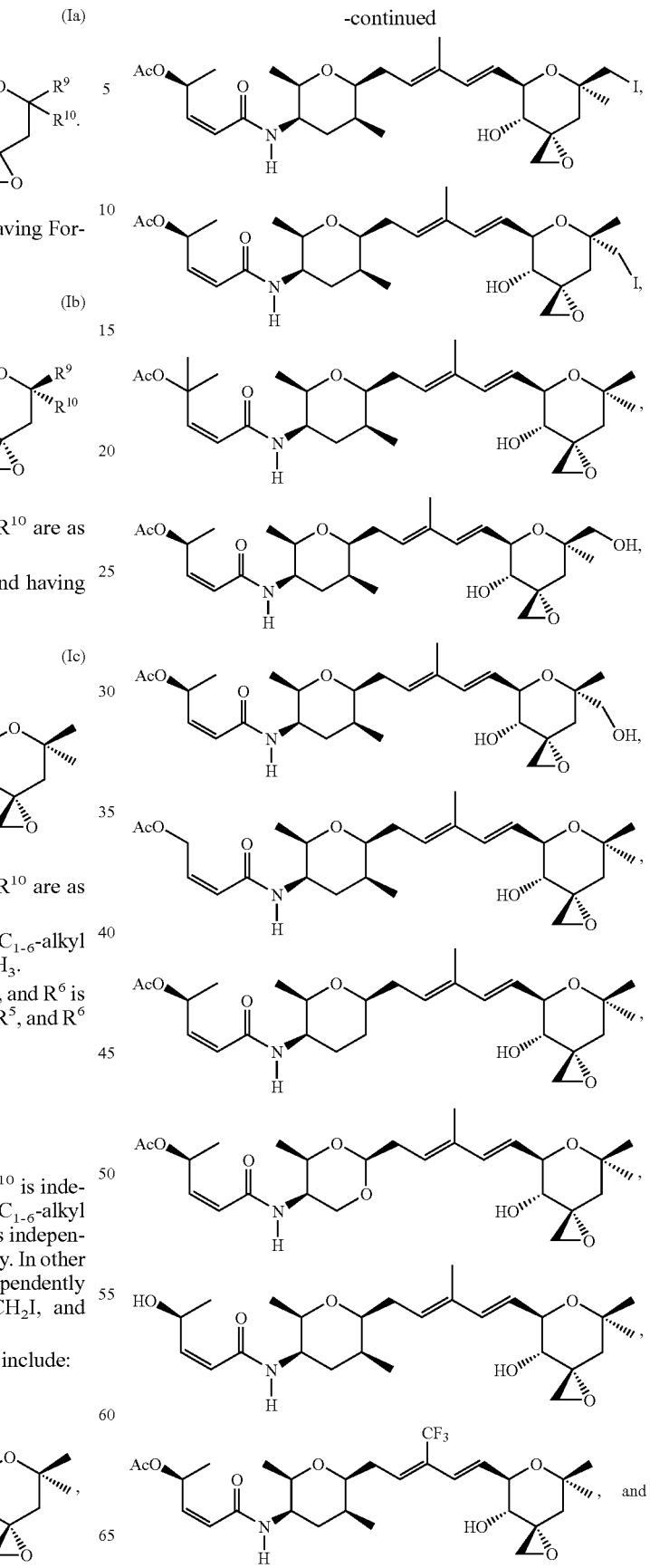

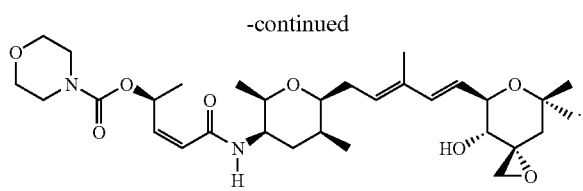

In other embodiments provided is a pharmaceutical composition comprising a compound, stereoisomer, or pharmaceutically acceptable salt or ester thereof of Formula I, (Ib), or (Ic) and a pharmaceutically acceptable carrier.

In some embodiments, the composition comprises a compound or pharmaceutically acceptable ester or ester thereof of Formula (IX):

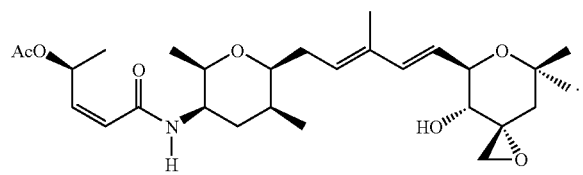

(IX)

Other embodiments are methods for treating a cellular proliferative disorder in a patient, comprising administering to the patient a therapeutically effective amount of any of the embodiments of a compound, stereoisomer, or pharmaceutically acceptable salt or ester thereof of Formula I, (Ib), or (Ic). In some embodiments, the compound is of Formula (IX) or a pharmaceutically acceptable salt or ester thereof.

Not wishing to be bound by any particular theory, the inventors believe that the compounds described herein inhibit RNA splicing. The invention therefore contemplates in other embodiments a method of treating a disease or disorder that is associated with RNA splicing. Illustrative of this category of RNA splicing-related conditions are cystic fibrosis, Duchenne muscular dystrophy, Fanconi anemia, and neurofibromatosis, among other genetic diseases, as well as a cellular proliferative disorder described above, e.g., breast cancer, ovarian cancer, and prostate cancer. Dysfunctional RNA splicing is understood also to play a role in various inflammatory diseases, such as rheumatoid arthritis and psoriasis, in certain cardiovascular disorders, and in the pathology of infections by oncogenic viruses and other virus types, such as Borna disease virus and HIV, by parasitic infections and fungal infections.

In accordance with another of its aspects, the present invention encompasses the combination of a compound of the invention, as described above, with an antibody that targets the impact of the compound when the combination is administered in vivo. Exemplary of such a combination is a conjugate of an antibody with an inventive compound. Such conjugates have a recognized usefulness for the targeted administration of the compounds. That is, the antibody has a binding specificity for an epitope that is characteristic of a target cell or tissue, whereby the antibody directs the drug (here, a compound of the invention) to that cell or tissue where the compound is needed. The result is an increased potency for the compound and a reduction or even an elimination of toxicity that otherwise may be associated with whole-body administration of the compound.

Antibodies that are suitable for this purpose, in accordance with the invention, may be monoclonal or polyclonal, so long as the requisite specificity is achieved for the in vivo target. The targeting component of the combination also can be an antibody fragment, such as an Fab fragment, or a single-chain binding molecule, produced recombinantly, as well as a chimeric or humanized antibody. Many such antibodies and binding molecules are known, as evidenced, for example, by U.S. Patent Application Publication No. 2005/0276812.

The targeting component can be linked to the compound of the invention via a linker moiety. In general, the linker moiety is bound to a compound of the present invention through hydroxyl or amino groups. Synthetic approaches for attaching the targeting component through a linker moiety are conventional in the field. Exemplary linker moieties and related attachment chemistries are described, for instance, in the above-mentioned published '812 application, in U.S. Pat. No. 5,010,176, U.S. Pat. No. 5,156,840, U.S. Pat. No. 5,272,253, U.S. Pat. Nos. 5,514,794, 5,643,573, U.S. Pat. No. 5,665,358 and U.S. Pat. No. 5,795,560, and in C. F. McDonagh et al., Protein Eng'rg Design & Selection 19: 299-308 (2006).

Administration and Pharmaceutical Composition

In general, the compounds of this invention are administered in a therapeutically effective amount by any of the accepted modes of administration for agents that serve similar utilities. The actual amount of the compound of this invention, as the active ingredient, will depend upon numerous factors, such as the severity of the disease to be treated, the age and relative health of the subject, the potency of the compound used, the route and form of administration, and other factors. The drug can be administered more than once a day, preferably once or twice a day. Assessing each of these factors is within the skill of the attending clinician.

Therapeutically effective amounts of the compounds can range from approximately 0.05 to 50 mg per kilogram body weight of the recipient per day; such as about 0.1-25 mg/kg/day, or from about 0.5 to 10 mg/kg/day. Thus, for administration to a 70 kg person, for instance, the dosage range can be about 35-70 mg per day.

The compounds can be used alone or in compositions together with a pharmaceutically acceptable carrier or excipient. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable, pharmaceutically acceptable excipients are described in REMINGTON'S PHARMACEUTICAL SCIENCES, Mack Pub. Co., New Jersey (1991), incorporated herein by reference.

In general, compounds of the invention are administered as pharmaceutical compositions by any one of the following routes: oral, systemic (e.g., transdermal, intranasal or by suppository), parenteral (e.g., intramuscular, intravenous or subcutaneous), or intrathecal administration. One manner of administration is oral, using a convenient daily dosage regimen that is adjusted according to the degree of affliction. Compositions can take the form of tablets, pills, capsules, semisolids, powders, sustained release formulations, solutions, suspensions, elixirs, aerosols, ointments, or any other appropriate compositions. Another manner for administering an inventive compounds is inhalation, which delivers a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. Inert gases suitable for this purpose are nitrogen, carbon dioxide, etc. There are several types of pharmaceutical inhalation devices-nebulizer inhalers, metered dose inhalers (MDI), and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The amount of the compound in a formulation can vary within the full range employed by those skilled in the art. Typically, the formulation contains, on a weight percent (wt %) basis, from about 0.01-99.99 wt % of the compound of based on the total formulation, with the balance being one or more suitable pharmaceutical excipients. For example, in some embodiments the compound is present at a level of about 1-80 wt %.

General Synthetic Methods

Compounds of this invention are prepared from readily available starting materials using the following general methods and procedures. It will be appreciated that where typical process conditions (i.e., reaction temperatures, times, mole ratios of reactants, solvents, pressures, etc) are given, other process conditions can also be used unless otherwise stated. Optimum reaction conditions vary with the particular reactants or solvent used, but such conditions are determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Greene and Wuts, supra.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers and enriched mixtures are included within the scope of this invention, unless otherwise indicated. Pure stereoisomers (or enriched mixtures) are prepared using, for example, optically active starting materials or stereoselective reagents well-known in the art. Alternatively, racemic mixtures of such compounds are separated using, for example, chiral column chromatography, chiral resolving agents and the like.

The various starting materials, intermediates, and compounds of the invention are isolated and purified where appropriate using conventional techniques such as precipitation, filtration, crystallization, evaporation, distillation, and chromatography. Characterization of these compounds are performed using conventional methods such as by melting point, mass spectrum, nuclear magnetic resonance, and various other spectroscopic analyses.

In one embodiment, provided is a process for preparing a compound, stereoisomer, or pharmaceutically acceptable salt or ester thereof having Formula I:

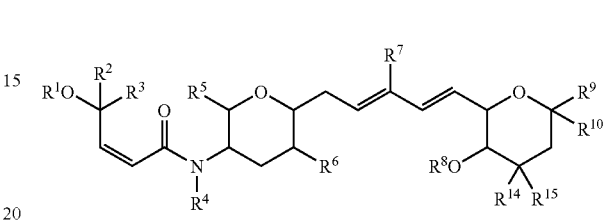

wherein $R^1$ and $R^8$ are independently selected from the group consisting of H, Pg, $C_{1-6}$-alkyl, halo($C_{1-6}$-alkyl), $C(O)R^{11}$, $C(O)OR^{11}$, and $C(O)NR^{12}R^{13}$, wherein each $R^{11}$ is independently H, $C_{1-6}$-alkyl, or halo($C_{1-6}$-alkyl), and wherein $R^{12}$ and $R^{13}$ are selected independently from the group consisting of H, $C_{1-6}$-alkyl, and halo($C_{1-6}$-alkyl);

or $R^{12}$ and $R^{13}$, together with the nitrogen atom to which they are bound, form a 5- to 6-membered heterocyclic or heteroaromatic ring;

$R^2$, $R^3$, $R^4$, $R^5$, and $R^6$ are independently selected from the group consisting of H, $C_{1-6}$-alkyl, and halo($C_{1-6}$-alkyl);

$R^7$ is selected from the group consisting of H, $C_{1-6}$-alkyl and halo($C_{1-6}$-alkyl); and $R^9$ and $R^{10}$ are independently selected from the group consisting of H, $C_{1-6}$-alkyl, and $C_{1-6}$-alkyl substituted with one to three groups independently selected from halo, hydroxy, $C_{1-6}$-alkoxy, and OPg;

$R^{14}$ and $R^{15}$ are selected independently from the group consisting of halo($C_{1-6}$-alkyl), $C(O)R^{11}$, F, Cl, $NO_2$, and $B(OR^{11})_2$, wherein $R^{11}$ is as defined above; or $R^{14}$ and $R^{15}$, together with the carbon atom to which they are bound, form an epoxide ring; and each Pg is independently a hydroxy protecting group;

said method comprising contacting a compound of Formula (II) wherein E, $R^1$, $R^2$, $R^3$, $R^4$, $R^5$, $R^6$, and $R^7$ are as defined hereinabove:

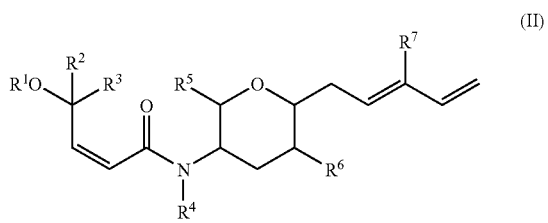

with a compound of Formula (III) wherein $R^8$, $R^9$, $R^{10}$, $R^{14}$, and $R^{15}$ are as defined hereinabove:

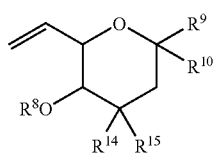

in the presence of an olefin metathesis catalyst to provide a compound of Formula I, provided that, when $R^1$ is $C(O)CH_3$; $R^2$, $R^4$, and $R^8$ are hydrogen; $R^3$, $R^5$, $R^6$, $R^7$, and $R^9$ are methyl; and $R^{10}$ is OH, then the compound of Formula (III) is a compound of Formula (IIIa):

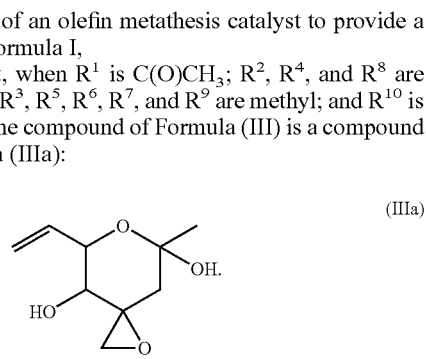

In accordance with one aspect of the invention, the compound of Formula (Id) is compound (IX):

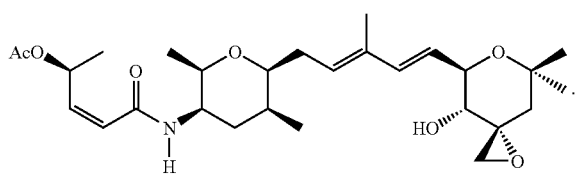

Pursuant to another embodiment of the invention, a process is provided for preparing a compound, stereoisomer, or pharmaceutically acceptable salt or ester thereof having Formula I:

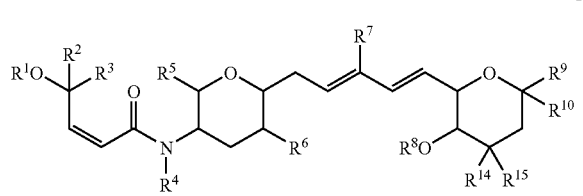

wherein $R^1$ and $R^8$ are independently selected from the group consisting of H, Pg, $C_{1-6}$-alkyl, halo($C_{1-6}$-alkyl), $C(O)R^{11}$, $C(O)OR^{11}$, and $C(O)NR^{12}R^{13}$, wherein each $R^{11}$ is independently H, $C_{1-6}$-alkyl, or halo ($C_{1-6}$-alkyl), and wherein $R^{12}$ and $R^{13}$ are selected independently from the group consisting of H, $C_{1-6}$-alkyl, and halo($C_{1-6}$-alkyl);

or $R^{12}$ and $R^{13}$, together with the nitrogen atom to which they are bound, form a 5- to 6-membered heterocyclic or heteroaromatic ring;

$R^2$, $R^3$, $R^4$, $R^5$, and $R^6$ are independently selected from the group consisting of H, $C_{1-6}$-alkyl, and halo($C_{1-6}$-alkyl);

$R^7$ is selected from the group consisting of H, $C_{1-6}$-alkyl and halo($C_{1-6}$-alkyl); and $R^9$ and $R^{10}$ are independently selected from the group consisting of H, $C_{1-6}$-alkyl, and $C_{1-6}$-alkyl substituted with one to three groups independently selected from halo, hydroxy, $C_{1-6}$-alkoxy, and OPg;

$R^{14}$ and $R^{15}$ are selected independently from the group consisting of halo($C_{1-6}$-alkyl), $C(O)R^{11}$, F, Cl, $NO_2$, and $B(OR^{11})_2$, wherein $R^{11}$ is as defined above;

or $R^{14}$ and $R^{15}$, together with the carbon atom to which they are bound, form an epoxide ring.

This process comprises:

(a) contacting a compound of Formula (IVc) wherein $R^9$, $R^4$, and $R^{15}$ are as defined hereinabove and $P^1$ is a hydroxy protecting group with an oxidizing agent to form a first compound of Formula (V) wherein $R^9$, $R^{14}$, and $R^{15}$ are as defined hereinabove, $P^1$ is a hydroxy protecting group, and $P^2$ is hydrogen:

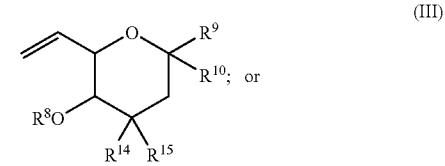

(b) converting a first compound of Formula (V) wherein $P^1$ is a hydroxy protecting group and $P^2$ is hydrogen to a second compound of Formula (V) wherein $P^1$ and $P^2$ are hydroxy protecting groups;

(c) optionally converting said first or second compound of Formula (V) under cyclization conditions to a compound of Formula (III) wherein $R^8$, $R^9$, and $R^{10}$ are as defined herein:

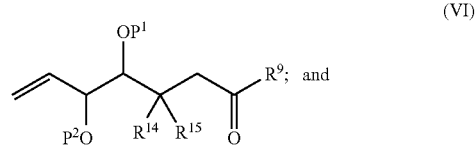

(d) optionally converting said second compound of Formula (V) under oxidative conditions to a compound of Formula (VI) wherein $R^9$, $R^{14}$, and $R^{15}$ are as defined hereinabove, and $P^1$ and $P^2$ are hydroxy protecting groups; and converting the compound of Formula (VI) under cyclization conditions to a compound of Formula (III):

(VI)

(e) contacting a compound of Formula (III) with a compound of Formula (II) wherein E, $R^1$, $R^2$, $R^3$, $R^4$, $R^5$, $R^6$, and $R^7$ are as defined herein:

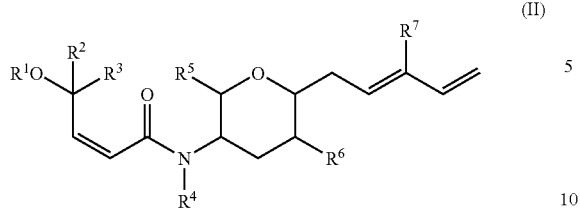

(II)

in the presence of an olefin metathesis catalyst to form a compound of Formula I.

In one embodiment, the cyclization conditions of part (c) comprise treatment of a compound of Formula (V) with $Hg(OAc)_2/NaBH_4/Et_3B$. In another embodiment, the cyclization conditions comprises treatment with NaI and $Pb(OAc)_4$.

In another embodiment, the oxidative conditions of part (d) comprise treatment with $OsO_4$, an oxidant such as NMO, and $Pb(OAc)_4$.

In one embodiment, the cyclization conditions of part (d) comprise treatment of a compound of Formula (VI) with an acidic solution, such as $AcOH/THF/H_2O$.

In some embodiments, the hydroxy protection groups of compounds of Formulae (V) and (VI) are silyl protecting groups such as triethylsilyl.

In another embodiment of the invention, the compound of Formula (IVc) is prepared by (a) contacting a compound of Formula (VII) with $Ag\text{—}CC\text{—}CO_2Me$ and $Cp_2ZrCl_2$ to form a compound of Formula (VIII) wherein $R^9$, $R^{14}$, and $R^{15}$ are as defined hereinabove:

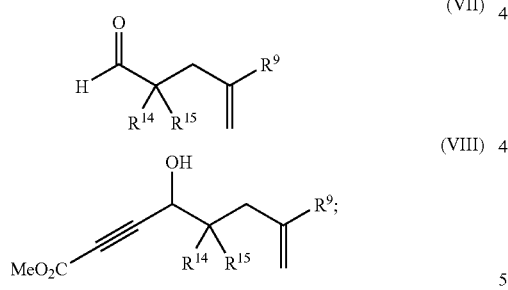

(VII)

(VIII)

(b) contacting a compound of Formula (VIII) with Red-Al to form a compound of Formula (IVa) wherein $P^1$ is hydrogen:

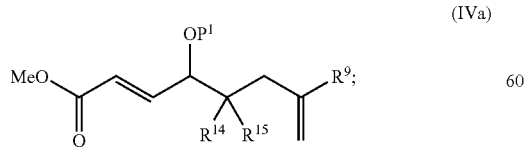

(IVa)

(c) converting a compound of Formula (IVa) wherein $P^1$ is hydrogen to a compound of Formula (IVa) wherein $P^1$ is a hydrogen protecting group;

(d) contacting a compound of Formula (IVa) wherein $P^1$ is a hydrogen protecting group with a reducing agent to form a compound of Formula (IVb) wherein $P^1$ is a hydrogen protecting group

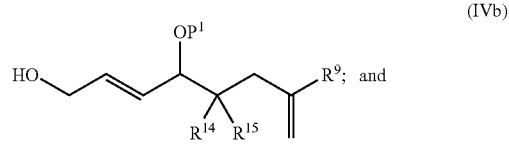

(IVb)

(e) reacting a compound of Formula (IVb) wherein $P^1$ is a hydrogen protecting group with $o\text{-}O_2N\text{-}PhSeCN$ under selenide forming conditions to a compound of Formula (IVc):

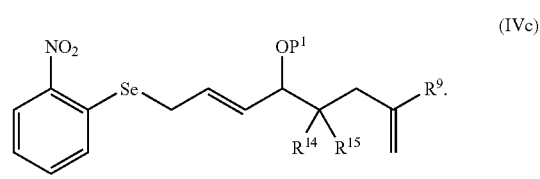

(IVc)

In some embodiments, the reducing agent of part (d) is diisobutylaluminum hydride.

In some embodiments, the selenide forming conditions of part (e) comprise treatment of a compound of Formula (IVb) with a phosphine and an oxidizing agent. Suitable phosphines and oxidizing agents include tributylphosphine and hydrogen peroxide.

In accordance with another embodiment of the invention, the compound of Formula (Ie) is compound (X):

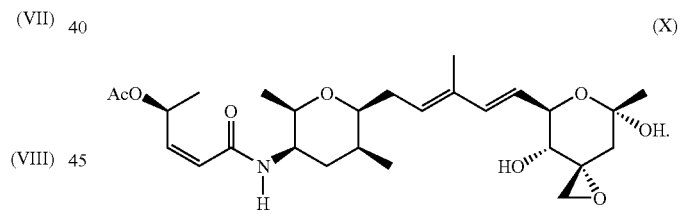

(X)

Pursuant to another embodiment, an intermediate compound of Formula (IV) is provided:

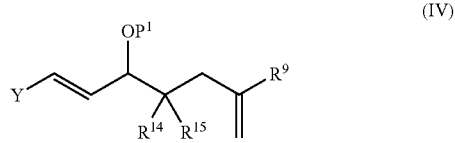

(IV)

wherein

Y is selected from the group consisting of $MeO_2C\text{—}$, $o\text{-}O_2N\text{—}PhSeCH_2\text{—}$, and $HOCH_2\text{—}$;

$R^9$ is selected from the group consisting of $C_{1-6}$-alkyl and $C_{1-6}$-alkyl substituted with one to three groups independently selected from halo, hydroxy, $C_{1-6}$-alkoxy, and OPg;

R[14] and R[15] are selected independently from the group consisting of halo($C_{1-6}$-alkyl), C(O)R[11], F, Cl, $NO_2$, and B(OR[11])$_2$, wherein each R[11] is independently H, $C_{1-6}$-alkyl, or halo($C_{1-6}$-alkyl), or R[14] and R[15], together with the carbon atom to which they are bound, form an epoxide ring; and P[1] and Pg are independently a hydroxy protecting group.

In some embodiments, provided is a compound of Formula (IV) wherein P[1] is triethylsilyl and R[9] is $C_{1-6}$-alkyl. In other embodiments, the intermediate compound is selected from the group consisting of:

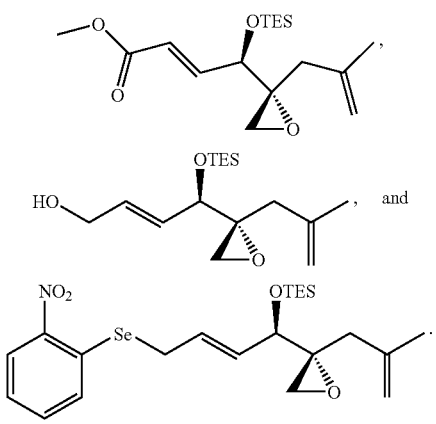

In some embodiments, the olefin metathesis catalyst is a Ruthenium catalyst. In some embodiments, the Ruthenium catalyst is (Mes=2,4,6-trimethylphenyl):

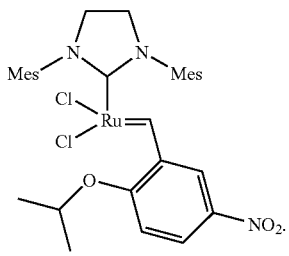

(22)

In other embodiments, the Ruthenium catalyst is:

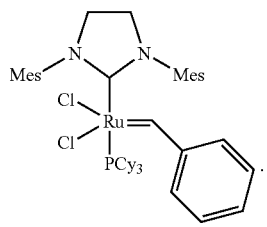

(22')

The following examples illustrate certain embodiments of the present invention, to aid the skilled person in practicing the invention. Accordingly, the examples are in no way considered to limit the scope of the invention.

EXAMPLES

General techniques. All reactions were carried out with dry, freshly distilled solvents under anhydrous conditions, unless otherwise noted. Tetrahydrofuran (THF) was distilled from sodium-benzophenone, and methylene chloride ($CH_2Cl_2$) was distilled from calcium hydride. Acetonitrile was distilled over $CaH_2$ and stored over 3 Å molecular sieves. Yields refer to chromatographically and spectroscopically ($^1$H NMR) homogenous materials, unless otherwise stated.

All reactions were monitored by thin-layer chromatography (TLC) carried out on 0.25-mm E. Merck silica gel plates (60F-254) using UV-light (254 nm), 2.4% phosphomolybdic acid/1.4% phosphoric acid/5% sulfuric acid in water, anisaldehyde in ethanol, or 0.2% ninhydrin in ethanol and heat as developing agents. TSI silica gel (230-400 mesh) was used for flash column chromatography.

NMR spectra were recorded on AM300 or AM500 (Bruker) instruments and calibrated using a solvent peak or tetramethylsilane as an internal reference. The following abbreviations are used to indicate the multiplicities: s, singlet; d, doublet; t, triplet; q, quartet; m, multiplet; br, broad. High-resolution mass spectra were obtained by using EBE geometry.

Abbreviations. Ac, acetyl; br, broad; Cp, cyclopentadienyl; EI, electron impact; ES, electrospray; Et, ethyl; EtOAc, ethyl acetate; EtOH, ethanol; HRMS, high resolution mass spectrum; Me, methyl; MeOH, methanol; Ph, phenyl; Tf, trifluoromethanesulfonyl; THF, tetrahydrofuran.

Example 1

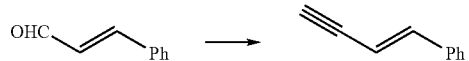

Preparation of and data for but-1-en-3-ynyl-benzene. See Miwa, K.; Aoyama, T.; Shiori, T. *Synlett* 1994, 107.

Example 2-a

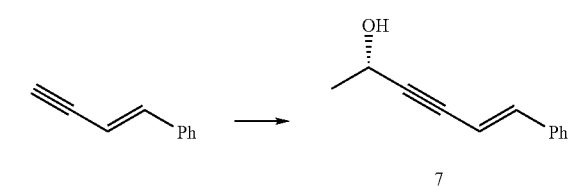

Preparation of (E)-(2S)-6-phenylhex-5-en-3-yn-2-ol (7). A flask containing Zn(OTf)$_2$ (Zinc triflate purchased from Fluka was found to give the best results, other vendor's proved inefficient; 557 mg, 1.50 mmol) and (−)-N-methylephedrine (275 mg, 1.50 mmol) was added toluene (1.5 mL) and Et$_3$N (209 μL, 1.50 mmol) at 23° C. under a nitrogen atmosphere. The resulting mixture was stirred for 2 h at 23° C. before but-1-en-3-ynyl-benzene (192 μL, 1.50 mmol) was added in one portion. After stirring for 15 min at 23° C., the reaction was cooled to 0° C., then acetaldehyde (168 μL, 30.0 mmol) was added at the same temperature in one portion. The resulting mixture was warmed to 23° C. and stirred for 35 h, then quenched by the addition of saturated aqueous NH$_4$Cl (3 mL). The mixture was poured into a separatory funnel and diluted with EtOAc (5 mL). The layers were separated and the aqueous layer was extracted with EtOAc (3×3 mL). The combined organic layers were dried over $Na_2SO_4$, filtered, and concentrated in vacuo. Purification of the residue via flash chromatography (0→20% EtOAc/hexanes) afforded compound 7 (106 mg, 41%, 72% ee; the ee was determined after making the acetate ester) as a pale yellow oil.

Data for 7: $R_f$=0.40 (30% EtOAc in hexanes); $[\alpha]_D^{23}$ −2.4 (c 4.1, $CHCl_3$). IR (neat): 3334 (br, O—H), 3059, 3028, 2980, 2917, 2849, 2207, 1447, 1165, 1074, 1010, 953, 896 $cm^{-1}$; $^1H$ NMR (300 MHz, 293K, $CDCl_3$) δ 7.33-7.20 (m, 5H), 6.89 (d, 1H, J=16.3 Hz), 6.11 (dd, 1H, J=16.3, 1.7 Hz), 4.65 (br q, 1H, J=6.4 Hz), 1.91 (br s, 1H), 1.46 (d, 3H, J=6.6 Hz); $^{13}C$ NMR (75 MHz, 293K, $CDCl_3$) δ 141.7, 136.0, 128.7, 128.4, 126.2, 107.4, 93.1, 83.2, 58.9, 24.3; HRMS (EI+) calcd. for $C_{12}H_{12}O$ ($M^+$) 172.0888, found 172.0889.

Recrystallization of a batch of 7 of lower enantiopurity was accomplished by dissolving 7 (1.80 g, 64% ee) in $Et_2O$ (5 mL), then diluting the resulting solution with hexanes (15 mL) at 23° C. The resulting solution was then cooled to −20° C. After 10 h at the same temperature, the solution was filtered, washed with hexanes, and cold 5% EtOAc/hexanes (5 mL) to afford 7 (664 mg, 95% $ee^2$) as colorless needles, which was used for the subsequent steps.

Data for recrystallized 7: $[\alpha]_D^{23}$ −2.8 (c 1.5, $CHCl_3$), m.p.=50-51° C.

Example 2-b

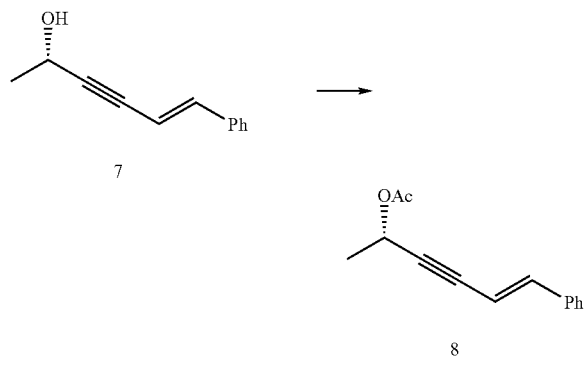

Preparation of (E)-(2S)-6-phenylhex-5-en-3-yn-2-yl acetate (8). To a solution of alcohol 7 (400 mg, 2.32 mmol) in pyridine (pyridine was distilled over $CaH_2$ and stored over KOH; 4.6 mL) at 23° C. was added acetic anhydride (1.10 mL, 11.6 mmol). The resulting mixture was stirred for 2 h at 23° C. The reaction was quenched by 1 N aqueous HCl (10 mL) at 0° C. and diluted with EtOAc (5 mL). The mixture was poured into a separatory funnel. The layers were separated and the aqueous layer was extracted with EtOAc (3×3 mL). The combined organic layers were washed with brine (5 mL), dried over $Na_2SO_4$, filtered, and concentrated in vacuo. Purification of the residue via flash chromatography (silica gel 40 mL; 5→30% EtOAc in hexanes) afforded acetate 8 (486 mg, 98%, 95% ee; the ee value was determined by HPLC((S,S) Whelk; 25 cm, 1.0 mL/min, hexanes/$^iPrOH$=95/5).) as a colorless oil.

Data for 8: $R_f$=0.44 (20% EtOAc in hexanes); $[\alpha]_D^{23}$ −178 (c 1.9, $CHCl_3$); IR (neat): 2988, 2923, 2851, 1741 (C═O), 1448, 1370, 1233, 1175, 1063, 1019, 953, 747 $cm^{-1}$; $^1H$ NMR (300 MHz, 293K, $CDCl_3$) δ 7.52-7.31 (m, 5H), 6.98 (d, 1H, J=16.3 Hz), 6.16 (dd, 1H, J=16.3, 1.8 Hz), 5.63 (qd, 1H, J=6.6, 1.8 Hz), 2.11 (s, 3H), 1.55 (d, 3H, J=6.6 Hz). $^{13}C$ NMR (75 MHz, 293K, $CDCl_3$) δ 170.0, 142.3, 135.9, 128.8, 128.7, 126.3, 107.1, 89.4, 83.7, 60.9, 21.4, 21.1; HRMS (EI+) calcd. for $C_{14}H_{14}O_2$ ($M^+$) 214.0994, found 214.0994.

Example 3

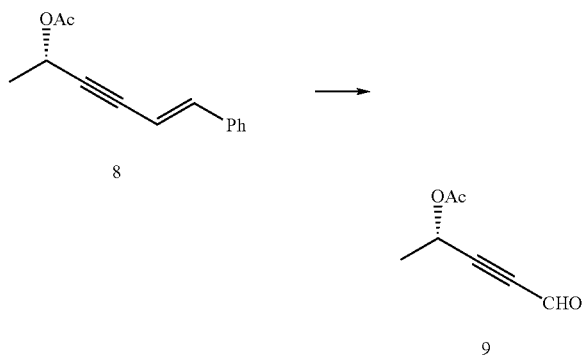

Preparation of (S)-4-formylbut-3-yn-2-yl acetate (9). A solution of 8 (392 mg, 1.83 mmol) in methanol (4.6 mL) was treated with $O_3$ for 3 min at −78° C. After removing excess $O_3$, the reaction was quenched by slow addition of methylsulfide (1.35 mL, 18.3 mmol) at −78° C. The resulting mixture was stirred for 1 h at −78° C. and for 1 h at 23° C., and then concentrated in vacuo. Purification of the residue via flash chromatography (silica gel 16 mL; 5→15% EtOAc in hexanes) afforded aldehyde 9 (208 mg, 81%) as a colorless oil.

Data for 9: $R_f$=0.49 (15% EtOAc in hexanes); $[\alpha]_D^{26}$ −167 (c 1.3, $CHCl_3$); IR (neat): 2996, 2942, 2230, 1749 (C═O), 1672 (C═O), 1372, 1231, 1157, 1065, 1018 $cm^{-1}$; $^1H$ NMR (300 MHz, 293K, $CDCl_3$) δ 9.23 (s, 1H), 5.57 (q, 1H, J=6.6 Hz), 2.11 (s, 3H), 1.57 (d, 3H, J=6.6 Hz); $^{13}C$ NMR (75 MHz, 293K, $CDCl_3$) δ 176.2, 169.7, 93.5, 83.3, 59.5, 20.8, 20.2; HRMS (EI+) calcd. for $C_6H_5O_3$ $(M-CH_3)^+$ 125.0239, found 125.0240.

Example 4

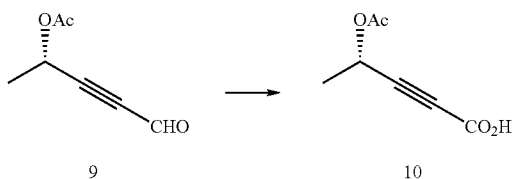

Preparation of (S)-4-acetoxypent-2-ynoic acid (10). To a solution of 9 (133 mg, 0.949 mmol) and 2-methyl-2-butene (1.20 mL, 14.2 mmol) in $^tBuOH$ (1.9 mL) was added the mixture of $NaClO_2$ (257 mg, 2.84 mmol) and $NaH_2PO_4$ (393 mg, 2.84 mmol) in $H_2O$ (1.9 mL) at 23° C. The resulting mixture was stirred for 20 min at the same temperature and quenched by 1 N aqueous HCl (3 mL) at 0° C. The mixture was poured into a separatory funnel and diluted with EtOAc (3 mL). The layers were separated and the aqueous layer was extracted with EtOAc (3×4 mL). The combined organic layers were dried over $Na_2SO_4$, filtered, and concentrated in vacuo. Purification of the residue via flash chromatography (silica gel 15 mL; 50→100% EtOAc in hexanes containing 1.0% acetic acid) afforded acid 10 (149 mg, quantitative yield) as a pale yellow oil.

Data for 10: $R_f$=0.22 (1.0% acetic acid in EtOAc); $[\alpha]_D^{26}$ −128 (c 1.6, $CH_2Cl_2$); IR (neat): 3188 (broad, O—H), 2984, 2941, 2248, 1749 (C=O), 1719 (C=O), 1374, 1227, 1049 $cm^{-1}$; $^1$H NMR (300 MHz, 293K, $CDCl_3$) δ 5.54 (q, 1H, J=6.8 Hz), 2.11 (s, 3H), 1.57 (d, 3H, J=6.8 Hz); $^{13}$C NMR (75 MHz, 293K, $CDCl_3$) δ 169.9, 156.8, 87.3, 75.6, 59.4, 20.8, 20.1; HRMS (EI+) calcd. for $C_7H_6O_3$ $(M-H_2O)^+$ 138.0317, found 138.0322.

Example 5

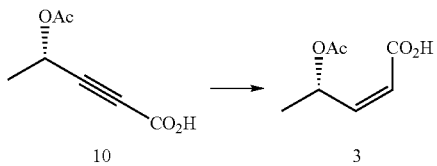

Preparation of (Z)-(4S)-acetoxypent-2-enoic acid (3). To a mixture of Lindlar catalyst (65.4 mg, 0.031 mmol) in EtOH (19.2 mL) was added quinoline (47.3 µL, 0.384 mmol). The mixture was stirred for 30 min at 23° C. To the mixture was added a solution of 10 (600 mg, 3.84 mmol) in EtOH (19.2 mL), and the resulting mixture was stirred vigorously under a hydrogen atmosphere (1 atm) for 16 h at 23° C. The mixture was filtered through paper filter and washed with EtOAc. The filtrate was concentrated in vacuo. Purification of the residue via flash chromatography (5→15% EtOAc in hexanes containing 1.0% acetic acid) afforded acid 3 (527 mg, 78%) as a pale yellow oil.

Data for 3 were consistent with the literature (*J. Am. Chem. Soc.* 2000, 122, 10482), $[\alpha]_D^{27}$ +17.8 (c 0.88, $CH_2Cl_2$).

Example 6

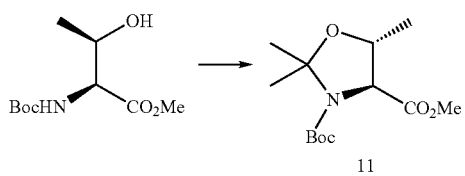

Preparation of 11. To a solution of N-(tert-butoxycarbonyl)-L-threonine methyl ester (132.78 g, 0.569 mol) in $CH_2Cl_2$ (1000 mL) was added 2-methoxypropene (109 mL, 1.138 mol) and camphorsulfonic acid (1.321 g, 5.69 mmol) at 0° C. under a nitrogen atmosphere. The resulting solution was stirred at 23° C. for 2 h. The reaction was then quenched with $Et_3N$ (5 mL) and the organic solvents were removed in vacuo. Purification of the residue via flash chromatography (silica gel 1800 mL, 5→15% EtOAc in hexanes) afforded oxazolidine 11 (151.71 g, 98%) as a pale yellow oil.

Spectroscopic data for 11 were consistent with the literature (*Tetrahedron* 1997, 53, 6473).

Example 7

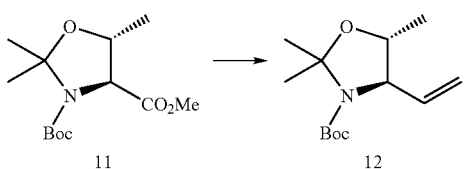

Preparation of 12. To a stirred solution of $Ph_3PCH_3Br$ (53.58 g, 150.0 mmol) in THF (150 mL) at 0° C. was added $KO^tBu$ (16.40 g, 146.2 g) in one portion. The resulting mixture was stirred for an additional one hour at the same temperature prior to use.

To a stirred solution of aminoester 11 (20.53 g, 75.11 mmol) in $CH_2Cl_2$ (250 mL) was added DIBAL-H (1 M in hexanes, 150 mL) dropwise over 2.5 h at −78° C. under a nitrogen atmosphere. After an additional 1.5 h at the same temperature, the ylide THF solution was added dropwise over 1.8 h. After an additional 15 min, the reaction mixture was warmed to 23° C., and after an additional 2.8 h at the same temperature, the reaction mixture was warmed to 48° C. After an additional 14 h at the same temperature, the reaction mixture was cooled to 23° C., diluted with $H_2O$ (100 mL) then aqueous 1 N HCl (300 mL), and the layers were separated. The aqueous residue was extracted with EtOAc (4×200 mL). The combined organic layers were washed with brine (1×500 mL), dried over anhydrous $Na_2SO_4$, filtered, and concentrated under reduced pressure. The resulting residue was purified by flash chromatography (1→5% EtOAc in hexanes) on silica gel (800 mL) to afford 12 (13.91 g, 77%) as a colorless oil.

Data for 12: $R_f$=0.48 (10% EtOAc in hexanes); IR (neat): 2979, 2935, 2880, 1702 (C=O), 1478, 1456, 1378, 1307, 1135, 1084 $cm^{-1}$; $[\alpha]_D^{22}$ +16.6 (c 3.93, $CHCl_3$); $^1$H NMR (300 MHz, 333K, $C_6D_6$) δ 5.58 (ddd, 1H, J=17.2, 10.1, 7.2 Hz), 5.02 (d, 1H, J=17.2 Hz), 4.95 (dd, 1H, J=10.4, 1.3 Hz), 3.75-3.64 (m, 2H), 1.73 (s, 3H), 1.57 (s, 3H), 1.41 (s, 9H), 1.10 (d, 3H, J=6.0); $^{13}$C NMR (75 MHz, 333K, $C_6D_6$) δ 152.2, 138.6, 115, 94.4, 79.3, 75.7, 67.6, 28.5, 27.3, 26.1, 17.7; HRMS (EI+) calcd. for $C_{12}H_{20}NO_3$ $(M-CH_3)^+$ 226.1443, found 226.1446.

Example 8

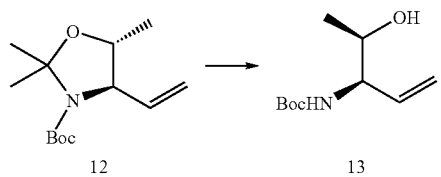

Preparation of 13. To a stirred solution of oxazolidine 12 (12.79 g, 0.0513 mol) in MeOH (530 mL) at 23° C. was added camphorsulfonic acid (392.1 mg, 1.651 mmol). After 6 h at 23° C., the reaction was quenched with saturated aqueous $NaHCO_3$ (200 mL) and most of the organic solvent was removed in vacuo. The aqueous residue was extracted with EtOAc (3×200 mL). The combined organic layers were washed with brine (200 mL) and dried over anhydrous Na$_2$SO$_4$, filtered and concentrated in vacuo. The crude residue was purified by flash chromatography (10→40% EtOAc in hexanes) on silica (300 mL) to afford alcohol 13 (10.20 g, 96%) as a colorless oil.

Data for 13: R$_f$=0.25 (40% EtOAc in hexanes); IR (neat): 3381 (O—H), 2979, 2935, 1701 (C=O), 1644, 1456, 1387, 1258, 1179, 1084 cm$^{-1}$; [α]$_D^{22}$ +12.2 (c 1.3, CHCl$_3$); $^1$H NMR (300 MHz, 333K, C$_6$D$_6$) δ 5.56 (ddd, 1H, J=17.2, 10.5, 5.6 Hz), 5.06 (ddd, 1H, J=17.2, 1.5, 1.5 Hz), 4.94 (ddd, 1H, J=10.4, 1.5, 1.5 Hz), 4.08-3.99 (m, 1H), 3.50-3.40 (m, 1H), 1.42 (s, 9H), 0.97 (d, 3H, J=6.3 Hz); $^{13}$C NMR (75 MHz, 333K, C$_6$D$_6$) δ 156.2, 137.4, 115.7, 79.1, 69.4, 59.0, 28.5, 19.9.

Example 9

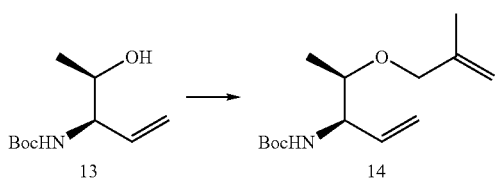

Preparation of 14. To a stirred solution of alcohol 13 (9.854 g, 0.049 mol) in DMF (50 mL) at 23° C. was added methallyl bromide (20.0 mL, 0.198 mol) under a nitrogen atmosphere. The flask was wrapped with aluminum foil and silver oxide (17.12 g, 0.0735 mol) was added at the same temperature. After 21 h at 23° C., the reaction mixture was diluted with ether (50 mL), filtered through Celite 545® and washed with additional ether (100 mL). The filtrate was then extracted with water (5×500 mL), brine (50 mL), dried over anhydrous Na$_2$SO$_4$, filtered and concentrated in vacuo. The crude residue was purified by flash chromatography (2.5→10% EtOAc in hexanes) on silica (300 mL) to afford methallyl ether 14 (10.70 g, 86%) as a colorless oil.

Data for 14: R$_f$=0.38 (10% EtOAc in hexanes); IR (neat): 3453 (N—H), 3353, 3079, 2978, 2932, 1719 (C=O), 1496, 1366, 1246, 1171, 1078 cm$^{-1}$; [α]$_D^{22}$ +34.3 (c 1.0, CHCl$_3$); $^1$H NMR (300 MHz, 293K, CDCl$_3$) δ 5.89 (ddd, 1H, J=17.2, 10.4, 5.4 Hz), 5.22 (ddd, 1H, J=17.2, 1.5, 1.5 Hz), 5.16 (ddd, 1H, J=10.4, 1.5, 1.5 Hz), 4.95-4.94 (m, 1H), 4.87-4.86 (m, 1H), 4.16-4.08 (m, 1H), 3.95 (d, 1H, J=12.3 Hz), 3.81 (d, 1H, J=12.3 Hz), 3.57 (dq, 1H, J=6.2, 2.8 Hz), 1.73 (br s, 3H), 1.46 (s, 9H), 1.17 (d, 3H, J=6.3 Hz); $^{13}$C NMR (75 MHz, 333K, C$_6$D$_6$) δ 155.7, 142.8, 137.8, 115.0, 111.9, 78.8, 76.6, 73.3, 57.4, 28.5, 19.5, 16.3; HRMS (EI+) calcd. for C$_{10}$H$_{17}$NO$_3$ (M−C$_4$H$_8$)$^+$ 199.1208, found 199.1215.

Example 10

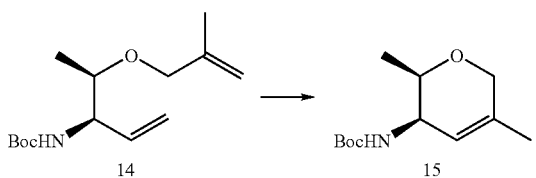

Preparation of 15. To a stirred solution of methallyl ether 14 (315.6 mg, 1.238 mmol) in benzene (13 mL) was added tricyclohexylphosphine[1,3-bis(2,4,6-trimethylphenyl)-4,5-dihydroimidazol-2-ylidene][benzylidene] ruthenium (IV) dichloride (10.5 mg, 12.4 μmol) at 23° C. under a nitrogen atmosphere. The reaction was then refluxed for 30 min. After cooling to 23° C., Pb(OAc)$_4$ (9.1 mg, 0.02 mmol) was added[5] and stirred for an additional 12 h. The solvent was then removed in vacuo and the crude residue was purified by flash chromatography (2.5→10% EtOAc in hexanes) on silica (15 mL) to afford cyclic ether 15 (275.4 mg, 98%) as a white solid.

Data for 15: m.p.=86° C.; R$_f$=0.35 (10% EtOAc in hexanes); IR (KBr): 3350 (N—H), 2981, 2932, 2916, 1702 (C=O), 1678, 1512, 1361, 1239, 1163, 1105 cm$^{-1}$; [α]$_D^{22}$ −96.3 (c 7.0, CHCl$_3$); $^1$H NMR (300 MHz, 293K, C$_6$D$_6$) δ 5.33 (dq, 1H, J=5.7, 1.5 Hz), 4.53 (d, 1H, J=9.5 Hz), 4.08-4.00 (m, 1H), 3.71-3.57 (m, 2H), 3.31 (dq, 1H, J=6.3, 2.5 Hz), 1.44 (s, 9H), 1.25 (d, 3H, J=6.4 Hz), 1.15 (m, 3H); $^{13}$C NMR (75 MHz, 293K, C$_6$D$_6$) δ 155.7, 136.4, 121.2, 78.6, 73.0, 69.4, 47.7, 28.5, 18.0, 17.0; HRMS (EI+) calcd. for C$_{12}$H$_{20}$NO$_3$ (M−H)$^+$ 226.1443, found 226.1433.

Example 11

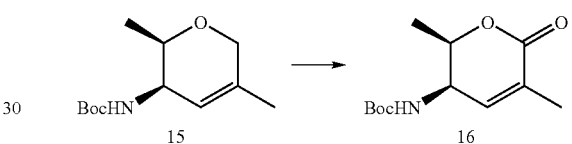

Preparation of 16. To a stirred solution of dihydropyran 15 (237.9 mg, 1.048 mmol) in 1,2-dichloroethane (6 mL) at 23° C. was added pyridinium dichromate (1.579 g, 4.196 mmol) under a nitrogen atmosphere. The resulting suspension was refluxed for 4 h. After cooling to 23° C., additional pyridinium dichromate (0.7895 g, 2.099 mmol) was added to the reaction and reflux continued (Paquette, L. A.; Schloss, J. D.; Efremov, I.; Fabris, F.; Gallou, F.; Méndez-Andino, J.; Yang, J. Org. Lett. 2000, 2, 1259-1261). After 4 h at 23° C., the reaction mixture was diluted with ether (10 mL), filtered through Celite 545®, washed with additional ether (10 mL) and the filtrate was concentrated in vacuo. The crude residue was purified by flash chromatography (7.5→30% EtOAc in hexanes) on silica (40 mL) to afford the unsaturated lactone 16 (182.2 mg, 72%) as a white solid.

Alternative procedure: To a stirred solution of dihydropyran 15 (473.1 mg, 2.084 mmol) in benzene (40 mL) at 23° C. was added Celite 545® (1.9 g), pyridinium dichromate (1.576 g, 4.190 mmol) and tert-butyl hydroperoxide (70 wt % in water, 1.2 mL, 8.7 mmol). After 5 h at 23° C., the reaction mixture was filtered through Celite 545®, washed with additional benzene (40 mL), dried over anhydrous Na$_2$SO$_4$, filtered and concentrated in vacuo. The crude residue was purified by flash chromatography (7.5→30% EtOAc in hexanes) on silica gel (30 mL) to afford the unsaturated lactone 16 (327.1 mg, 65%) as a white solid.

Data for 16: m.p.=160° C.; R$_f$=0.38 (40% EtOAc in hexanes); IR (KBr): 3374 (N—H), 2889, 2970, 2940, 1705 (C=O), 1668, 1510, 1384, 1366, 1290, 1257, 1240, 1164 cm$^{-1}$; [α]$_D^{22}$ −191.7 (c 0.5, CHCl$_3$); $^1$H NMR (300 MHz, 293K, CDCl$_3$) δ 6.64 (dq, 1H, J=6.3, 1.4 Hz), 4.61 (dq, 1H, J=6.4, 3.1 Hz), 4.60-4.55 (m, 1H), 4.30-4.22 (m, 1H), 1.95 (dd, 3H, J=1.5, 0.9 Hz), 1.45 (s, 9H), 1.38 (d, J=6.4 Hz); $^{13}$C NMR (75 MHz, 293K, CDCl$_3$) δ 165.3, 155.3, 138.1, 130.2, 80.2, 76.4, 46.1, 28.2, 16.9, 16.1; HRMS (EI+) calcd. for $C_8H_{10}NO_3$ (M–$C_4H_9O$)+ 168.0661, found 168.0662.

Example 12

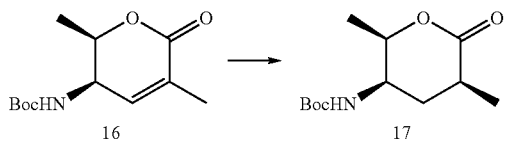

Preparation of 17: To a stirred solution of the unsaturated lactone 16 (205.8 mg, 0.8539 mmol) in ethanol (15 mL) at 23° C. was added $PtO_2$ (2.1 mg, 8.3 µmol) and the atmosphere in the reaction flask was changed to hydrogen. After 3 h at 23° C., the reaction mixture was filtered through filter paper and the solvent was removed in vacuo to afford the saturated lactone 17 (203.2 mg, 98%, dr=10:1) as a white solid.

Data for 17: m.p.=133° C.; $R_f$=0.33 (40% EtOAc in hexanes); IR (KBr): 3388 (—NH), 2984, 2974, 2939, 1731 (C=O), 1717 (C=O), 1673, 1518, 1366, 1293, 1177, 1082, 1023 cm$^{-1}$; $[\alpha]_D^{22}$ +73.4 (c 1.4, CHCl$_3$); $^1$H NMR (300 MHz, 293K, CDCl$_3$) δ 4.72 (br d, 1H, J=8.6 Hz), 4.52 (dq, 1H, J=6.4, 3.0 Hz), 4.16-4.06 (m, 1H), 2.69-2.52 (m, 2H), 1.45 (s, 9H), 1.36 (d, 3H, J=6.4 Hz), 1.22 (d, 3H, J=6.3 Hz); $^{13}$C NMR (75 MHz, 333K, C$_6$D$_6$) δ 174.5, 155.8, 79.0, 75.1, 48.2, 35.1, 32.4, 28.5, 15.9, 15.5 Hz; HRMS (EI+) calcd. for $C_{12}H_{22}NO_4$ (M+H)+ 244.1549, found 244.1548.

Example 13

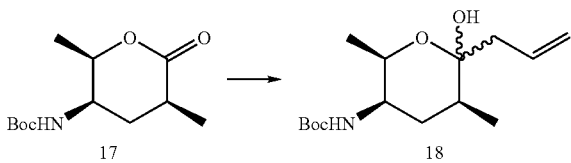

Preparation of 18: To a stirred solution of lactone 17 (1.520 g, 6.25 mmol) in THF (30 mL) at −78° C. was added allylmagnesium chloride (2.0 M solution in THF, 7.0 mL, 12 mmol) down the flask sides under a nitrogen atmosphere. After 1.5 h at the same temperature, the reaction was quenched with saturated aqueous NH$_4$Cl (25 mL) and most of the organic solvent was removed in vacuo. The aqueous residue was extracted with EtOAc (3×25 mL). The combined organic layers were washed with brine (30 mL), dried over anhydrous Na$_2$SO$_4$, filtered and concentrated in vacuo. The crude residue was purified by flash chromatography (10→50% EtOAc in hexanes) on silica (100 mL) to afford hemiketal 18 (1.712 g, 96%) as a colorless oil.

Data for 18: $R_f$=0.26 (40% EtOAc in hexanes); IR (neat): 3437 (N—H), 3391 (br O—H), 2976, 2933, 1709 (C=O), 1692 (C=O), 1641, 1510, 1366, 1170, 1050 cm$^{-1}$; $^1$H NMR (300 MHz, 293K, CDCl$_3$) δ 6.02-5.81 (m, 1H), 5.20-5.08 (m, 2H), 4.71 (br d, 1H, J=9.0 Hz), 3.73-3.67 (m, 1H), 3.40-3.33 (m, 1H), 3.30-3.27 (m, 2H), 2.78-2.70 (m, 1H), 2.27 (br d, 1H, J=7.4 Hz), 2.02-1.93 (m, 2H), 1.45 (s, 9H), 1.16 (d, 3H, J=6.3 Hz), 1.13 (d, 3H, J=7.2 Hz); $^{13}$C NMR (75 MHz, 293K, CDCl$_3$) δ 212.6, 156.3, 130.8, 118.5, 79.2, 69.1, 53.7, 46.5, 42.5, 35.7, 28.3, 20.2, 18.0; HRMS (EI+) calcd. for $C_{12}H_{22}NO_4$ (M–$C_3H_5$)+ 244.1549, found 244.1550.

Example 14

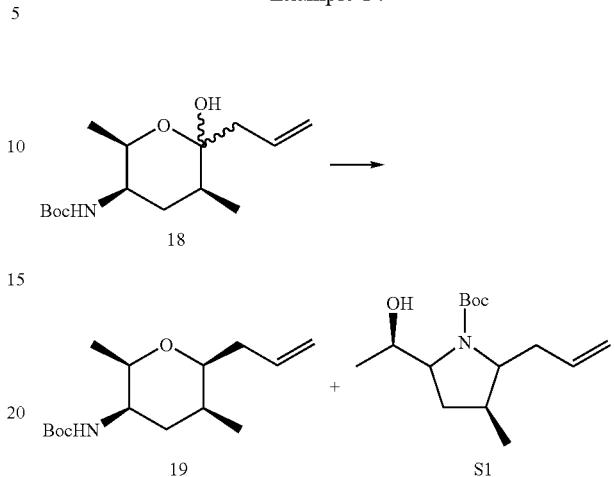

Preparation of 19: To a stirred solution of 18 (3.342 g, 11.71 mmol) in CH$_2$Cl$_2$ (50 mL) was added CF$_3$CH$_2$OH (6.8 mL, 93 mmol) and triethylsilane (18.5 mL, 116 mmol) at 23° C. under a nitrogen atmosphere. The reaction was cooled to −78° C., and BF$_3$.OEt$_2$ (5.9 mL, 47 mmol) complex was added slowly down the flask side. After an additional 3 h at the same temperature, saturated aqueous NaHCO$_3$ (50 mL) was added at −78° C., and the layers were separated. The aqueous residue was extracted with EtOAc (3×50 mL). The combined organic layers were washed with brine (75 mL), dried over anhydrous Na$_2$SO$_4$, filtered, and concentrated under reduced pressure. The resulting residue was purified by flash chromatography (2→12.5% EtOAc in hexanes) on silica gel (800 mL) to afford 19 (1.242 g, 39%) and S1 (707 mg, 22%) as colorless oils.

Data for 19: $R_f$=0.30 (10% EtOAc in hexanes); IR (neat): 3460 (N—H), 2977, 2934, 1718 (C=O), 1642, 1496, 1366, 1171, 1058 cm$^{-1}$; $[\alpha]_D^{22}$ −10.1 (c 1.2, CHCl$_3$); $^1$H NMR (300 MHz, 293K, CDCl$_3$) δ 5.80 (dddd, 1H, J=17.1, 10.2, 7.6, 6.3 Hz), 5.14-5.08 (m, 1H), 5.05 (br d, 1H, J=10.2 Hz), 4.77 (br d, 1H, J=9.1 Hz), 3.64-3.56 (m, 2H), 3.51 (ddd, J=7.4, 7.4, 2.9 Hz), 2.38-2.28 (m, 1H), 2.17-2.06 (m, 1H), 1.93-1.90 (m, 2H), 1.78-1.70 (m, 1H), 1.44 (s, 9H), 1.15 (d, 3H, J=6.3 Hz), 1.04 (d, 3H, J=7.4 Hz); $^{13}$C NMR (75 MHz, 293K, CDCl$_3$) δ 155.9, 134.8, 116.6, 80.6, 78.9, 76.3, 48.3, 37.4, 36.0, 28.8, 28.4, 17.7, 14.9; HRMS (EI+) calcd. for $C_{12}H_{22}NO_3$ (M–$C_3H_5$)+ 228.1600, found 228.1593.

Data for S1: $R_f$=0.32 (30% EtOAc in hexanes); IR (neat) 3386 (br O—H), 2974, 2931, 2868, 1692 (C=O), 1663, 1450, 1397, 1367, 1172, 1233, 1113 cm$^{-1}$; $[\alpha]_D^{22}$ +19.9 (c 1.0, CHCl$_3$); $^1$H NMR (300 MHz, 293K, CDCl$_3$) δ 5.82-5.68 (m, 1H), 5.05 (br s, 1H), 5.02-5.00 (m, 1H), 3.73 (ddd, J=7.9, 7.9, 5.9 Hz), 3.62-3.54 (m, 1H), 3.48-3.43 (ddd, J=7.4, 7.4, 2.9 Hz), 2.28 (br t, 2H), 2.05-1.97 (m, 1H), 1.75-1.64 (m, 2H), 1.62-1.51 (m, 1H), 1.48 (s, 9H), 1.09 (d, 3H, J=6.1 Hz), 0.95 (d, 3H, J=6.8 Hz); $^{13}$C NMR (75 MHz, 293K, C$_6$D$_6$) δ 158.1, 135.2, 117.2, 80.1, 72.7, 65.7, 64.8, 39.0, 35.7, 34.9, 28.4, 21.3, 18.9; HRMS (EI+) calcd. for $C_{12}H_{22}NO_3$ (M–$C_3H_5$)+ 228.1600, found 228.1598.

Example 15

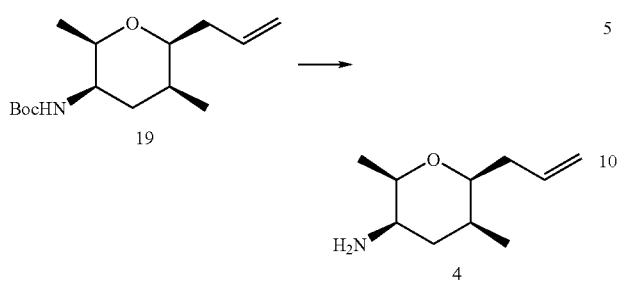

Preparation of 4: To the Boc-protected amine 19 (179.6 mg, 0.6677 mmol) at 0° C. was added 10 mL of 10% TFA in CH$_2$Cl$_2$. The reaction was slowly warmed to 23° C. and stirred for 3 h. Removal of the solvent in vacuo gave amine 4 as a dark brown residue. This crude material was used in the next step without further purification.

Example 16

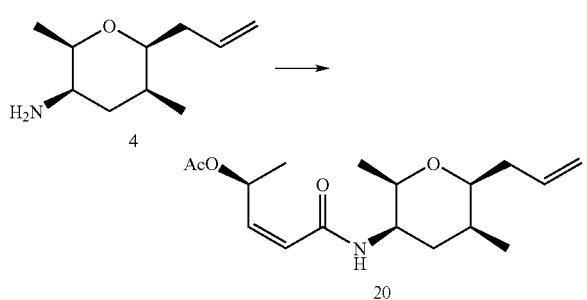

Preparation of 20: To a stirred solution of acid 3 (127 mg, 0.804 mmol) in CH$_3$CN (4 mL) at 23° C. was added O-(7-azabenzotriazol-1-yl)-N,N,N',N'-tetramethyluronium hexafluorophoshate (305 mg, 0.804 mmol), followed by N,N-diisopropylethylamine (470 µL, 2.70 mmol) under a nitrogen atmosphere. The resulting mixture was then transferred by cannula to a stirred solution of amine 4 in CH$_3$CN (5 mL) at the same temperature and rinsed with additional CH$_3$CN (1 mL). After 12 h at 23° C., the reaction was quenched with saturated aqueous NH$_4$Cl (5 mL) and most of the organic solvent was removed in vacuo. The aqueous residue was extracted with EtOAc (3×10 mL). The combined organic layers were washed with brine (10 mL), dried over anhydrous Na$_2$SO$_4$, filtered and concentrated in vacuo. The crude residue was purified by flash chromatography (7.5→30% EtOAc in hexanes) on silica (12 mL) to afford amide 20 (178 mg, 86%) as a colorless oil.

Data for 20: R$_f$=0.45 (40% EtOAc in hexanes); IR (neat): 3365 (N—H), 2977, 2935, 1739 (C=O), 1669 (C=O), 1640, 1516, 1369, 1243, 1050, 1010 cm$^{-1}$; [α]$_D^{22}$ −64.2 (c 2.3, CHCl$_3$); $^1$H NMR (300 MHz, 293K, CDCl$_3$) δ 6.29-6.22 (m, 1H), 5.98 (br d, 1H, J=8.8 Hz), 5.90 (dd, 1H, J=11.6, 7.8 Hz), 5.84-5.74 (m, 1H), 5.70 (dd, 1H, J=11.6, 1.0 Hz), 5.15-5.03 (m, 2H), 3.98-3.92 (m, 1H), 3.67 (dq, 1H, J=6.5, 2.2 Hz), 3.54 (ddd, 1H, J=7.2, 7.2, 2.7 Hz), 2.39-2.29 (m, 1H), 2.17-2.07 (m, 1H), 2.04 (s, 3H), 1.97-1.94 (m, 2H), 1.83-1.75 (m, 1H), 1.39 (d, 3H, J=6.5 Hz), 1.15 (d, 3H, J=6.5 Hz), 1.02 (d, 3H, J=7.4 Hz); $^{13}$C NMR (75 MHz, 293K, CDCl$_3$) δ 170.3, 164.8, 143.6, 134.6, 122.4, 116.7, 80.7, 75.9, 68.8, 47.0, 37.3, 35.8, 28.7, 21.2, 19.9, 17.8, 14.9; HRMS (EI+) calcd. for C$_{17}$H$_{27}$NO$_4$ (M+H)$^+$ 310.2018, found 310.2007.

Example 17

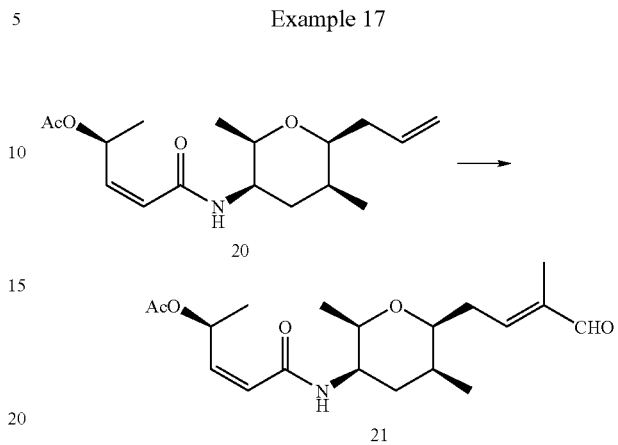

Preparation of 21: To a stirred solution of alkene 20 (103 mg, 0.332 mmol) in CH$_2$Cl$_2$ (1.5 mL) at 23° C. was added methacrolein (550 µL, 6.65 mmol), followed by Grela's catalyst (18 mg, 27 µmol), under a nitrogen atmosphere. After 9 h at 23° C., the solvent was removed in vacuo and the crude residue was purified by flash chromatography (15→60% EtOAc in hexanes) on silica (8 mL) to afford aldehyde 21 (78 mg, 67%) as a white solid.

Data for 21: R$_f$=0.29 (60% EtOAc in hexanes); IR (neat): 3363 (N—H), 2919, 2851, 1734 (C=O), 1670 (C=O), 1639, 1520, 1458, 1244, 1011 cm$^{-1}$; $^1$H NMR (300 MHz, 293K, CDCl$_3$) δ 9.42 (s, 1H), 6.58-6.52 (m, 1H), 6.27-6.18 (m, 1H), 6.06 (br d, 1H, J=8.4 Hz), 5.89 (dd, 1H, J=11.6, 7.8 Hz), 5.73 (dd, 1H, J=11.5, 0.8 Hz), 3.99-3.95 (m, 1H), 3.74-3.64 (m, 2H), 2.62-2.52 (m, 1H), 2.46-2.36 (m, 1H), 2.05 (s, 3H), 2.02-1.98 (m, 2H), 1.84-1.79 (m, 2H), 1.76 (br s, 3H), 1.39 (d, 3H, J=6.5 Hz), 1.16 (d, 1H, J=6.4 Hz), 1.06 (d, 3H, J=7.3 Hz); $^{13}$C NMR (75 MHz, 293K, CDCl$_3$) δ 195.0, 170.4, 164.9, 150.4, 143.4, 140.5, 122.5, 79.7, 76.0, 68.8, 46.8, 35.7, 32.7, 29.4, 21.2, 19.9, 17.7, 15.0, 9.4; HRMS (EI+) calcd. for C$_{19}$H$_{29}$NO$_5$ (M$^+$) 351.2046, found 351.2041.

Example 18

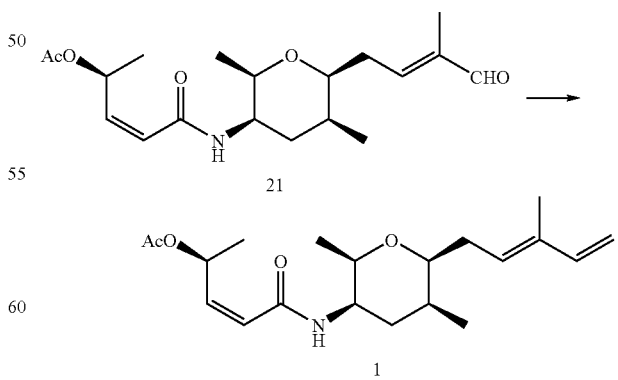

Preparation of 1: To a stirred suspension of methyltriphenylphosphonium bromide (174.6 mg, 0.4887 mmol) in THF (1.1 mL) at 0° C. was added KO$^t$Bu (50.8 mg, 0.453 mmol)

under a nitrogen atmosphere. After 30 min, aldehyde 21 (120.8 mg, 0.3440 mmol) in THF (0.6 mL) was added dropwise by cannula at the same temperature and rinsed with additional THF (0.2 mL). After 2 h at 23° C., the reaction was quenched with saturated aqueous NH₄Cl (3 mL) and most of the solvent was removed in vacuo. The aqueous residue was extracted with EtOAc (3×5 mL). The combined organic layers were washed with brine (5 mL), dried over anhydrous Na₂SO₄, filtered and concentrated in vacuo. The crude residue was purified by flash chromatography (5→20% EtOAc in hexanes) on silica (8 mL) to afford the terminal alkene 1 (108.4 mg, 90%) as a colorless oil.

Data for 1: $R_f$=0.45 (40% EtOAc in hexanes); IR (neat): 3363 (N—H), 2976, 2934, 1738 (C=O), 1669 (C=O), 1637, 1518, 1369, 1243, 1049, 1010 cm$^{-1}$; $[\alpha]_D^{22}$ −63.6 (c 2.4, CHCl₃); ¹H NMR (300 MHz, 293K, CDCl₃) δ 6.38 (dd, 1H, J=17.4, 10.7 Hz), 6.30-6.20 (m, 1H), 6.01 (br d, 1H, J=9.0 Hz), 5.90 (dd, 1H, J=11.6, 7.8 Hz), 5.71 (dd, 1H, J=11.6, 1.2 Hz), 5.47 (br t, 1H, J=7.1 Hz), 5.11 (d, 1H, J=17.4 Hz), 4.96 (d, 1H, J=10.7 Hz), 3.97-3.90 (m, 1H), 3.68 (dq, 1H, J=6.5, 2.2 Hz), 3.54 (ddd, 1H, J=7.3, 7.3, 2.7 Hz), 2.43-2.33 (m, 1H), 2.31-2.19 (m, 1H), 2.05 (s, 3H), 1.97-1.93 (m, 2H), 1.82-1.76 (m, 1H), 1.76 (s, 3H), 1.40 (d, 3H, J=6.5 Hz), 1.16 (d, 3H, J=6.5 Hz), 1.03 (d, 3H, J=7.3 Hz); ¹³C NMR (75 MHz, 293K, CDCl₃) δ 170.3, 164.8, 143.5, 141.2, 135.6, 128.0, 122.4, 111.0, 80.7, 75.9, 68.8, 47.0, 35.8, 31.8, 28.8, 21.2, 19.9, 17.8, 15.0, 11.9; HRMS (EI+) calcd. for C₂₀H₃₁NO₄ (M⁺) 349.2253, found 349.2251.

Example 19

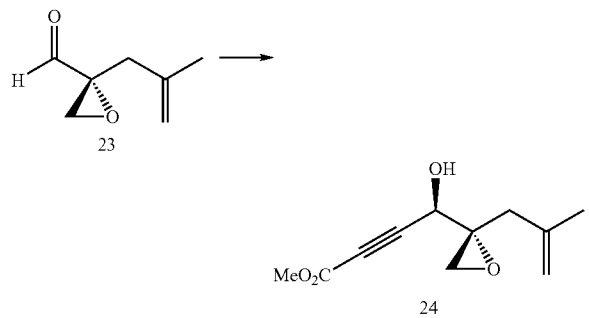

Preparation of and data for 24: See Shahi, S. P.; Koide, K. *Angew. Chem., Int. Ed.* 2004, 43, 2525.

Example 20

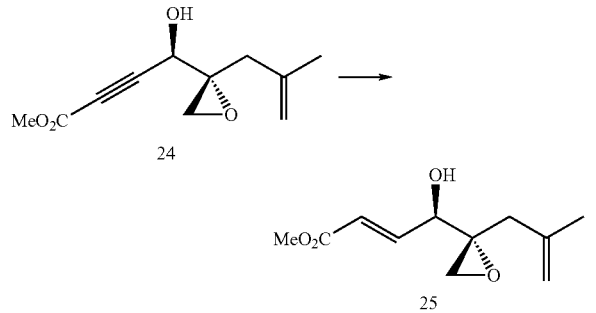

Preparation of and data for 25: See Meta, C. T.; Koide, K. *Org. Lett.* 2004, 6, 1785.

Example 21

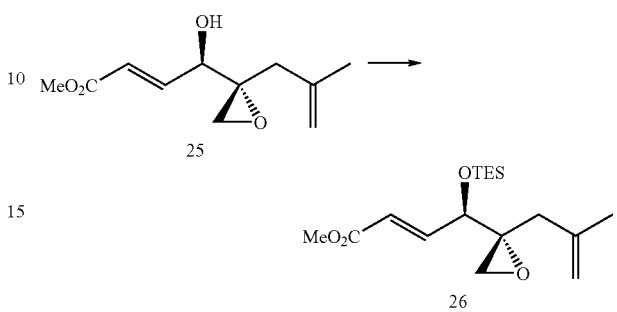

Preparation of 26: To a stirred solution of imidazole (1.02 g, 15.0 mmol) in THF (20 mL) was added chlorotriethylsilane (2.35 mL, 14.0 mmol), followed by the dropwise addition of alcohol 25 (2.11 g, 9.96 mmol) in THF (3 mL), and then the container that initially contained 25 was rinsed with THF (2×1 mL) and added to the reaction mixture at 0° C. under a nitrogen atmosphere. After an additional 45 min at the same temperature, H₂O (50 mL) was added, and most of the THF was removed under reduced pressure. The aqueous residue was extracted with Et₂O (2×40 mL). The combined organic layers were washed with brine (50 mL), dried over anhydrous Na₂SO₄, filtered, and concentrated under reduced pressure. The resulting residue was purified by flash chromatography (1.5→3% EtOAc in hexanes) on silica gel (150 mL) to afford 26 (3.27 g, quantitative yield) as a colorless oil.

Data for 26: $R_f$=0.30 (10% EtOAc in hexanes); IR (neat): 2954, 1728 (C=O), 1281, 1167, 978, 744 cm$^{-1}$; $[\alpha]_D^{22}$ +9.9 (c 1.1, CHCl₃); ¹H NMR (300 MHz, 293K, CDCl₃) δ 6.94 (dd, 1H, J=15.5, 4.6 Hz), 6.10 (dd, 1H, J=15.5, 1.8 Hz), 4.85-4.84 (m, 1H), 4.73-4.71 (m, 1H), 4.13 (dd, 1H, J=4.6, 1.8 Hz), 3.77 (s, 3H), 2.75 (br d, 1H, J=4.8 Hz), 2.71 (d, 1H, J=4.8 Hz), 2.46 (br d, 1H, J=14.5 Hz), 2.35 (br d, 1H, J=14.5 Hz), 1.72 (br s, 3H), 0.97 (q, 9H, J=7.9 Hz), 0.64 (q, 6H, J=7.9 Hz); ¹³C NMR (75 MHz, 293K, C₆D₆) 166.3, 147.2, 141.0, 121.8, 114.7, 76.8, 60.1, 51.2, 48.4, 36.2, 23.7, 7.0, 5.0; HRMS (ESI+) calcd. for C₁₇H₃₀O₄SiNa (M+Na)⁺ 349.1811, found 349.1794.

Example 22

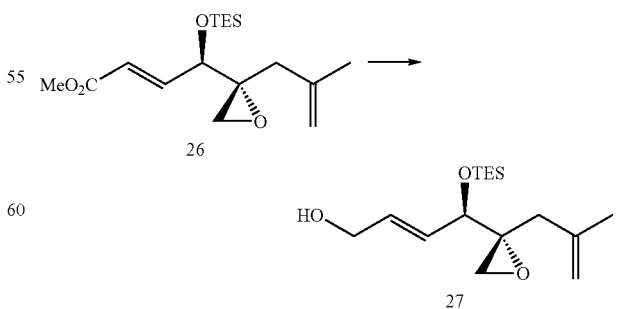

Preparation of 27: To a stirred solution of enoate 26 (968 mg, 2.96 mmol) in THF (10 mL) was added DIBAL-H (1 M in hexanes, 8.9 mL) slowly down the flask side at −78° C. under a nitrogen atmosphere. After an additional 1 h at the same temperature, saturated aqueous NH$_4$Cl (5 mL) was added at −78° C., and the reaction mixture was allowed to warm to 23° C. After an additional 1.5 h at the same temperature, the reaction mixture was diluted with Et$_2$O (15 mL), dried over anhydrous Na$_2$SO$_4$, filtered through a pad of Celite 545®, rinsed with Et$_2$O (3×25 mL), and concentrated under reduced pressure. The resulting residue was purified by flash chromatography (5→20% EtOAc in hexanes) on silica gel (40 mL) to afford 27 (838 mg, 95%) as a colorless oil.

Data for 27: R$_f$=0.23 (20% EtOAc in hexanes); IR (neat): 3421 (br, O—H), 2955, 1458, 1124, 1096, 1005, 972, 743; [α]$_D^{22}$ −13.4 (c 1.0, CHCl$_3$); $^1$H NMR (300 MHz, 293K, CDCl$_3$) δ 5.89 (dddd, 1H, J=15.5, 5.2, 5.2, 1.1 Hz), 5.74 (dddd, 1H J=15.5, 5.9, 1.3, 1.3 Hz), 4.84-4.83 (m, 1H), 4.74-4.73 (m, 1H), 4.19 (br app t, 2H, J=5.0 Hz), 4.07 (dd, 1H, J=5.9, 1.1 Hz), 2.80 (br d, 1H, J=5.0 Hz), 2.67 (br d, 1H, J=5.0 Hz), 2.55 (br d, 1H, J=14.5 Hz), 2.27 (br d, 1H, J=14.5 Hz), 1.75 (br s, 3H), 0.96 (t, 9H, J=7.9 Hz), 0.62 (q, 6H, J=7.9 Hz); $^{13}$C NMR (75 MHz, 293K, C$_6$D$_6$) δ 141.7, 131.6, 129.8, 114.3, 76.5, 62.6, 60.9, 48.8, 37.3, 23.8, 7.1, 5.3; HRMS (ESI+) calcd. for C$_{16}$H$_{30}$O$_3$SiNa(M+Na)$^+$ 321.1862, found 321.1850.

Example 23

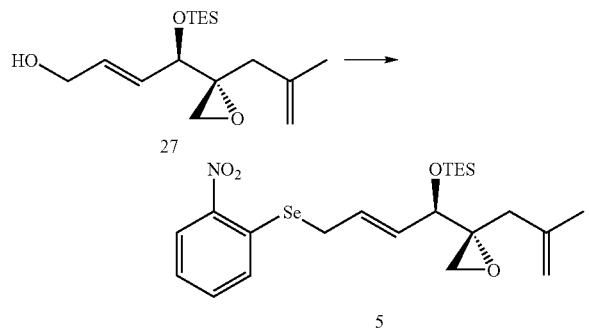

Preparation of 5: To a stirred solution of 2-nitrophenyl selenocyanate (1.10 g, 4.82 mmol) in THF (7 mL) was added 27 (1.20 g, 4.02 mmol) in THF (4 mL), and then the flask that initially contained 27 was rinsed with THF (2×1 mL) and added to the reaction mixture followed by the dropwise addition of freshly distilled $^n$Bu$_3$P (1.4 mL, 5.6 mmol) at 0° C. under a nitrogen atmosphere. After 30 min at the same temperature, the reaction mixture was poured onto saturated aqueous NaHCO$_3$ (125 mL). The layers were separated, and the aqueous residue was extracted with Et$_2$O (3×65 mL). The combined organic layers were washed with brine (75 mL), dried over anhydrous Na$_2$SO$_4$, filtered, and concentrated under reduced pressure. The resulting residue was purified by flash chromatography (1→5% EtOAc in hexanes) on silica gel (100 mL) to afford 5 (2.06 g, quantitative yield) as a pale yellow oil.

Data for 5: R$_f$=0.20 (10% EtOAc in hexanes); IR (neat): 2954, 1516, 1332, 1304, 1100, 970, 730; [α]$_D^{22}$ −24.0 (c 1.0, CHCl$_3$); $^1$H NMR (300 MHz, 293K, CDCl$_3$) δ 8.29 (dd, 1H, J=7.9, 1.2 Hz), 7.56-7.50 (m, 2H), 7.33 (ddd, 1H, J=8.4, 5.3, 3.2 Hz), 5.92-5.74 (m, 2H), 4.82 (br s, 1H), 4.67 (br s, 1H), 4.05 (br d, 1H, J=5.8 Hz), 3.69-3.59 (m, 2H), 2.79 (br d, 1H, J=5.1 Hz), 2.63 (d, 1H, J=5.1 Hz), 2.43 (d, 1H, J=14.5 Hz), 2.16 (d, 1H, J=14.5 Hz), 1.70 (br s, 3H), 0.92 (t, 9H, J=7.9 Hz), 0.57 (q, 6H, J=7.9 Hz); $^{13}$C NMR (75 MHz, 293K, CDCl$_3$) δ 146.9, 141.0, 133.9, 133.5, 133.2, 129.3, 126.3, 126.1, 125.5, 114.1, 74.3, 60.6, 49.1, 38.1, 27.7, 23.4, 6.7, 4.8; HRMS (ESI+) calcd. for C$_{22}$H$_{33}$NO$_4$SeSiNa(M+Na)$^+$ 506.1242, found 506.1229.

Example 24

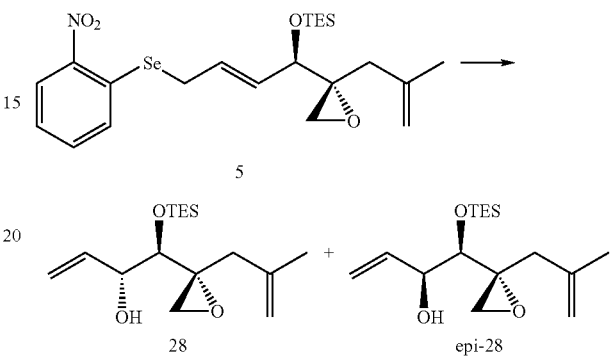

Preparation of 28: To a stirred solution of 5 (120 mg, 0.249 mmol) in THF (1.25 mL) was added DMAP (152 mg, 1.24 mmol) followed by the dropwise addition of aqueous H$_2$O$_2$ (30% v/v, 250 μL) at −44° C. under an open atmosphere. The reaction was slowly warmed to 23° C. After a total of 12 h, the reaction mixture was diluted with Et$_2$O (5 mL) at 23° C., dried over anhydrous Na$_2$SO$_4$, filtered, and concentrated under reduced pressure. The resulting residue was purified by flash chromatography (2.5→7.5% EtOAc in hexanes) on silica gel (8 mL) to afford a 7.5:1 mixture of 28 and epi-28 (70.4 mg, 95%). For characterization and subsequent synthetic steps, 28 and epi-28 were separated by column chromatography.

Data for 28: R$_f$=0.24 (10% EtOAc in hexanes); IR (neat): 3471 (br, O—H), 2955, 1648, 1459, 1239, 1112, 1007, 917, 895, 743; [α]$_D^{25}$+6.0 (c 1.0, CHCl$_3$); $^1$H NMR (300 MHz, 293K, C$_6$D$_6$) δ 5.89 (ddd, 1H, J=17.2, 10.5, 5.6 Hz), 5.27 (ddd, 1H, J=17.2, 1.6, 1.6 Hz), 5.04 (ddd, 1H, J=10.5, 1.6, 1.6 Hz), 4.86-4.83 (m, 1H), 4.81-4.78 (m, 1H), 4.04 (ddddd, 1H, J=7.1, 5.6, 3.6, 1.6, 1.6 Hz), 3.22 (d, 1H, J=7.1 Hz), 2.70 (d, 1H, J=14.2 Hz), 2.64 (d, 1H, J=4.9 Hz), 2.62 (d, 1H, J=14.2 Hz), 2.47 (d, 1H, J=4.9 Hz), 1.79 (br s, 3H), 1.58 (d, 1H, J=3.6 Hz), 1.02 (t, 9H, J=7.9 Hz), 0.75-0.65 (m, 6H); $^{13}$C NMR (75 MHz, 293K, C$_6$D$_6$) δ 141.8, 138.6, 115.7, 114.6, 80.8, 74.5, 59.3, 50.2, 36.7, 24.2, 7.1, 5.3; HRMS (EI+) calcd. for C$_{13}$H$_{25}$O$_2$Si (M−C$_3$H$_5$O)$^+$ 241.1624, found 241.1624.

Data for epi-28: R$_f$=0.31 (10% EtOAc in hexanes); IR (neat): 3502 (br, O—H), 2955, 1649, 1458, 1240, 1092, 1053, 1006, 927, 744; [α]$_D^{25}$−7.5 (c 1.0, CHCl$_3$); $^1$H NMR (300 MHz, 293K, C$_6$D$_6$) δ 5.69 (ddd, 1H, J=17.1, 10.5, 5.6 Hz), 5.37 (ddd, 1H, J=17.1, 1.6, 1.6 Hz), 5.02 (ddd, 1H, J=10.5, 1.9, 1.5 Hz), 4.83-4.80 (m, 1H), 4.69-4.67 (m, 1H), 4.12-4.06 (m, 1H), 3.18 (d, 1H, J=6.4 Hz), 2.62 (d, 1H, J=14.4 Hz), 2.51 (d, 1H, J=14.4 Hz), 2.50 (d, 1H, J=4.7 Hz), 2.44 (d, 1H, J=4.2 Hz). 2.24 (d, 1H, J=4.7 Hz), 1.73 (br s, 3H), 1.01 (t, 9H, J=7.9 Hz), 0.75-0.65 (m, 6H); $^{13}$C NMR (75 MHz, 293K, C$_6$D$_6$) δ 141.2, 137.9, 116.1, 115.0, 81.8, 73.9, 59.3, 49.5, 36.2, 24.2, 7.1, 5.3.

Example 25

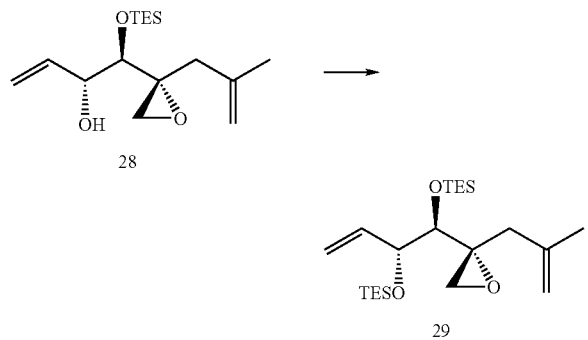

Preparation of 29: To a stirred solution of imidazole (218 mg, 3.20 mmol) in THF (3 mL) was added chlorotriethylsilane (470 µL, 2.80 mmol), followed by the dropwise addition of alcohol 28 (596 mg, 2.00 mmol) in THF (1 mL), and then the container that initially contained 28 was rinsed with THF (2×0.5 mL) and added to the reaction mixture, at 0° C. under a nitrogen atmosphere. After an additional 1.5 h at the same temperature, $H_2O$ (14 mL) was added, and most of the THF was removed under reduced pressure. The aqueous residue was extracted with $Et_2O$ (2×20 mL). The combined organic layers were washed with brine (20 mL), dried over anhydrous $Na_2SO_4$, filtered, and concentrated under reduced pressure. The resulting residue was purified by flash chromatography (1.5→3% EtOAc in hexanes) on silica gel (40 mL) to afford 29 (786 mg, 95%) as a colorless oil.

Data for 29: $R_f$=0.65 (5% EtOAc in hexanes); IR (neat): 2955, 1648, 1458, 1239, 1100, 1006, 788, 744; $[\alpha]_D^{22}$ −10.0 (c 1.0, $CHCl_3$); $^1$H NMR (300 MHz, 293K, $CDCl_3$) δ 5.80 (ddd, 1H, J=17.3, 10.2, 7.2 Hz), 5.23 (br ddd, 1H, J=17.3, 1.0, 1.0 Hz), 5.16 (br dd, J=10.2, 1.0 Hz), 4.85-4.83 (m, 1H), 4.69 (br s, 1H), 4.09 (br dd, 1H, J=7.2, 7.2 Hz), 3.21 (d, 1H, J=7.2 Hz), 2.72 (d, 1H, J=5.0 Hz), 2.69 (d, 1H, J=5.0 Hz), 2.58 (app s, 2H), 1.75 (br s, 3H), 0.96 (t, 9H, J=7.8 Hz), 0.95 (t, 9H, J=7.9 Hz), 0.67-0.55 (m, 12H); $^{13}$C NMR (75 MHz, 293K, $CDCl_3$) δ 141.3, 139.4, 116.9, 114.3, 80.6, 76.2, 59.4, 49.9, 35.6, 24.1, 6.9, 6.8, 5.2, 5.0; HRMS (EI+) calcd. for $C_{22}H_{44}O_3Si_2$ (M)$^+$ 412.2829, found 412.2841.

Example 26

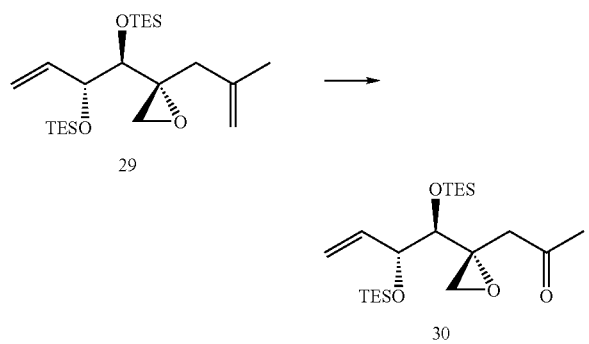

Preparation of 30: To a stirred solution of 29 (412 mg, 0.998 mmol) in $THF/H_2O$ (10:1, 4.4 mL) was added NMO·$H_2O$ (129 mg, 0.954 mmol) in one portion, followed by the addition of $OsO_4$ (2.5 mg, 9.8 µmol) at 0° C. under an open atmosphere. After 5 min at the same temperature, the reaction was warmed to 23° C. After an additional 18 h at the same temperature, the reaction mixture was diluted with $Et_2O$ (2 mL), saturated aqueous $Na_2SO_3$ (10 mL), and saturated aqueous $NaHCO_3$ (1 mL). After 30 min of vigorous stirring, the mixture was extracted with $Et_2O$ (3×15 mL). The combined organic layers were washed with saturated aqueous $Na_2SO_3$ (10 mL), then aqueous 0.1 N HCl (12 mL), dried over anhydrous $Na_2SO_4$, filtered, and concentrated under reduced pressure. The resulting crude material (477 mg) was taken to the next step without further purification: $R_f$=0.24 (20% EtOAc in hexanes).

To a solution of the crude tan oil (471 mg) in benzene (5 mL) was added Pb(OAc)$_4$ (534 mg, 1.20 mmol) in one portion at 0° C. under an open atmosphere. After 3 min at the same temperature, the reaction was warmed to 23° C. After an additional 17 min at the same temperature, the reaction mixture was diluted with $Et_2O$ (5 mL), filtered through a pad of Celite 5450®, rinsed with $Et_2O$ (4×10 mL), and concentrated under reduced pressure. The resulting residue was purified by flash chromatography (1.25→5% EtOAc in hexanes) on silica gel (25 mL) to return diene 29 (74 mg) and afford 30 (293 mg, 71%; 86% BORSM) as a colorless oil.

Data for 30: $R_f$=0.23 (5% EtOAc in hexanes); IR (neat): 2913, 1717 (C=O), 1415, 1239, 1100, 1006, 742; $[\alpha]_D^{22}$ −19.2 (c 1.0, $CHCl_3$); $^1$H NMR (300 MHz, 293K, $C_6D_6$) δ 5.81 (ddd, 1H, J=17.4, 10.3, 7.3 Hz), 5.14 (ddd, 1H, J=17.2, 1.7, 1.0 Hz), 4.98 (ddd, 1H, J=10.3, 1.8, 0.8 Hz), 4.06 (br dd, 1H, J=7.2, 6.5 Hz), 3.20 (d, 1H, J=6.5 Hz), 2.93 (d, 1H, J=14.2 Hz), 2.83 (d, 1H, J=4.5 Hz), 2.77 (d, 1H, J=14.2 Hz), 2.66 (d, 1H, J=4.5 Hz), 1.93 (s, 3H), 1.06 (t, 9H, J=7.9 Hz), 0.99 (t, 9H, J=8.0 Hz), 0.78-0.70 (m, 6H), 0.66-0.58 (m, 6H); $^{13}$C NMR (75 MHz, 293K, $C_6D_6$) δ 204.1, 139.5, 117.0, 81.5, 76.9, 57.6, 51.0, 42.5, 31.5, 7.2, 7.1, 5.4, 5.4; HRMS (ESI+) calcd. for $C_{21}H_{42}O_4Si_2Na$ (M+Na)$^+$ 437.2519, found 437.2533.

Example 27

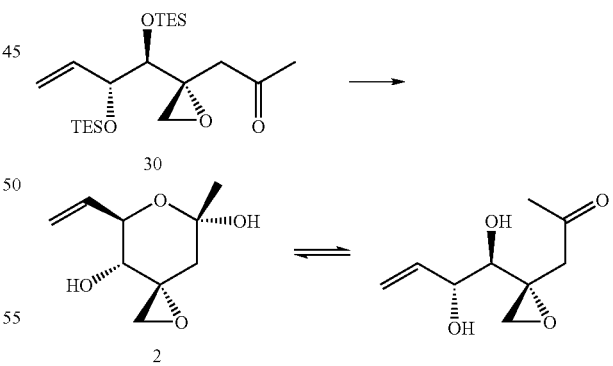

Preparation of 2: To a flask containing 30 (104 mg, 0.251 mmol) was added $AcOH/THF/H_2O$ (3:3:1 v/v/v, 2.8 mL) at 0° C. under an open atmosphere. After 10 min at the same temperature, the reaction was warmed to 23° C. After an additional 30 h at the same temperature the reaction was diluted with toluene (5 mL), and then concentrated under reduced pressure. The resulting residue was purified by flash chromatography (20→50% EtOAc in hexanes) on silica gel (6 mL) to afford 2 (42.5 mg, 91%) as a colorless oil.

Data for 2: $R_f$=0.15 (60% EtOAc in hexanes); IR (neat): 3384, 2923, 1701 (C=O, weak), 1647, 1412, 1212, 1182, 1085, 1021, 907, 819, 730; $[\alpha]_D^{22}$ +54.4 (c 0.5, $CH_2Cl_2$); $^1$H NMR (300 MHz, 293K, $CD_2Cl_2$) δ 5.97 (ddd, 1H, J=17.3, 10.5, 6.1 Hz), 5.38 (ddd, 1H, J=17.3, 1.8, 1.4 Hz), 5.25 (ddd, 1H, J=10.5, 1.8, 1.4 Hz), 4.19 (dddd, 1H, J=9.8, 6.1, 1.4, 1.2 Hz), 3.54 (app t, 1H, J=10.1 Hz), 3.31 (br s, 1H), 3.06 (d, 1H, J=4.4 Hz), 2.55 (d, 1H, J=4.4 Hz), 2.33 (d, 1H, J=14.4 Hz), 1.64 (d, 1H, J=14.4 Hz), 1.43 (s, 3H); $^{13}$C NMR (75 MHz, 293K, $CD_2Cl_2$) δ 136.4, 117.6, 96.7, 73.7, 67.9, 58.1, 48.0, 41.9, 29.1; HRMS (EI+) calcd. for $C_9H_{12}O_3$ $(M-H_2O)^+$ 168.0786, found 168.0790.

The relative stereochemistry of 28 was determined by $^1$H NMR spectrum analysis. The C4-C5 coupling constant was determined to be 9.8 Hz, indicating a diaxial arrangement.

Example 28

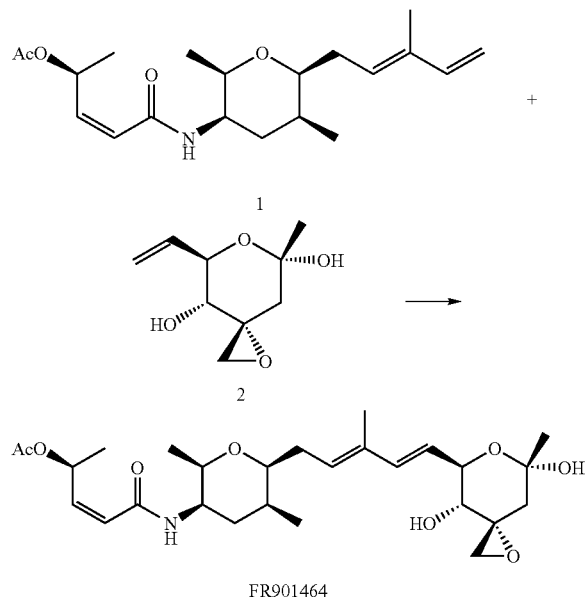

Synthesis of FR901464. A solution of 2 (33.6 mg, 0.180 mmol) was prepared in $ClCH_2CH_2Cl$ (200 μL) at 23° C. under an open atmosphere. To a stirred solution of 1 (35.1 mg, 0.100 mmol) in $ClCH_2CH_2Cl$ (100 μL) was added the solution of 2 (50 μL), followed by 22 (1.7 mg, 2.5 μmol) at 23° C. under an open atmosphere. After 1.5 h at the same temperature, additional 22 (1.7 mg, 2.5 μmol) and 2 (50 μL) were added. This addition process was repeated after 3.5 and 6.0 h after the reaction was initiated. After 10 total hours, the reaction was concentrated under reduced pressure. The resulting residue was purified by flash chromatography (10→90% EtOAc in hexanes) on silica gel (8 mL) to give 1 (24.2 mg, 69%), 2 (11.7 mg, 35%), and FR901464 (14.4 mg, 28%) as pale tan oils.

To a stirred solution of recovered 1 (24.2 mg, 0.0690 mmol) and recovered 2 (11.7 mg, 0.0628 mmol) in $ClCH_2CH_2Cl$ (200 μL) was added 22 (4.3 mg, 6.3 μmol) at 23° C. under an open atmosphere. After an additional 11 h at the same temperature, the reaction was concentrated under reduced pressure. The resulting residue was purified by flash chromatography (10→90% EtOAc in hexanes) on silica gel (5 mL) to give 1 (7.8 mg, 32%) and FR901464 (5.7 mg, 18%) as pale tan oils. The combined yield of FR901464 after one cycle is 20.1 mg (40%).

Data for FR901464 were consistent with the literature (Nakajima, H.; Takase, S.; Terano, H.; Tanaka, H. *J. Antibiot.* 1997, 50, 96 and Thompson, C. F.; Jamison, T. F.; Jacobsen, E. N. *J. Am. Chem. Soc.* 2001, 123, 9974). See $^1$H NMR and $^{13}$C NMR on pages S61-S66. The crude reaction mixture and an authentic sample of FR901464 were compared by HPLC (see pages S67-S68). (Varian Chrompack Microsorb 100 C18 column (5 μm packing; 2 mm×250 mm); 5→95% MeCN (0.05% formic acid) in $H_2O$ (0.1% formic acid); 0.8 mL/min; 237 nm.)

Example 29

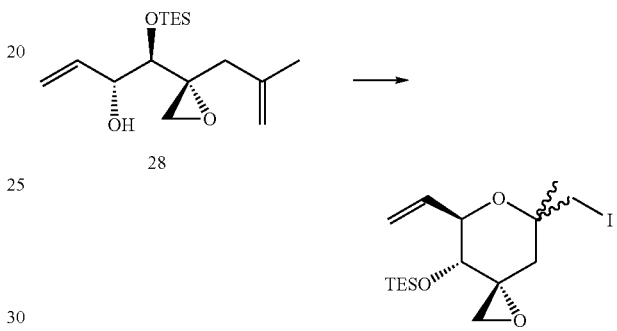

Preparation of P01. To a stirred solution of 28 (299 mg, 1.00 mmol) in 1,2-dimethoxyethane (10 mL) was added NaI (301 mg, 2.01 mmol) in one portion followed by $Pb(OAc)_4$ (799 mg, 1.80 mmol) in one portion at −40° C. under a nitrogen atmosphere. After an additional 15 min at the same temperature, the reaction mixture was warmed to 0° C. After an additional 2.3 h at the same temperature, the reaction mixture was poured onto aqueous 0.9 N HCl (100 mL) and $Et_2O$ (40 mL), and the layers were separated. The aqueous residue was extracted with $Et_2O$ (2×40 mL). The combined organic layers were washed with saturated aqueous $Na_2SO_3$ (50 mL) then brine (50 mL), dried over anhydrous $Na_2SO_4$, filtered, and concentrated under reduced pressure. The resulting residue was purified by flash chromatography (2→8% EtOAc in hexanes) on silica gel (30 mL) to recover diene 28 (50.8 mg) and afford P01 (325 mg, 77%; 92% BORSM; dr=1.2:1) as a pale yellow oil.

Example 30

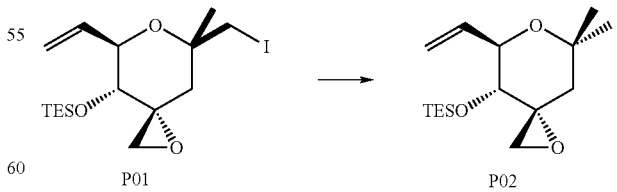

Preparation of P02. To a stirred solution of P01 (106 mg, 0.250 mmol) in toluene (5 mL) was added tributyltin hydride (330 μL, 4.92 mmol) followed by AIBN (20.6 mg, 0.125 mmol) in one portion at 23° C. under an open atmosphere. The reaction mixture was then warmed to 90° C. After 5 h at the same temperature, the reaction was cooled to 23° C. and concentrated under reduced pressure. The resulting residue was purified by flash chromatography (2→8% EtOAc in hexanes) on silica gel (20 mL) to afford P02 (47.2 mg, 63%) as a colorless oil.

Data for P02: $R_f$=0.xx (10% EtOAc in hexanes); IR (neat): 2956, 1460, 1227, 1133, 1008, 841, 742; $[\alpha]_D^{26}$ +71.2 (c 1.0, CHCl$_3$); $^1$H NMR (300 MHz, 293K, CDCl$_3$) δ 5.89 (ddd 1H, J=17.2, 10.3, 6.8 Hz), 5.41 (ddd, 1H, J=17.2, 1.8, 1.1 Hz), 5.25 (ddd, 1H, J=10.3, 1.8, 0.8 Hz), 4.16 (br dd, 1H, J=9.3, 6.8 Hz), 3.65 (d, 1H, J=9.3 Hz), 2.92 (d, 1H, J=5.1 Hz), 2.45 (d, 1H, J=5.1 Hz), 2.12 (d, 1H, J=13.9 Hz), 1.43 (s, 3H), 1.39 (d, 1H, 13.9 Hz), 1.27 (s, 3H), 0.95 (t, 9H, J=7.9 Hz), 0.61 (q, 6H, J=7.9 Hz); $^{13}$C NMR (75 MHz, 293K, C$_6$D$_6$) δ 137.6, 116.8, 74.5, 73.1, 71.4, 57.9, 47.3, 43.7, 31.3, 24.1, 7.2, 7.1, 5.6, 5.4; HRMS (EI+) calcd. for C$_{16}$H$_{30}$O$_3$Si (M)$^+$ 298.1964, found 298.1972.

Example 31

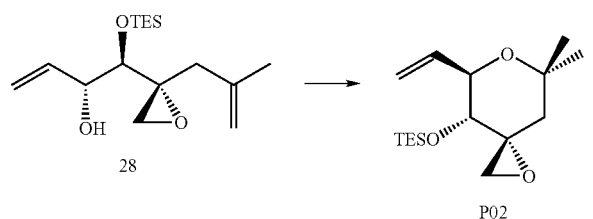

To a stirred solution of 28 (448 mg, 1.50 mmol) in THF (7.5 mL) was added Hg(OAc)$_2$ (526 mg, 1.65 mmol) in one portion at 0° C. under a nitrogen atmosphere. After an additional 0.5 h at the same temperature, the reaction was warmed to 23° C. After an additional 1 h at the same temperature, the reaction mixture was cooled to −78° C., and NaBH$_4$ (113 mg, 2.99 mmol) was added in one portion followed by the addition of Et$_3$B (1.0 M in hexanes, 1.5 mL) down the flask sides at the same temperature. After an additional 2.8 h at −78° C., the reaction mixture was warmed to −44° C. After an additional 0.5 h at the same temperature, the reaction mixture was quenched with saturated aqueous NH$_4$Cl (25 mL). The reaction mixture was then extracted with Et$_2$O (3×20 mL). The combined organic layers were washed with H$_2$O (25 mL) then brine (25 mL), dried over anhydrous Na$_2$SO$_4$, filtered, and concentrated under reduced pressure. The resulting residue was purified by flash chromatography (2→10% EtOAc in hexanes) on silica gel (40 mL) to afford P02 (325 mg, 76%) as a pale yellow oil.

Example 32

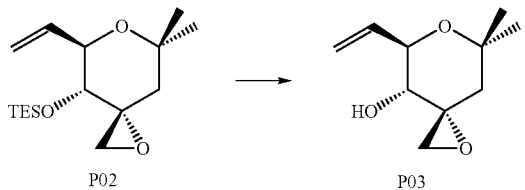

Preparation of P03. To a stirred solution of P02 (299 mg, 1.00 mmol) in THF (4 mL) was added TBAF (1 M in THF, 1.2 mL) at 0° C. under an open atmosphere. After 20 min at the same temperature, the reaction mixture was diluted with Et$_2$O (15 mL), filtered through a pad of Florisil, rinsed with Et$_2$O (4×10 mL), and concentrated under reduced pressure. The resulting residue was purified by flash chromatography (10→40% EtOAc in hexanes) on silica gel (10 mL) to afford P03 (179 mg, 97%) as a white solid.

Data for P03: m.p.=60-62° C.; $R_f$=0.xx (30% EtOAc in hexanes); IR (neat): 3403 (br, O—H), 2973, 1371, 1223, 1062, 895; $[\alpha]_D^{23}$ +72.3 (c 1.0, CH$_2$Cl$_2$); $^1$H NMR (300 MHz, 293K, CD$_2$Cl$_2$) δ 5.95 (ddd, 1H, J=17.2, 10.5, 5.9 Hz), 5.34 (ddd, 1H, J=17.2, 1.6, 1.6 Hz), 5.22 (ddd, 1H, J=10.5, 1.5, 1.1 Hz), 3.91 (br dd, 1H, J=9.7, 5.9 Hz), 3.44 (br app t, 1H, J=10.1 Hz), 2.96 (d, 1H, J=4.7 Hz), 2.46 (d, 1H, J=4.7 Hz), 2.16 (d, 1H, J=14.3 Hz), 1.65 (br d, 1H, J=10.6 Hz), 1.39 (d, 1H, J=14.3 Hz), 1.35 (s, 3H), 1.24 (s, 3H); $^{13}$C NMR (75 MHz, 293K, CD$_2$Cl$_2$) δ 137.5, 117.0, 74.8, 73.0, 68.4, 57.8, 47.8, 43.1, 31.1, 23.7; HRMS (EI+) calcd. for C$_9$H$_{13}$O$_3$ (M−CH$_3$)$^+$ 169.0865, found 169.0869.

Example 33

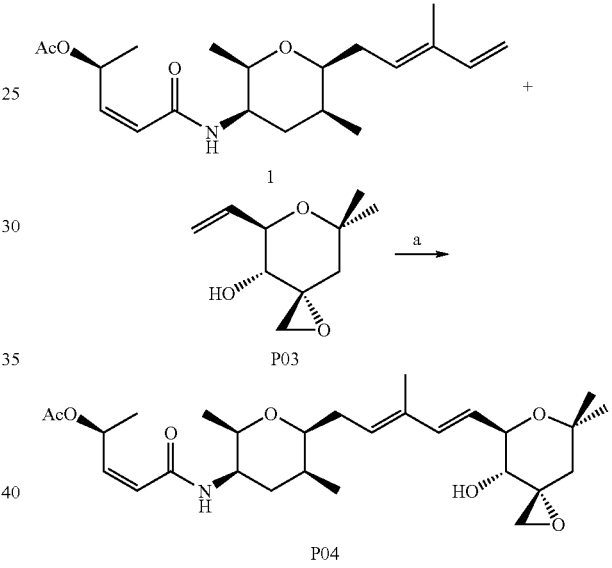

Preparation of P04. A solution of P03 (5.6 mg, 0.030 mmol) was prepared in ClCH$_2$CH$_2$Cl (100 μL) at 23° C. under an open atmosphere. To a stirred solution of 1$^+$ (7.0 mg, 0.020 mmol) in ClCH$_2$CH$_2$Cl (50 μL) and p-benzoquinone (0.4 mg, 4 μmol) was added the solution of P03 (50 μL), followed by 22 (0.7 mg, 1.1 μmol) at 34° C. under an open atmosphere. After 2.3 h at the same temperature, additional 22 (0.7 mg, 1.1 μmol) and P03 (50 μL) were added. After 24 total hours, the reaction was concentrated under reduced pressure. The resulting residue was purified by flash chromatography (10→80% EtOAc in hexanes) on silica gel (1.5 mL) to give P04 (4.5 mg, 45%) as a pale tan solid.

Data for P04: $^1$H NMR (300 MHz, 293K, CD$_2$Cl$_2$) δ 6.34 (d, 1H, J=15.7 Hz), 6.26 (m, 1H), 5.97 (br d, 1H, J=9.0 Hz), 5.90 (dd, 1H, J=11.6, 7.8 Hz), 5.71 (dd, 1H, J=11.6, 1.1 Hz), 5.64 (dd, 1H, J=15.7, 6.6 Hz), 5.52 (br app t, 1H, J=6.9 Hz), 3.99-3.88 (m, 2H), 3.65 (qd, 1H, J=6.5, 2.2 Hz), 3.52 (m, 1H), 3.48 (app t, 1H, J=10.0 Hz), 2.95 (d, 1H, J=4.7 Hz), 2.46 (d, 1H, J=4.7 Hz), 2.39-2.30 (m, 1H), 2.28-2.20 (m, 1H), 2.17 (d, 1H, J=14.2 Hz), 2.01 (s, 3H), 1.96-1.90 (m, 2H), 1.79 (m, 1H), 1.78 (br s, 3H), 1.62 (d, 1H, J=10.5 Hz), 1.39 (d, 1H, J=14.2 Hz), 1.38 (s, 3H), 1.33 (d, 3H, J=6.5 Hz), 1.23 (s, 3H), 1.11 (d, 3H, J=6.4 Hz), 1.01 (d, 3H, J=7.3 Hz).

Example 34

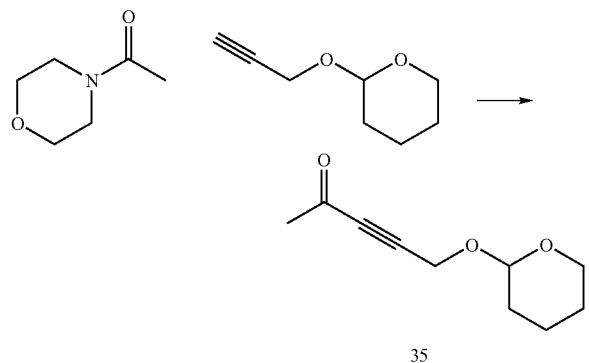

To a stirred solution of tetrahydro-2-(prop-2-ynyloxy)-2H-pyran (21.01 g, 150 mmol) in THF (90 mL) was added "BuLi (1.6 M in hexanes, 92 mL) dropwise over 20 min at 0° C. under a nitrogen atmosphere. After an additional 15 min at the same temperature, N-acetylmorpholine (5.8 mL, 50 mmol) in THF (8 mL) was added dropwise to the reaction mixture, and then the container that initially contained N-acetylmorpholine was rinsed with THF (2×1 mL) and added to the reaction mixture at the same temperature. After an additional 1.4 h at 0° C., the reaction mixture was cannulated into a flask containing AcOH (120 mL) and H$_2$O (60 mL) 0° C., the reaction container was rinsed with Et$_2$O (50 mL), and then the resulting layers were separated. The organic layer was washed with saturated aqueous NaHCO$_3$ (300 mL). The combined aqueous layers were extracted with Et$_2$O (50 mL). The combined organic layers were dried over anhydrous Na$_2$SO$_4$, filtered, and concentrated under reduced pressure. The resulting residue was purified by flash chromatography (2.5→10% EtOAc in hexanes) on silica gel (600 mL) to afford 35 (7.141 g, 78%) as a colorless oil.

Spectroscopic data for 35 were consistent with the literature (*J. Org. Chem.* 1983, 48, 2151-2158).

Example 35

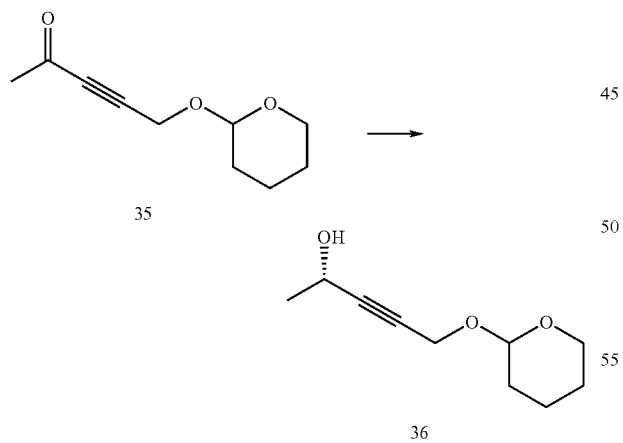

To a stirred solution of (S)-2-methyl-CBS-oxazaborolidine (554 mg, 2.00 mmol) and catechol borane (1.7 mL, 16 mmol) in EtNO$_2$ (25 mL) was added 35 (1.83 g, 10.0 mmol) in EtNO$_2$ (7 mL) via syringe pump over 20 min which was followed by a rinse of the container that originally contained 35 with EtNO$_2$ (1 mL) at −78° C. under a nitrogen atmosphere. After an additional 2.7 h at the same temperature, the reaction was quenched with saturated aqueous NaHCO$_3$ (35 mL), and the mixture was then diluted with Et$_2$O (100 mL). The layers were separated and the organic layer was washed with an aqueous NaOH solution (1 N, 2×20 mL), dried over anhydrous Na$_2$SO$_4$, filtered, and concentrated under reduced pressure. The resulting residue was purified by flash chromatography (10→30% EtOAc in hexanes) on silica gel (100 mL) to afford 36 and a small amount of catechol (1.979 g) as a pale yellow oil.

Spectroscopic data for 36 were consistent with the literature (*Tetrahedron* 1990, 46, 4063-4082).

Example 36

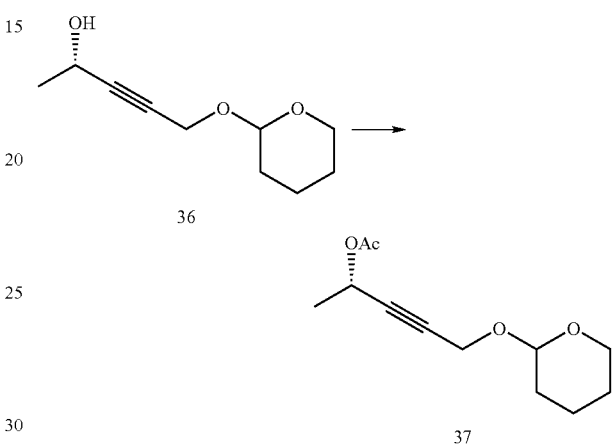

To a stirred solution of impure 36 (1.59 g, ~8.0 mmol) in pyridine (15 mL) was added Ac$_2$O (3.5 mL, 37 mmol) at 23° C. under an open atmosphere. After 41.5 h at the same temperature, the reaction mixture was diluted with H$_2$O (330 mL) and saturated aqueous NaHCO$_3$ (20 mL). The resulting mixture was then extracted with Et$_2$O (3×75 mL). The combined organic layers were washed with saturated aqueous CuSO$_4$ (1×50 mL), dried over anhydrous Na$_2$SO$_4$, filtered, and concentrated under reduced pressure. The resulting residue was purified by flash chromatography (5→10% EtOAc in hexanes) on silica gel (75 mL) to afford 37 (1.79 g, 97% for the two steps) as a colorless oil.

$^1$H NMR (300 MHz, 293K, CDCl$_3$) δ 5.51 (br q, 1H, J=6.7 Hz), 4.82-4.78 (m, 1H), 4.34 (dd, 1H, J=15.7, 1.7 Hz), 4.26 (dd, 1H, J=15.7, 1.6 Hz), 3.84 (br ddd, 1H, J=11.9, 9.0, 3.2 Hz), 3.58-3.50 (m, 1H), 2.08 (s, 3H), 1.89-1.53 (m, 6H), 1.50 (d, 1H, J=6 Hz); $^{13}$C NMR (75 MHz, 293K, CD$_2$Cl$_2$) δ 169.8, 96.7, 84.22, 84.19, 80.7, 61.9, 60.3, 54.11, 54.08, 30.1, 25.3, 21.3, 21.0;

Example 37

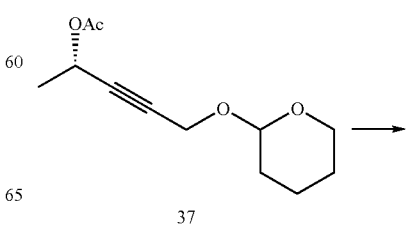

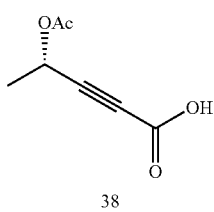

To a stirred solution of 37 (113 mg, 0.501 mmol) in acetone (2 mL) was added cold $Na_2Cr_2O_7$ (0.5 N, 3.5 mL dissolved in 2 N $H_2SO_4$) dropwise at 0° C. under an open atmosphere. After 2 h at the same temperature, the reaction was warmed to 23° C. After 30 min at the same temperature, the reaction was cooled to 0° C., and to the reaction mixture was added $Na_2SO_3$ (63.3 mg, 0.502 mmol). After an additional 15 min at the same temperature, the reaction mixture was poured onto aqueous HCl (1 N, 30 mL), and the mixture was extracted with EtOAc (5×10 mL). The combined organic layers were dried over anhydrous $Na_2SO_4$, filtered, and concentrated under reduced pressure. The resulting residue was purified by flash chromatography (20→100% EtOAc in hexanes containing 1% AcOH) on silica gel (5 mL) to afford 38 (68.4 mg, 74%) as a colorless oil.

Example 38

Compound 39-15 may be prepared as indicated in the scheme below. Details for the synthesis of compounds 39-2 to 39-7 follow the scheme (CSA=camphorsulfonic acid; Boc=t-butyloxycarbonyl; DIBALH=diisobutylaluminum hydride; HATU=N-[(dimethylamino)-1H-1,2,3-triazolo[4,5-b]pyridine-1-ylmethylene]-N-methylmethanaminium hexafluorophosphate N-oxide).

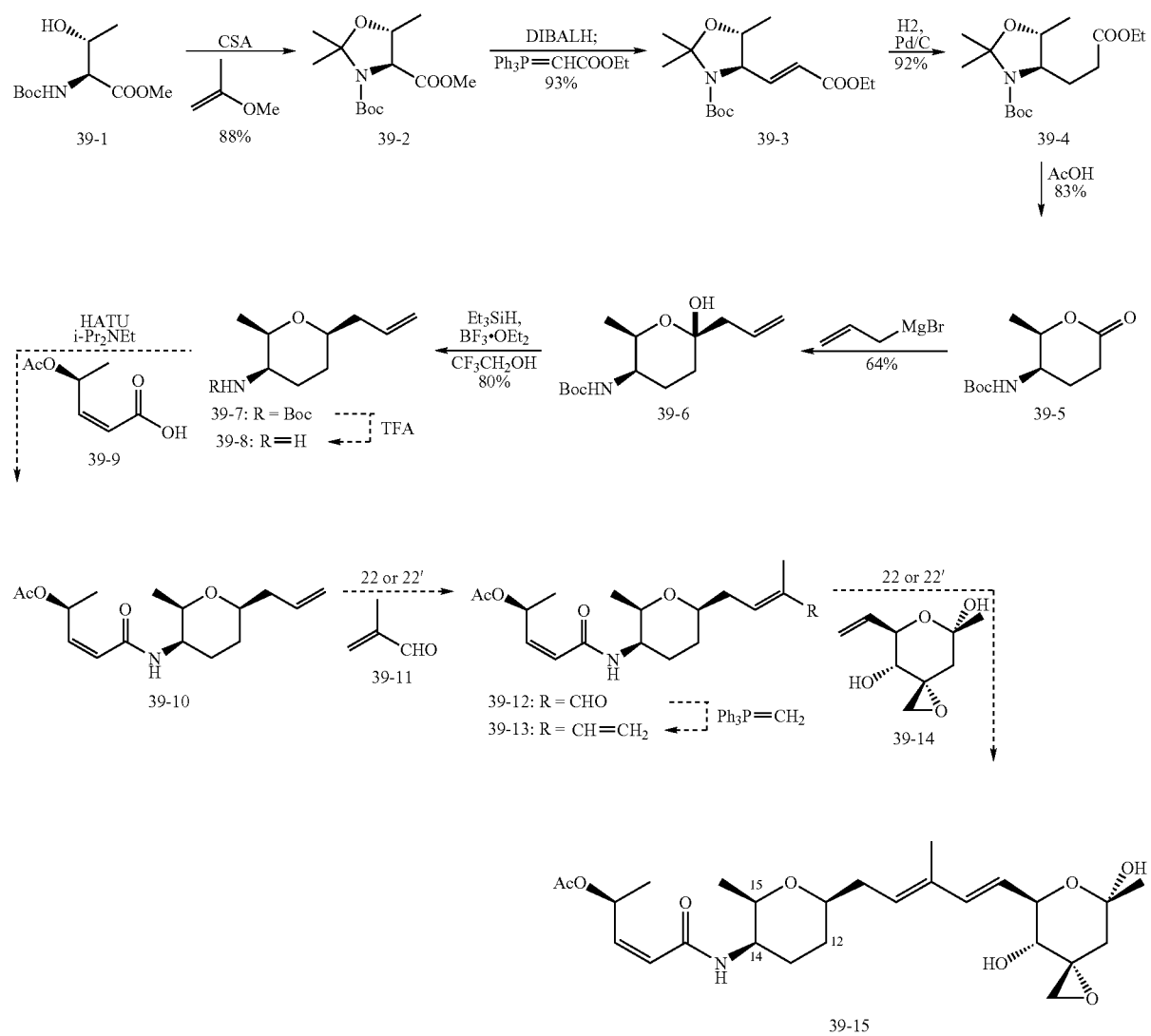

To a stirred solution of 39-2 (2.03 g, 7.43 mmol) in CH$_2$Cl$_2$ (24 mL) was added DIBAL-H (1 M in hexanes, 14.9 mL) slowly down the flask side at −78° C. under a nitrogen atmosphere. After 1 hour at the same temperature, ethanol was added (4.4 mL), and the reaction mixture was allowed to warm to 0° C. After an additional 20 minutes at the same temperature, the reaction was removed from the nitrogen atmosphere and THF was added (30 mL) followed by the Ph$_3$PCHCOOCH$_2$CH$_3$ (7.7 g). The reaction was allowed to warm to 23° C. and was stirred for 17 hours at the same temperature at which time it was quenched with saturated NH$_4$Cl (5 mL). To the reaction mixture was added hexanes (25 mL) and the mixture was dried over anhydrous Na$_2$SO$_4$, filtered through cotton, and concentrated under reduced pressure. The resulting residue was purified by flash chromatography (2.5→15% EtOAc in hexanes) on silica gel (200 mL) to afford 39-3 (2.16 g, 93%) as colorless oil: R$_f$=0.26 (5% EtOAc in hexanes) IR (neat): 2980, 2935, 1702 (C=O), 1661 (C=O), 1478, 1456, 1367, 1257 cm$^{-1}$; [α]$_D^{24}$=−28.1 (c 1.0, CHCl$_3$); $^1$H NMR (300 MHz, 338 K, C$_6$D$_6$) δ 6.90 (dd, 1H, J=15.6, 7.8 Hz), 5.94 (d, 1H, J=15.6 Hz), 4.05 (dd, 2H, J=7.1 Hz), 3.75-3.62 (m, 2H), 1.67 (s, 3H), 1.50 (s, 3H), 1.39 (s, 9H), 1.02 (t, 3H, J=7.1 Hz), 1.01 (d, 3H, J=5.0 Hz); $^{13}$C NMR (75 MHz, 293 K, C$_6$D$_6$) δ 165.6, 152.0, 147.0, 122.9, 94.8, 80.0, 75.1, 65.8, 60.2, 28.4, 27.1, 26.0, 17.5, 14.2; HRMS (EI+) calcd. for C$_{15}$H$_{24}$NO$_5$ (M+) 298.1654, found 298.1647.

To a stirred solution of 39-3 (4.31 g, 13.7 mmol) in EtOAc (70 mL) was added Pd—C (147.2 mg, 10% wt/wt) at 23° C. under an argon atmosphere. The reaction flask was then put under a hydrogen atmosphere. After 1 hour at the same temperature, the reaction mixture was gravity filtered, rinsed with EtOAc, and concentrated in vacuo. The resulting residue was purified by flash chromatography (2.5→10% EtOAc in hexanes) on silica gel (200 mL) to give 39-4 (3.98 g, 92%) as a colorless oil: R$_f$=0.17(5% EtOAc in hexanes) IR (neat): 2978, 2935, 1737 (C=O), 1697 (C=O), 1456, 1256, 1177, 860 cm$^{-1}$; [α]$_D^{24}$=−28.9 (c 1.0, CHCl$_3$); $^1$H NMR (300 MHz, 338 K, C$_6$D$_6$) δ 3.96 (q, 2H, J=7.1 Hz), 3.74 (dd, 1H, J=12.1, 6.0 Hz), 3.45 (dd, 1H, J=10.7, 5.5 Hz), 2.39-2.21 (m, 2H), 2.11-2.06 (m, 2H), 1.67 (s, 3H), 1.50 (s, 3H), 1.42 (s, 9H), 1.08 (d, 3H, J=6.1 Hz), 1.0 (t, 3H, J=7.1 Hz); $^{13}$C NMR (75 MHz, 293 K, C$_6$D$_6$) δ 172.5, 152.3, 94.2, 79.6, 75.5, 63.5, 60.1, 30.7, 28.5, 28.3, 28.0, 27.1, 20.2, 14.2; HRMS (EI+) calcd. for C$_{16}$H$_{29}$NO$_5$ (M+) 315.2046, found 315.2057.

To a flask containing 39-4 (475 mg, 1.51 mmol) was added AcOH (5 mL) under an open atmosphere at 23° C. The reaction was heated to 80° C. and remained at the temperature for 17 hours. The acetic acid was stripped off in vacuo and to the resulting residue was added saturated aqueous NaHCO$_3$ (10 mL) and di-tert-butyl dicarbonate (165 mg, 0.5 equiv.) and stirred for 30 minutes. The mixture was extracted with EtOAc (2×20 mL). The combined organic layers were washed with brine (25 mL), dried over anhydrous Na$_2$SO$_4$, filtered through cotton, and concentrated in vacuo. The resulting residue was purified by flash chromatography (5→15% iPrOH in hexanes) on silica gel (25 mL) to afford 39-4 (128 mg) and 39-5 (209.4, 83% adjusted for recovered 39-4) as a white solid: R$_f$=0.21 (10% $^i$PrOH in hexanes) IR (neat): 3337 (N—H), 2979, 2935, 1709 (C=O), 1697 (C=O), 1527, 1250, 1171, 1059 cm$^{-1}$; [α]$_D^{24}$=+38.8 (c 1.0, CHCl$_3$); $^1$H NMR (300 MHz, 293 K, CDCl$_3$) δ 4.54 (ddd, 1H, J=11.6, 5.1, 2.7 Hz), 4.04-4.02 (m, 1H), 2.58 (dd, 2H, J=6.9, 6.9 Hz), 2.21 (dddd, 1H, J=14.2, 6.1, 6.1, 6.1 Hz), 1.97 (dddd, 1H, J=14.0, 6.9, 6.9, 4.1 Hz), 1.46 (s, 9H), 1.37 (d, 3H, J=6.5 Hz) $^{13}$C NMR (75 MHz, 293 K, C$_6$D$_6$) δ 170.2, 155.6, 78.8, 76.5, 46.5, 28.2, 26.1, 25.4, 16.5; HRMS (EI+) calcd. for C$_{11}$H$_{19}$NO$_4$ (M+) 229.1314, found 229.1306.

To a stirred solution of 39-5 (332.6 mg, 1.45 mmol) in THF (5.8 mL) was added CH$_2$CHCH$_2$MgCl (1.7 M in THF) slowly down the flask side at −78° C. under a nitrogen atmosphere. After 1 hour at the same temperature, the reaction was quenched with saturated NH$_4$Cl (9 mL). The reaction mixture was extracted with EtOAc (3×10 mL). The combined organic layers were washed with brine (15 mL), dried over anhydrous Na$_2$SO$_4$, filtered through cotton, and concentrated in vacuo to afford 39-6.

To a stirred solution of 39-6 (101.7 mg, 0.375 mmol) in CH$_2$Cl$_2$ was added Et$_3$SiH (0.6 mL), CF$_3$CH$_2$OH (0.216 mL), and BF$_3$.OEt$_2$ (0.19 mL) slowly down the flask side at −78° C. under a nitrogen atmosphere. After 1.5 hours at the same temperature, the reaction was quenched with NaHCO$_3$ (15 mL), then di-tert-butyl dicarbonate (65 mg, 0.8 equiv.) was added and stirred for 30 minutes. The reaction mixture was extracted with EtOAc (2×10 mL). The combined organic layers were washed with brine (1×15 mL), dried over anhydrous Na$_2$SO$_4$, filtered through cotton, and concentrated in vacuo. The resulting residue was purified with flash chromatography (2.5→15% EtOAc in hexanes) on silica gel (4 mL) to afford 39-7 (76.5 mg, 80%) as a colorless oil: R$_f$=0.32 (5% EtOAc in hexanes) IR (neat): 3453 (N—H), 2978, 2935, 1715 (C=O), 1642 (C=C), 1496, 1172, 1074 cm$^{-1}$; [α]$_D^{24}$=−10.1 (c 1.0, CHCl$_3$); $^1$H NMR (300 MHz, 293 K, CDCl$_3$) δ 5.83 (dddd, 1H, J=17.2, 10.1, 7.2, 7.2 Hz), 5.10-5.02 (m, 2H), 3.61-3.57 (m, 2H), 3.38 (dddd, 1H, J=11.3, 5.8, 3.5, 3.5 Hz), 2.31 (ddd, 1H, J=14.1, 6.5, 6.5 Hz), 2.15 (ddd, 1H, J=13.9, 7.2, 7.2 Hz), 1.88 (br. dddd, 1H, J=13.7, 4.4, 2.6, 2.6 Hz), 1.67 (br. dddd, 2H, J=13.7, 13.7, 4.0, 4.0 Hz), 1.44 (s, 9H), 1.20-1.34 (m, 2H), 1.12 (d, 3H, J=6.3 Hz); $^{13}$C NMR (75 MHz, 293 K, C$_6$D$_6$) δ 155.7, 135.1, 116.6, 78.6, 77.6, 75.3, 48.3, 41.0, 29.4, 28.5, 25.8, 18.2; HRMS (EI+) calcd. for C$_{14}$H$_{26}$NO$_3$ (M+) 256.1913, found 256.1900.

Example 39

FR901464 (compound X) and its dimethyl analog (compound IX) were prepared synthetically and dissolved in dimethyl sulfoxide (DMSO) as 10 μM stocks and stored at −80° C. For the experiments, aliquots were thawed at room temperature and dilutions were prepared in RPMI 1640 medium containing 2% DMSO at 2× the desired concentration prior to addition to the cells.

MCF-7 cells were used in this experiment. The cells were grown at 37° C. in an atmosphere containing 5% carbon dioxide in coming cell culture dishes (150 mm) in RPMI 1640 cell culture medium containing 10% fetal bovine serum and 5 mL of gultamine pen-strep solution (Invitrogen) per 500 mL of medium.

Cells were plated in 96 well plates at an initial density of 25,000 cells/well and were incubated for 24 hours prior to compound addition. The compound was added to the cells at 2× the desired concentration into an equal volume of cell culture medium. The cells were then incubated for an additional 24 to 48 hours. Cell proliferation was measured by manual counting using a hemacytometer by trypsinizing and staining with trypan blue. Each compound treatment was done in quadruplets and the final counts were averaged.

After 24 hours of incubation with the compound, 81% of the cells treated with 10 nM of FR901464 remained while only 46% of the cells treated with 10 nM of the 1,1 dimethyl analog were still present as indicated in Table 1 and in FIG. 1. At 48 hours, 49% of the FR901464 treated cells remained compared to only 27% with the analog. The cells grown only in the presence of DMSO increased in density by approximately 22%. A positive control was also done using 200 nM Taxol. These cells were present at 70% and 52% at the 24 and 48 hour time marks, respectively.

TABLE 1

| Time (hours) | Percent Viable Cells | |
|---|---|---|
| | 10 nM Compound X | 10 nM Compound IX |
| 24 | 81% | 46% |
| 48 | 49% | 26% |

Example 40

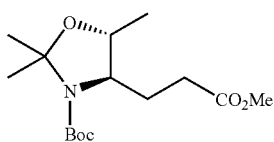

Preparation of (4R,5R,E)-tert-butyl 4-(3-methoxy-3-oxoprop-1-enyl)-2,2,5-trimethyloxazolidine-3-carboxylate. To a stirred solution of ester (4S,5R)-3-tert-butyl 4-methyl 2,2,5-trimethyloxazolidine-3,4-dicarboxylate (3.20 g, 11.7 mmol) in $CH_2Cl_2$ (40 mL) at −78° C. was added DIBALH (1 M in hexanes, 21.1 mL) slowly down the flask side under a $N_2$ atmosphere. The reaction mixture was stirred for 1 h at −78° C. before adding MeOH (6 mL) slowly. The mixture was warmed to 0° C. and THF (20 mL) was added followed by Wittig reagent $Ph_3P$=$CHCO_2Me$ (5.87 g, 17.6 mmol). The mixture was then allowed to warm to 23° C. and was stirred for 20 h before being quenching with sodium potassium tartrate (1 M, 80 mL). After stirring at 23° C. for 2 h, the mixture was extracted with EtOAc (2×100 mL). The combined organic layers were washed with brine (50 mL), dried over anhydrous $Na_2SO_4$, filtered and concentrated in vacuo. The crude residue was purified by flash chromatography (5→15% EtOAc in hexanes) on silica (80 mL) to afford ester (4R,5R,E)-tert-butyl 4-(3-methoxy-3-oxoprop-1-enyl)-2,2,5-trimethyloxazolidine-3-carboxylate (3.05 g, 87%) as a colorless oil.

Data for (4R,5R,E)-tert-butyl 4-(3-methoxy-3-oxoprop-1-enyl)-2,2,5-trimethyloxazolidine-3-carboxylate: $R_f$=0.45 (20% EtOAc in hexanes); IR (neat): 2979, 2935, 1728 (C=O), 1662 (C=O), 1388, 1274, 1172 $cm^{-1}$; $[\alpha]_D25$ −31.2 (c 0.82, $CH_2Cl_2$); $^1H$ NMR (300 MHz, 343 K, $C_6D_6$) δ 6.96 (dd, 1H, J=15.9, 7.8 Hz), 6.25 (d, 1H, J=15.6 Hz), 3.84-3.68 (m, 2H), 3.55 (s, 3H), 1.76 (s, 3H), 1.59 (s, 3H), 1.48 (s, 9H), 1.10 (d, 3H, J=6.3 Hz); $^{13}C$ NMR (75 MHz, 343K, $C_6D_6$) δ 166.0, 152.0, 147.3, 122.5, 94.8, 80.0, 75.1, 65.8, 51.0, 28.4, 27.2, 26.0, 17.5; HRMS (ES+) calcd. for $C_{15}H_{25}NO_5$ $(M+Na)^+$ 322.1630, found 322.1626.

Example 41

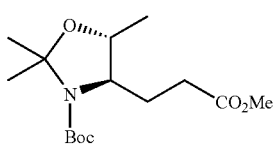

Preparation of (4R,5R)-tert-butyl 4-(3-methoxy-3-oxopropyl)-2,2,5-trimethyloxazolidine-3-carboxylate. To a stirred solution of unsaturated ester (4R,5R,E)-tert-butyl 4-(3-methoxy-3-oxoprop-1-enyl)-2,2,5-trimethyloxazolidine-3-carboxylate (5.03 g, 16.8 mmol) in EtOAc (100 mL) at 23° C. was added Pd/C (179 mg, 10% wt/wt, 0.168 mmol). The flask was flushed with $H_2$ and kept under a hydrogen atmosphere. After stirring 1 h at 23° C., the reaction mixture was passed through a pad of celite and rinsed with EtOAc (50 mL). The filtrate was concentrated in vacuo. The residue was purified by flash chromatography (5→15% EtOAc in hexanes) on silica (60 mL) to afford ester (4R,5R)-tert-butyl 4-(3-methoxy-3-oxopropyl)-2,2,5-trimethyloxazolidine-3-carboxylate (5.02 g, 99%) as a colorless oil.

Data for (4R,5R)-tert-butyl 4-(3-methoxy-3-oxopropyl)-2,2,5-trimethyloxazolidine-3-carboxylate: $R_f$=0.38 (20% EtOAc in hexanes); IR (neat): 2978, 2934, 1741 (C=O), 1697 (C=O), 1390, 1367, 1255, 1174 $cm^{-1}$; $[\alpha]_D25$ −30.5 (c 0.95, $CH_2Cl_2$); $^1H$ NMR (300 MHz, 343 K, C6D6) δ 3.73 (dt, 1H, J=6.0, 5.7 Hz), 3.42 (m, 1H), 3.37 (s, 3H), 2.33-2.13 (m, 2H), 2.07-2.01 (m, 2H), 1.65 (s, 3H), 1.49 (s, 3H), 1.42 (s, 9H), 1.08 (d, 3H, J=6.3 Hz); $^{13}C$ NMR (75 MHz, 343K, C6D6) δ 172.9, 152.3, 94.2, 79.6, 75.5, 63.5, 50.9, 30.4, 28.5, 28.3, 27.9, 27.1, 20.2; HRMS (ES+) calcd. for $C_{15}H_{27}NO_5$ $(M+Na)^+$ 324.1787, found 324.1772.

Example 42

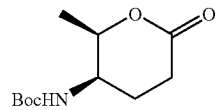

Preparation of tert-butyl (2R,3R)-2-methyl-6-oxo-tetrahydro-2H-pyran-3-ylcarbamate. The solution of ester (4R,5R)-tert-butyl 4-(3-methoxy-3-oxopropyl)-2,2,5-trimethyloxazolidine-3-carboxylate (4.50 g, 14.9 mmol) in AcOH (50 mL) was heated to 80° C. under an open atmosphere. The mixture was stirred and remained at 80° C. for 24 h, and the AcOH was removed in vacuo. To the residue was added THF (25 mL), saturated $NaHCO_3$ (25 mL) and $Boc_2O$ (3.25 g, 14.9 mmol). The mixture was stirred for 30 min at 23° C. and extracted with EtOAc (2×100 mL). The combined organic layers were washed with brine (50 mL), dried over anhydrous $Na_2SO_4$, filtered and concentrated in vacuo. The crude residue was purified by flash chromatography (5→40% EtOAc in hexanes) on silica (80 mL) to afford lactone tert-butyl (2R,3R)-2-methyl-6-oxo-tetrahydro-2H-pyran-3-ylcarbamate (2.50 g, 73%) as a white solid.

Data for tert-butyl (2R,3R)-2-methyl-6-oxo-tetrahydro-2H-pyran-3-ylcarbamate: m.p.=98.2-99.5° C.; $R_f$=0.27 (50% EtOAc in hexanes); IR (neat): 3337, 2979, 2935, 1709 (C=O), 1697 (C=O), 1527, 1250, 1171, 1059 $cm^{-1}$; $[\alpha]_D25$ +38.8 (c 1.0, $CHCl_3$); $^1H$ NMR (300 MHz, 293 K, CDCl3) δ 4.74 (br, 1H), 4.52 (ddd, 1H, J=12.9, 6.3, 2.4 Hz), 3.99 (m br, 1H), 2.55 (dd, 2H, J=8.1, 6.9 Hz), 2.24-2.12 (m, 1H), 1.99-1.88 (m, 1H), 1.43 (s, 9H), 1.33 (d, 3H, J=6.6 Hz); $^{13}C$ NMR (75 MHz, 293K, CDCl3) δ 171.2, 155.5, 79.8, 77.4, 46.6, 28.2, 26.0, 25.5, 16.8; HRMS (EI+) calcd. for $C_{11}H_{19}NO_4$ $(M)^+$ 229.1314, found 229.1306.

Example 43

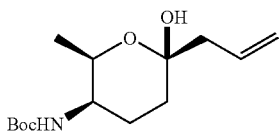

Preparation of tert-butyl (2R,3R)-6-allyl-6-hydroxy-2-methyl-tetrahydro-2H-pyran-3-ylcarbamate. To a stirred solution of lactone tert-butyl (2R,3R)-2-methyl-6-oxo-tetrahydro-2H-pyran-3-ylcarbamate (1.00 g, 4.36 mmol) in THF (20 mL) at −78° C. was added allylmagnesium chloride (1.7 M solution in THF, 4.87 mL, 8.28 mmol) down the flask sides under a nitrogen atmosphere. After 1.5 h at the same temperature, the reaction was quenched with saturated aqueous NH$_4$Cl (10 mL) and most of the organic solvent was removed in vacuo. The aqueous residue was extracted with EtOAc (2×50 mL). The combined organic layers were washed with brine (30 mL), dried over anhydrous Na$_2$SO$_4$, filtered and concentrated in vacuo. The residue (1.30 g) was used in the next step without further purification.

Example 44

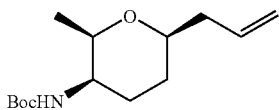

Preparation of tert-butyl (2R,3R,6R)-6-allyl-2-methyl-tetrahydro-2H-pyran-3-ylcarbamate. To a stirred solution of hemiketal tert-butyl (2R,3R)-6-allyl-6-hydroxy-2-methyl-tetrahydro-2H-pyran-3-ylcarbamate (1.30 g) in CH$_2$Cl$_2$ (30 mL) at −78° C. was added Et$_3$SiH (7.0 mL, 44 mmol), CF$_3$CH$_2$OH (2.6 mL, 35 mmol), and BF$_3$.OEt$_2$ (2.2 mL, 17 mmol). After 1.5 h at the same temperature, saturated aqueous NaHCO$_3$ (50 mL) was added at −78° C. The mixture was extracted with EtOAc (2×50 mL). The combined organic layers were washed with brine (30 mL), dried over anhydrous Na$_2$SO$_4$, filtered and concentrated in vacuo. The crude residue was purified by flash chromatography (3→15% EtOAc in hexanes) on silica (20 mL) to afford alkene tert-butyl (2R,3R,6R)-6-allyl-2-methyl-tetrahydro-2H-pyran-3-ylcarbamate (0.47 g, 43%) as a colorless oil.

Data for tert-butyl (2R,3R,6R)-6-allyl-2-methyl-tetrahydro-2H-pyran-3-ylcarbamate: R$_f$=0.48 (20% EtOAc in hexanes); IR (neat): 3453, 2978, 2935, 1715 (C=O), 1642, 1496, 1172, 1074 cm$^{-1}$; [α]$_D$25 −10.1 (c 1.0, CHCl$_3$); 1H NMR (300 MHz, 293 K, CDCl$_3$) δ 5.81-5.67 (m, 1H), 5.03-4.95 (m, 2H), 4.89 (br d, 1H, J=9.3 Hz), 3.54-3.48 (m, 2H), 3.36-3.28 (m, 1H), 2.29-2.20 (m, 1H), 2.13-2.03 (m, 1H), 1.86-1.82 (m, 1H), 1.66-1.55 (m, 1H), 1.48-1.42 (m, 2H), 1.38 (s, 9H), 1.05 (d, 3H, J=6.3 Hz); $^{13}$C NMR (75 MHz, 293K, CDCl3) δ 155.7, 134.5, 116.7, 78.9, 77.6, 75.2, 47.9, 40.6, 29.1, 28.3, 25.7, 17.9; HRMS (EI+) calcd. for C$_{14}$H$_{25}$NO$_3$ (M+H)$^+$ 296.1913, found 296.1900.

Example 45

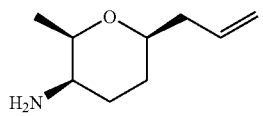

Preparation of (2R,3R,6R)-6-allyl-2-methyl-tetrahydro-2H-pyran-3-amine. To a solution of 40 mL of 10% TFA in CH$_2$Cl$_2$ at 0° C. was added the Boc-protected amine tert-butyl (2R,3R,6R)-6-allyl-2-methyl-tetrahydro-2H-pyran-3-ylcarbamate (1.85 g, 7.24 mmol). The reaction was warmed to 23° C. and stirred for 3 h. The solvent was removed in vacuo, and the residue was used in the next step without further purification.

Example 45

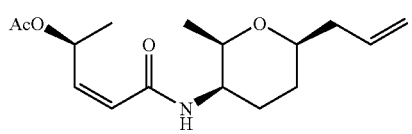

Preparation of (S,Z)-5-((2R,3R,6R)-6-allyl-2-methyl-tetrahydro-2H-pyran-3-ylamino)-5-oxopent-3-en-2-yl acetate. To a stirred solution of acid (S,Z)-4-acetoxypent-2-enoic acid (1.37 g, 8.69 mmol) in CH$_3$CN (25 mL) at 23° C. was added O-(7-azabenzotriazol-1-yl)-N,N,N;N'-tetramethylronium hexafluorophosphate (3.30 g, 8.69 mmol), followed by N,N-diisopropylethylamine (6.3 mL, 36 mmol) under a nitrogen atmosphere. The resulting mixture was then transferred by cannula to a stirred solution of amine (2R,3R,6R)-6-allyl-2-methyl-tetrahydro-2H-pyran-3-amine in CH$_3$CN (25 mL) at the same temperature and rinsed with additional CH$_3$CN (5 mL). After 2 h at 23° C., the reaction was quenched with saturated aqueous NH$_4$Cl (50 mL) and most of the organic solvent was removed in vacuo. The aqueous residue was extracted with EtOAc (3×100 mL). The combined organic layers were washed with brine (50 mL), dried over anhydrous Na$_2$SO$_4$, filtered and concentrated in vacuo. The crude residue was purified by flash chromatography (10→30% EtOAc in hexanes) on silica (60 mL) to afford amide (S,Z)-5-((2R, 3R,6R)-6-allyl-2-methyl-tetrahydro-2H-pyran-3-ylamino)-5-oxopent-3-en-2-yl acetate (1.79 g, 84%) as a colorless oil.

Data for (S,Z)-5-((2R,3R,6R)-6-allyl-2-methyl-tetrahydro-2H-pyran-3-ylamino)-5-oxopent-3-en-2-yl acetate: R$_f$=0.53 (50% EtOAc in hexanes); IR (neat): 3320, 3075, 2978, 2935, 2857, 1739 (C=O), 1671 (C=O), 1635, 1526, 1370, 1242, 1048 cm$^{-1}$; [α]$_D$25 −53.2 (c 1.75, CH$_2$Cl$_2$); 1H NMR (300 MHz, 293 K, CDCl$_3$) δ 6.62 (br d, 1H, J=8.4 Hz), 6.01-5.97 (m, 1H), 5.83-5.67 (m, 3H), 5.03-4.95 (m, 2H), 3.93-3.90 (m, 1H), 3.58 (dq, 1H, J=6.6, 1.5 Hz), 3.41-3.32 (m, 1H), 2.31-2.22 (m, 1H), 2.15-2.05 (m, 1H), 1.98 (s, 3H), 1.95-1.87 (m, 1H), 1.72-1.61 (m, 1H), 1.49-1.43 (m, 1H), 1.36-1.26 (m, 1H), 1.31 (d, 3H, J=6.3 Hz), 1.06 (d, 3H, J=6.3 Hz); $^{13}$C NMR (75 MHz, 293K, CDCl$_3$) δ 170.4, 165.0, 141.1, 134.5, 123.5, 116.6, 77.7, 74.9, 69.9, 46.7, 40.5, 28.8, 25.6, 21.1, 20.0, 18.0; HRMS (EI+) calcd. for $C_{16}H_{25}NO_4$ (M)+ 295.1784, found 295.1787.

Example 46

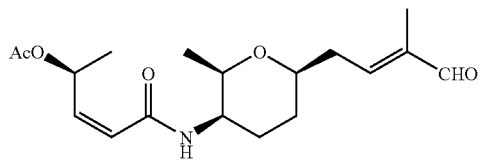

Preparation of (S,Z)-5-((2R,3R,6R)-2-methyl-6-((E)-3-methyl-4-oxobut-2-enyl)-tetrahydro-2H-pyran-3-ylamino)-5-oxopent-3-en-2-yl acetate. To a stirred solution of alkene (S,Z)-5-((2R,3R,6R)-6-allyl-2-methyl-tetrahydro-2H-pyran-3-ylamino)-5-oxopent-3-en-2-yl acetate (1.79 g, 7.0 mmol) in methacrolein (11.6 mL) was added Grela's catalyst (141 mg, 0.21 mmol), and p-benzoquinone (166 mg, 1.54 mmol) under a nitrogen atmosphere. After 9 h at 23° C., the excess methacrolein was removed in vacuo. The residue was purified by flash chromatography (10→60% EtOAc in hexanes) on silica (60 mL) to afford aldehyde (S,Z)-5-((2R,3R,6R)-2-methyl-6-((E)-3-methyl-4-oxobut-2-enyl)-tetrahydro-2H-pyran-3-ylamino)-5-oxopent-3-en-2-yl acetate (1.20 g, 60%) as a colorless oil.

Data for (S,Z)-5-((2R,3R,6R)-2-methyl-6-((E)-3-methyl-4-oxobut-2-enyl)-tetrahydro-2H-pyran-3-ylamino)-5-oxopent-3-en-2-yl acetate: $R_f$=0.35 (60% EtOAc in hexanes); IR (neat): 3331, 2977, 2934, 2857, 1738 (C=O), 1672 (C=O), 1636, 1522, 1370, 1243, 1073, 1051 cm$^{-1}$; $[\alpha]_D25$ −66.9 (c 1.03, $CH_2Cl_2$); $^1$H NMR (300 MHz, 293 K, $CDCl_3$) δ 9.38 (s, 1H), 6.80 (br d, 1H, J=9.0 Hz), 6.59-6.54 (m, 1H), 5.96-5.85 (m, 1H), 5.82-5.68 (m, 2H), 4.0-3.97 (m, 1H), 3.65-3.59 (m, 1H), 3.55-3.49 (m, 1H), 2.56-2.44 (m, 2H), 2.07-1.94 (m, 1H), 2.00 (s, 3H), 1.80-1.73 (m, 1H), 1.70 (s, 3H), 1.52-1.45 (m, 2H), 1.33 (d, 3H, J=6.6 Hz) 1.09 (d, 3H, J=6.3 Hz); $^{13}$C NMR (75 MHz, 293K, $CDCl_3$) δ 195.0, 170.7, 165.2, 150.1, 140.5, 140.0, 124.0, 76.6, 75.2, 68.9, 46.6, 35.6, 28.8, 26.1, 21.1, 20.1, 18.0, 9.3; HRMS (EI+) calcd. for $C_{18}H_{27}NO_5$ (M)+ 337.1889, found 337.1894.

Example 47

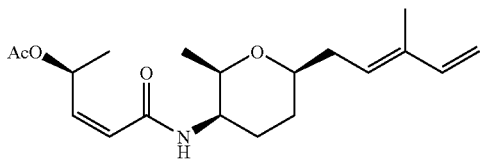

Preparation of (S,Z)-5-((2R,3R,6R)-2-methyl-6-((E)-3-methylpenta-2,4-dienyl)-tetrahydro-2H-pyran-3-ylamino)-5-oxopent-3-en-2-yl acetate. To a stirred suspension of methyltriphenylphosphonium bromide (2.12 g, 5.92 mmol) in THF (20 mL) at 0° C. was added KO$^t$Bu (612 mg, 5.45 mmol) under a nitrogen atmosphere. After 30 min at 0° C., aldehyde (S,Z)-5-((2R,3R,6R)-2-methyl-6-((E)-3-methyl-4-oxobut-2-enyl)-tetrahydro-2H-pyran-3-ylamino)-5-oxopent-3-en-2-yl acetate (800 mg, 2.37 mmol) in THF (5 mL) was added dropwise by cannula at the same temperature and rinsed with additional THF (1 mL). The reaction mixture was warmed to 23° C. After 2 h at 23° C., the reaction was quenched with saturated aqueous NH$_4$Cl (3 mL). The aqueous residue was extracted with EtOAc (3×50 mL). The combined organic layers were washed with brine (20 mL), dried over anhydrous Na$_2$SO$_4$, filtered and concentrated in vacuo. The crude residue was purified by flash chromatography (5→30% EtOAc in hexanes) on silica (50 mL) to afford the terminal alkene (S,Z)-5-((2R,3R,6R)-2-methyl-6-((E)-3-methylpenta-2,4-dienyl)-tetrahydro-2H-pyran-3-ylamino)-5-oxopent-3-en-2-yl acetate (680 mg, 67%) as a colorless oil.

Data for (S,Z)-5-((2R,3R,6R)-2-methyl-6-((E)-3-methylpenta-2,4-dienyl)-tetrahydro-2H-pyran-3-ylamino)-5-oxopent-3-en-2-yl acetate: $R_f$=0.36 (40% EtOAc in hexanes); IR (neat): 3324, 3087, 2978, 2935, 2858, 1740 (C=O), 1670 (C=O), 1635, 1522, 1370, 1243, 1048 cm$^{-1}$; $[\alpha]_D25$ −50.0 (c 1.15, $CH_2Cl_2$); $^1$H NMR (300 MHz, 293 K, CDCl3) δ 6.68 (br d, 1H, J=9.0 Hz), 6.30 (dd, 1H, J=17.4, 10.8 Hz), 6.02-5.93 (m, 1H), 5.82-5.67 (m, 2H), 5.45 (br t, 1H, J=7.4 Hz), 5.03 (d, 1H, J=17.4 Hz), 4.88 (d, 1H, J=10.5 Hz), 3.94-3.92 (m, 1H), 3.57 (ddd, 1H, J=12.9, 6.6, 1.5 Hz), 3.40-3.33 (m, 1H), 2.39-2.19 (m, 2H), 1.98 (s, 3H), 1.92-1.88 (m, 1H), 1.76-1.62 (m, 1H), 1.67 (s, 3H), 1.50-1.45 (m, 1H), 1.40-1.27 (m, 1H), 1.31 (d, 3H, J=6.3 Hz), 1.06 (d, 3H, J=6.3 Hz); $^{13}$C NMR (75 MHz, 293K, CDCl3) δ 170.5, 165.0, 141.2, 140.7, 135.5, 128.0, 123.6, 110.9, 77.9, 74.9, 68.8, 46.7, 35.0, 28.8, 25.8, 21.0, 20.0, 18.0, 11.8; HRMS (EI+) calcd. for C19H29NO4 (M)+ 335.2097, found 335.2093.

Example 48

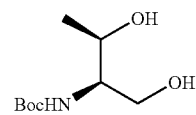

Preparation of tert-butyl (2R,3R)-1,3-dihydroxybutan-2-ylcarbamate. To a stirred solution of ester (2S,3R)-methyl 2-(tert-butoxycarbonyl)-3-hydroxybutanoate (4.0 g, 17 mmol) in EtOH (30 mL) at 0° C. was added NaBH$_4$ (1.3 g, 34 mmol). The reaction mixture was stirred at 0° C. for 1.5 h then warmed to 23° C. and stirred for 1.5 h. Then the reaction mixture was cooled to 0° C. and quenched with saturated aqueous NH$_4$Cl (30 mL). The solvent was then removed and the residue was extracted with EtOAc (2×50 mL). The combined organic layers were washed with brine (30 mL), dried over anhydrous Na$_2$SO$_4$, filtered and concentrated in vacuo. The crude residue was purified by flash chromatography (10→80% EtOAc in hexanes) on silica (40 mL) to afford the diol tert-butyl (2R,3R)-1,3-dihydroxybutan-2-ylcarbamate (3.0 g, 87%) as a colorless oil.

Data for tert-butyl (2R,3R)-1,3-dihydroxybutan-2-ylcarbamate. See Nakamura, Y. et al., *Bull. Chem. Soc. Jpn.*, 68:1369-1377, 1995.

Example 49

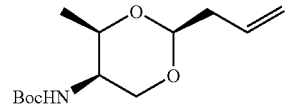

Preparation of tert-butyl (2S,4R,5R)-2-allyl-4-methyl-1,3-dioxan-5-ylcarbamate. To a stirred solution of diol tert-butyl (2R,3R)-1,3-dihydroxybutan-2-ylcarbamate (569 mg, 2.77 mmol) in CH$_2$Cl$_2$ (5 mL) at 0° C. was added 3-butenal diethyl acetal (400 mg, 2.77 mmol) and camphorsulfonic acid (6.4 mg, 0.028 mmol). The mixture was stirred at 0° C. for 6 h and then quenched with saturated aqueous NaHCO$_3$ (15 mL). The mixture was extracted with EtOAc (2×20 mL). The combined organic layers were washed with brine (20 mL), dried over anhydrous Na$_2$SO$_4$, filtered and concentrated in vacuo. The crude residue was purified by flash chromatography (5→15% EtOAc in hexanes) on silica (10 mL) to afford the acetal tert-butyl (2S,4R,5R)-2-allyl-4-methyl-1,3-dioxan-5-ylcarbamate (510 mg, 67%) as a colorless oil.

Data for tert-butyl (2S,4R, 5R)-2-allyl-4-methyl-1,3-dioxan-5-ylcarbamate: R$_f$=0.54 (30% EtOAc in hexanes); IR (neat): 3455, 3345, 3078, 2979, 2934, 2861, 1716 (C=O), 1500, 1365, 1170, 1015 cm$^{-1}$; [α]$_D$25 −23.5 (c 1.10, CH$_2$Cl$_2$); $^1$H NMR (300 MHz, 293 K, CDCl$_3$) δ 5.83-5.69 (m, 1H), 5.20 (br d, 1H, J=9.9 Hz), 5.11-5.04 (m, 2H), 4.56 (t, 1H, J=5.4 Hz), 3.95 (dd, 1H, J=11.7, 1.8 Hz), 3.86 (dq, 1H, J=6.3, 1.8 Hz), 3.78 (dd, J=11.7, 1.8 Hz), 3.45 (dd, 1H, J=9.9, 1.8 Hz, 1H), 2.36-2.32 (m, 2H), 1.41 (s, 9H), 1.13 (d, 3H, J=6.3 Hz); $^{13}$C NMR (75 MHz, 293K, CDCl3) δ 155.8, 132.3, 117.7, 101.8, 79.3, 74.8, 71.4, 48.0, 39.4, 28.3, 17.4; HRMS (EI+) calcd. for C$_{13}$H$_{24}$NO$_4$ (M+H)$^+$ 258.1705, found 258.1707.

Example 50

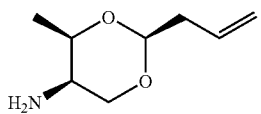

Preparation of (2S,4R,5R)-2-allyl-4-methyl-1,3-dioxan-5-amine. To a solution of 20 mL of 10% TFA in CH$_2$Cl$_2$ at 0° C. was added the Boc-proteted amine tert-butyl (2S,4R,5R)-2-allyl-4-methyl-1,3-dioxan-5-ylcarbamate (770 mg, 2.99 mmol). The reaction was warmed to 23° C. and stirred for 3 h. The solvent was removed in vacuo and the residue was used in the next step without further purification.

Example 51

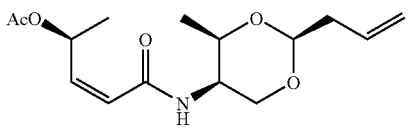

Preparation of (S,Z)-5-((2S,4R,5R)-2-allyl-4-methyl-1,3-dioxan-5-ylamino)-5-oxopent-3-en-2-yl acetate. To a stirred solution of acid (S,Z)-4-acetoxypent-2-enoic acid (470 mg, 2.97 mmol) in CH$_3$CN (20 mL) at 23° C. was added O-(7-azabenzotriazol-1-yl)-N,N,N',N'-tetramethylronium hexafluorophosphate (1.13 g, 2.97 mmol), followed by N,N-diisopropylethylamine (2.6 mL, 15 mmol) under a nitrogen atmosphere. The resulting mixture was then transferred by cannula to a stirred solution of amine (2S,4R,5R)-2-allyl-4-methyl-1,3-dioxan-5-amine in CH$_3$CN (20 mL) at the same temperature and rinsed with additional CH$_3$cN (5 mL). After 2 h at 23° C., the reaction was quenched with saturated aqueous NH$_4$Cl (50 mL) and most of the organic solvent was removed in vacuo. The aqueous residue was extracted with EtOAc (3×40 mL). The combined organic layers were washed with brine (40 mL), dried over anhydrous Na$_2$SO$_4$, filtered and concentrated in vacuo. The crude residue was purified by flash chromatography (10→40% EtOAc in hexanes) on silica (30 mL) to afford amide (S,Z)-5-((2S,4R,5R)-2-allyl-4-methyl-1,3-dioxan-5-ylamino)-5-oxopent-3-en-2-yl acetate (452 mg, 51%) as a colorless oil.

Data for (S,Z)-5-((2S,4R,5R)-2-allyl-4-methyl-1,3-dioxan-5-ylamino)-5-oxopent-3-en-2-yl acetate: R$_f$=0.42 (50% EtOAc in hexanes); IR (neat): 3342, 3077, 2980, 2935, 2862, 1738, 1672, 1642, 1520, 1369, 1244, 1120, 1049 cm$^{-1}$; [α]$_D$25 −42.9 (c 1.10, CH2Cl2); $^1$H NMR (300 MHz, 293 K, CDCl3) δ 6.90 (br d, 1H, J=9.0 Hz), 6.10-6.03 (m, 1H), 5.85-5.69 (m, 3H), 5.11-5.02 (m, 2H), 4.60 (t, 1H, J=5.4 Hz), 3.99-3.95 (m, 1H), 3.94-3.81 (m, 4H), 2.37-2.32 (m, 2H), 1.99 (s, 3H), 1.32 (d, 3H, J=6.3 Hz), 1.12 (d, 3H, J=6.3 Hz); $^{13}$C NMR (75 MHz, 293K, CDCl3) δ 170.4, 165.1, 142.1, 132.2, 123.1, 117.7, 101.8, 74.5, 71.0, 68.7, 46.6, 39.1, 21.1, 20.0, 17.5; HRMS (ES+) calcd. for C$_{15}$H$_{23}$NO$_5$ (M+Na)$^+$ 320.1474, found 320.1462.

Example 52

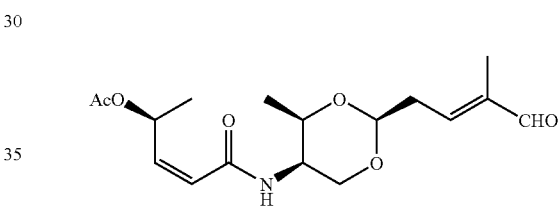

Preparation of (S,Z)-5-((2S,4R,5R)-4-methyl-2-((E)-3-methyl-4-oxobut-2-enyl)-1,3-dioxan-5-ylamino)-5-oxopent-3-en-2-yl acetate. To a stirred solution of alkene (S,Z)-5-((2S,4R,5R)-2-allyl-4-methyl-1,3-dioxan-5-ylamino)-5-oxopent-3-en-2-yl acetate (420 mg, 1.41 mmol) in methacrolein (2.3 mL) was added Grela's catalyst (28 mg, 42 μmol), and p-benzoquinone (18 mg, 0.17 mmol) under a nitrogen atmosphere. After 9 h at 23° C., the excess methacrolein was removed in vacuo. The residue was purified by flash chromatography (10→60% EtOAc in hexanes) on silica (20 mL) to afford aldehyde (S,Z)-5-((2S,4R,5R)-4-methyl-2-((E)-3-methyl-4-oxobut-2-enyl)-1,3-dioxan-5-ylamino)-5-oxopent-3-en-2-yl acetate (292 mg, 62%) as a colorless oil.

Data for (S,Z)-5-((2S,4R,5R)-4-methyl-2-((E)-3-methyl-4-oxobut-2-enyl)-1,3-dioxan-5-ylamino)-5-oxopent-3-en-2-yl acetate: R$_f$=0.29 (60% EtOAc in hexanes); IR (neat): 3350, 2980, 2934, 2861, 1734 (C=O), 1674 (C=O), 1642, 1520, 1368, 1244, 1126, 1049 cm$^{-1}$; [α]$_D$25 −47.8 (c 1.80, CH$_2$Cl$_2$); $^1$H NMR (300 MHz, 293 K, CDCl$_3$) δ 9.41 (s, 1H), 7.08 (br d, 1H, J=8.7 Hz), 6.57-6.52 (m, 1H), 6.05-5.97 (m, 1H), 5.85-5.76 (m, 2H), 4.77 (t, 1H, J=5.1 Hz), 4.05-3.88 (m, 4H), 2.70-2.66 (m, 2H), 2.02 (s, 3H), 1.73 (s, 3H), 1.35 (d, 3H, J=6.3 Hz), 1.16 (d, 3H, J=6.3 Hz); $^{13}$C NMR (75 MHz, 293K, CDCl3) d 194.8, 170.7, 165.3, 147.1, 141.2, 141.1, 123.4, 100.5, 74.7, 71.1, 68.7, 46.6, 34.6, 21.1, 20.0, 17.4, 9.3; HRMS (ES+) calcd. for C$_{17}$H$_{25}$NO$_6$ (M+Na)$^+$ 362.1580, found 362.1551.

Example 53

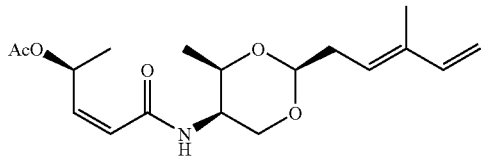

Preparation of (S,Z)-5-((2S,4R,5R)-4-methyl-2-((E)-3-methylpenta-2,4-dienyl)-1,3-dioxan-5-ylamino)-5-oxopent-3-en-2-yl acetate. To a stirred suspension of methyltriphenylphosphonium bromide (500 mg, 1.40 mmol) in THF (5 mL) at 0° C. was added KO$^t$Bu (145 mg, 1.29 mmol) under a nitrogen atmosphere. After 30 min at 0° C., aldehyde (S,Z)-5-((2S,4R,5R)-4-methyl-2-((E)-3-methyl-4-oxobut-2-enyl)-1,3-dioxan-5-ylamino)-5-oxopent-3-en-2-yl acetate (190 mg, 0.56 mmol) in THF (2 mL) was added dropwise by cannula at the same temperature and rinsed with additional THF (1 mL). The reaction mixture was warmed to 23° C. After 2 h at 23° C., the reaction was quenched with saturated aqueous NH$_4$Cl (2 mL). The aqueous residue was extracted with EtOAc (3×20 mL). The combined organic layers were washed with brine (20 mL), dried over anhydrous Na$_2$SO$_4$, filtered and concentrated in vacuo. The crude residue was purified by flash chromatography (10→40% EtOAc in hexanes) on silica (10 mL) to afford the terminal alkene (S,Z)-5-((2S,4R,5R)-4-methyl-2-((E)-3-methylpenta-2,4-dienyl)-1,3-dioxan-5-ylamino)-5-oxopent-3-en-2-yl acetate (112 mg, 67%) as a colorless oil.

Data for (S,Z)-5-((2S,4R,5R)-4-methyl-2-((E)-3-methylpenta-2,4-dienyl)-1,3-dioxan-5-ylamino)-5-oxopent-3-en-2-yl acetate: R$_f$=0.45 (50% EtOAc in hexanes); IR (neat): 3336, 2981, 2861, 1738 (C=O), 1674 (C=O), 1640, 1520, 1368, 1243, 1127, 1048 cm$^{-1}$; [α]$_D$25 −49.9 (c 1.15, CH$_2$Cl$_2$); $^1$H NMR (300 MHz, 293 K, CDCl$^3$) δ 6.97 (br d, 1H, J=9.0 Hz), 6.35 (dd, 1H, J=17.4, 10.8 Hz), 6.10-6.06 (m, 1H), 5.86-5.77 (m, 2H), 5.47 (dd, 1H, J=7.2, 6.9 Hz), 5.09 (d, 1H, J=17.4 Hz), 4.94 (d, J=10.5 Hz), 4.62 (t, 1H, J=5.4 Hz), 4.01-3.83 (m, 4H), 2.49-2.45 (m, 2H), 2.02 (s, 3H), 1.72 (s, 3H), 1.34 (d, 3H, J=6.3 Hz), 1.14 (d, 3H, J=6.3 Hz); $^{13}$C NMR (75 MHz, 293K, CDCl$_3$) δ 170.5, 165.2, 141.8, 141.1, 136.3, 125.6, 123.2, 111.4, 102.0, 74.5, 71.1, 68.8, 46.7, 34.0, 21.2, 20.0, 17.5, 11.9; HRMS (ES+) calcd. for C$_{18}$H$_{27}$NO$_5$ (M+Na)$^+$ 360.1787, found 360.1775.

Example 54

Synthesis of an FR901464 analog (molecule 15 in the reaction pathway; C-12 desmethyl meayamycin)

The analog of FR901464 (C-12 desmethyl meayamycin) was synthesized according to the following synthesis scheme:

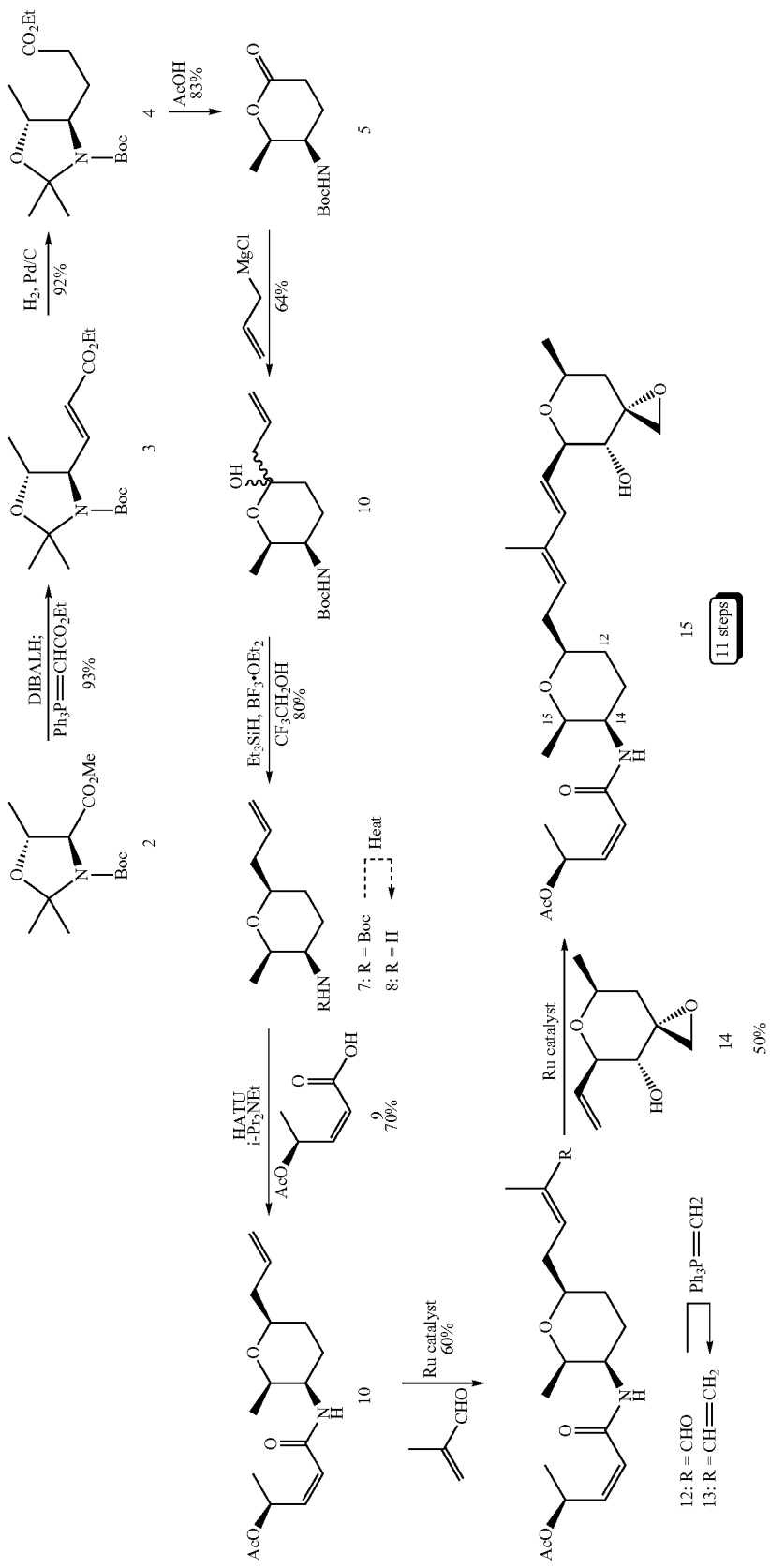

-continued
Note:
DIBALH = Diiosbutylaluminum Hydride
CSA = Camphorsulfonic Acid
Boc =
Ru catalyst =
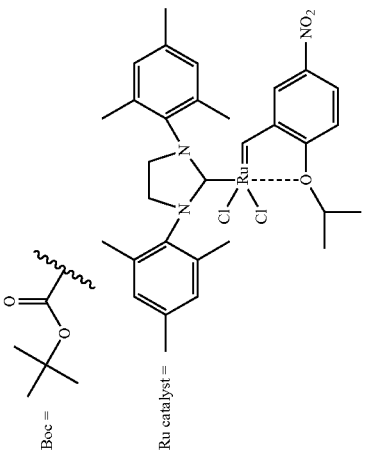

Example 55

Inhibition Assays

Materials

C-12 Desmethyl analog and Meayamycin were produced by total chemical synthesis in our laboratory. The compounds were dissolved in dimethyl sulfoxide (DMSO) as 10 mM stocks and stored at −20° C. For the experiments, aliquots were thawed at room temperature and dilutions were prepared in RPMI 1640 medium containing 2% DMSO at 2× the desired concentration prior to addition to the cells.

Cell Culture

The cells were grown at 37° C. in an atmosphere containing 5% carbon dioxide in coming cell culture flasks (25 cm²) in RPMI 1640 cell culture medium containing 10% fetal bovine serum, 1% Penicillin/Streptomycin, and 1% L-Glutamine.

Growth Inhibition Assay

Cells were plated in 96 well plates at an initial density of 2,000 cells per well in 100 µL of medium and were incubated for 24 hours prior to compound addition. Serial two-fold dilutions were used in this experiment from 100 nM to 0.000191 nM. The compound was added to the cells at 2× the desired concentration in 100 µL cell culture medium. The cells were then incubated for an additional 3 to 5 days. Cell proliferation was measured using a commercial MTS solution (20 µL per well). The absorbance (at 490 nm and 630 nm) was measured by a Spectromax M2 plate reader (Molecular Devices). Each concentration treatment was done in quadruplets and the final numbers were averaged.

Reversibility Tests

Cells were plated in 96 well plates at an initial density of 2,000 cells per well in 100 µL of medium and were incubated for 24 hours prior to compound addition. One concentration was used in each experiment for all times examined. The compound was added to the cells at 2× the desired concentration in 100 µL cell culture medium. At the desired time intervals, the media containing the drug was removed, the wells were washed 5 times with new media and 200 µL of new media containing 1% DMSO was added. At the last time interval, after washing and replacing the media, cell proliferation was measured using a commercial MTS solution (20 µL per well). The absorbance (at 490 nm and 630 nm) was measured by a Spectromax M2 plate reader (Molecular Devices). Each concentration treatment was done in quadruplets and the final numbers were averaged.

Results

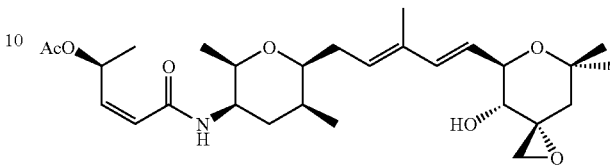

meayamycin

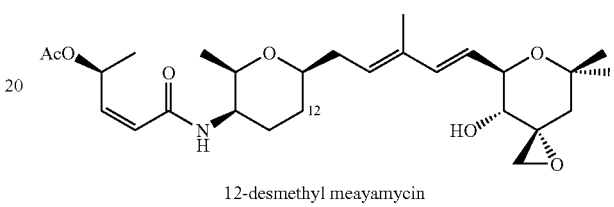

12-desmethyl meayamycin

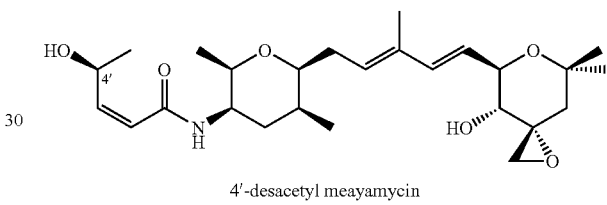

4'-desacetyl meayamycin

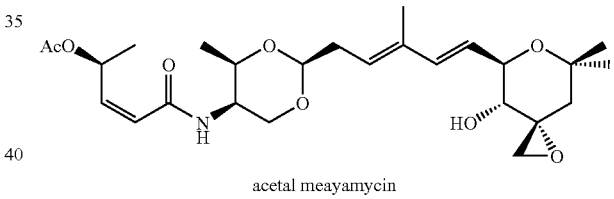

acetal meayamycin

The $GI_{50}$ values (in nM) of meayamycin and its analogs are summarized below.

|  | MCF-7 | A549 | DU145 | HCT116 | MDA-MB-231 | H1299 | PC-3 | HeLa |
|---|---|---|---|---|---|---|---|---|
| meayamycin | 0.010 | 0.11 | 0.47 | 0.044 | 0.024 | 0.091 | 0.058 | 0.24 |
| 12-desmethyl meayamycin | 0.30 | 1.0 | 3.5 | 2.2 | 0.70 | 2.8 | 1.6 |  |
| 4'-desacetyl meayamycin | 0.48 | 0.74 |  |  | 0.35 | 1.0 |  | 1.0 |
| acetal meayamycin | 2.5 |  |  |  |  |  |  |  |
| 3-OH-3-Me meayamycin |  |  |  |  |  |  |  |  |
| 3-OMe meayamycin |  |  |  |  |  |  |  |  |
| 3-OH meayamycin |  |  |  |  |  |  |  |  |

Example 56

Reversibility Experiments

All cells were treated at the same time meayamycin at 1 nM concentration. At the given time interval, the drug-containing media was removed and replaced with fresh media. Cell proliferation was measured at the last time interval (72 h).

Even the 4 hour treatment of A549 cells and MCF-7 cells showed nearly the same effect as the 72 hour treatment. These results indicate that meayamycin irreversibly inhibits the growth of A549 and MCF-7 cell lines. In other words, meayamycin may covalently binds to target biomacromolecules such as proteins. In contrast, our preliminary result using HeLa cells suggests that meayamycin reversibly inhibits the growth of HeLa cells, suggesting that meayamycin may not covalently bind to target biomacromolecules.

This comparison study shows that meayamycin inhibits the growth of A549 cells via the induction of apoptosis (apoptosis data not shown) while it does so only mildly against normal lung cells (IMR-90). Therefore, in lung, it is expected that meayamycin is specific for cancer.

Example 57

Synthesis and Biological Activity of Meayamycin B

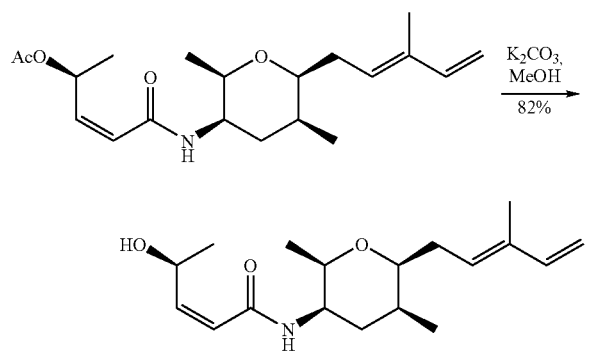

Preparation of (S,Z)-N-((2R,3R,5S,6S)-2,5-dimethyl-6-((E)-3-methylpenta-2,4-dienyl)-tetrahydro-2H-pyran-3-yl)-4-hydroxypent-2-enamide. To a stirred solution of (S,Z)-5-((2R,3R,5S,6S)-2,5-dimethyl-6-((E)-3-methylpenta-2,4-dienyl)-tetrahydro-2H-pyran-3-ylamino)-5-oxopent-3-en-2-yl acetate (26.5 mg, 0.0758 mmol) in MeOH (380 µL) was added $K_2CO_3$ (26.3 mg, 0.190 mmol) at 0° C. under an open atmosphere. After 2 h at the same temperature the reaction was diluted with saturated aqueous $NH_4Cl$ (60 µL) and stirred for 5 min. The resulting reaction mixture was dried over anhydrous $Na_2SO_4$, filtered, and concentrated under reduced pressure. The resulting residue was purified by flash chromatography (20→50% EtOAc in hexanes) on silica gel (3 mL) to give (S,Z)-N-((2R,3R,5S,6S)-2,5-dimethyl-6-((E)-3-methylpenta-2,4-dienyl)-tetrahydro-2H-pyran-3-yl)-4-hydroxypent-2-enamide (19.2 mg, 82%) as a colorless oil.

Data for (S,Z)-N-((2R,3R,5S,6S)-2,5-dimethyl-6-((E)-3-methylpenta-2,4-dienyl)-tetrahydro-2H-pyran-3-yl)-4-hydroxypent-2-enamide: $R_f$=0.21 (50% EtOAc in hexanes); IR (neat): 3325, 2975, 1655 (C=O), 1621, 1522, 1456, 1116, 1062, 894 cm$^{-1}$; $[\alpha]_D^{26}$ +10.0 (c 0.95, CHCl$_3$); $^1$H NMR (300 MHz, 293K, 1% CD$_3$OD in CDCl$_3$) δ 6.36 (dd, 1H, J=17.4, 10.8 Hz), 6.16 (dd, 1H, J=11.9, 5.6 Hz), 5.74 (dd, 1H, J=11.9, 1.3 Hz), 5.44 (br app t, 1H, J=8.1 Hz), 5.11 (d, 1H, J=17.4 Hz), 4.96 (d, 1H, J=10.8 Hz), 4.83-4.73 (m, 1H), 3.97-3.93 (m, 1H), 3.68 (qd, 1H, J=6.6, 2.1 Hz), 3.55 (qd, 1H, J=7.1, 2.5 Hz), 2.48-2.31 (m, 1H), 2.31-2.13 (m, 1H), 1.95-1.92 (m, 2H), 1.76 (br s, 3H), 1.34 (d, 3H, J=6.6 Hz), 1.14 (d, 3H, J=6.6 Hz), 1.01 (d, 3H, J=7.1 Hz); $^{13}$C NMR (125 MHz, 293K, CDCl$_3$) δ 166.1, 150.8, 141.2, 135.7, 127.9, 122.5, 111.2, 80.8, 75.8, 64.6, 47.5, 35.7, 31.8, 28.8, 22.7, 17.9, 15.2, 11.9; HRMS (EI+) calcd. for $C_{18}H_{29}NO_3$ (M)$^+$ 307.2147, found 307.2148.

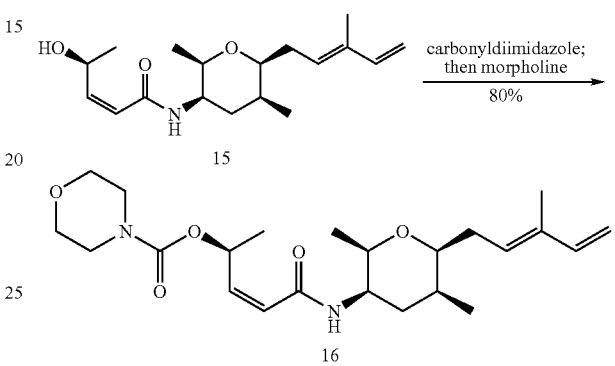

Preparation of (S,Z)-5-((2R,3R,5S,6S)-2,5-dimethyl-6-((E)-3-methylpenta-2,4-dienyl)-tetrahydro-2H-pyran-3-ylamino)-5-oxopent-3-en-2-yl morpholine-4-carboxylate. To a stirred solution of (S,Z)-N-((2R,3R,5S,6S)-2,5-dimethyl-6-((F)-3-methylpenta-2,4-dienyl)-tetrahydro-2H-pyran-3-yl)-4-hydroxypent-2-enamide (14.0 mg, 0.0445 mmol) in $CH_2Cl_2$ (0.5 mL) at 23° C. was added carbonyldiimidazole (11.2 mg, 0.0681 mmol) under an $N_2$ atmosphere. After 10 h, morpholine (15.8 mg, 0.182 mmol) was added and the mixture was stirred at 23° C. for 20 h. The solvent was removed and the resulting residue was purified by flash chromatography (10→60% EtOAc in hexanes) on silica gel (10 mL) to give (S,Z)-5-((2R,3R,5S,6S)-2,5-dimethyl-6-((E)-3-methylpenta-2,4-dienyl)-tetrahydro-2H-pyran-3-ylamino)-5-oxopent-3-en-2-yl morpholine-4-carboxylate (15.2 mg, 80%) as a colorless oil.

Data for (S,Z)-5-((2R,3R,5S,6S)-2,5-dimethyl-6-((E)-3-methylpenta-2,4-dienyl)-tetrahydro-2H-pyran-3-ylamino)-5-oxopent-3-en-2-yl morpholine-4-carboxylate: $R_f$=0.47 (80% EtOAc in hexanes); IR (neat): 3360, 2962, 2922, 2853, 1702 (C=O), 1669 (C=O), 1639, 1517, 1424, 1241, 1118, 1072 cm$^{-1}$; $[\alpha]_D^{26}$ −6.7 (c 0.60, $CH_2Cl_2$); $^1$H NMR (500 MHz, 293K, CD$_2$Cl$_2$) δ 6.37 (dd, 1H, J=17.5, 10.5 Hz), 6.17-6.12 (m, 2H), 5.91 (dd, 1H, J=11.5, 8.0 Hz), 5.70 (dd, 1H, J=11.5, 1.5 Hz), 5.50 (br app t, 1H, J=7.0 Hz), 5.11 (d, 1H, J=17.5 Hz), 4.94 (d, 1H, J=11.5 Hz), 3.92-3.89 (m, 1H), 3.66 (ddd, 1H, J=13.0, 6.5, 2.0 Hz), 3.61 (t, 4H, J=4.5 Hz), 3.54 (ddd, 1H, J=9.5, 7.0, 3.0 Hz), 3.42 (t, 4H, J=4.5 Hz), 2.39-2.33 (m, 1H), 2.25-2.19 (m, 1H), 1.95-1.92 (m, 2H), 1.79-1.76 (m, 1H), 1.75 (s, 3H), 1.35 (d, 3H, J=6.5 Hz), 1.12 (d, 3H, J=6.5 Hz), 1.03 (d, 3H, J=7.5 Hz); $^{13}$C NMR (125 MHz, 293K, CD$_2$Cl$_2$) δ 165.3, 155.4, 144.4, 141.9, 136.0, 129.4, 122.8, 111.2, 81.3, 76.4, 70.1, 67.1, 47.6, 36.4, 32.5, 30.3, 29.7, 20.6, 18.1, 15.4, 12.2; HRMS (ES+) calcd. for $C_{23}H_{36}N_2O_5$ (M+Na)$^+$ 443.2522, found 443.2496.

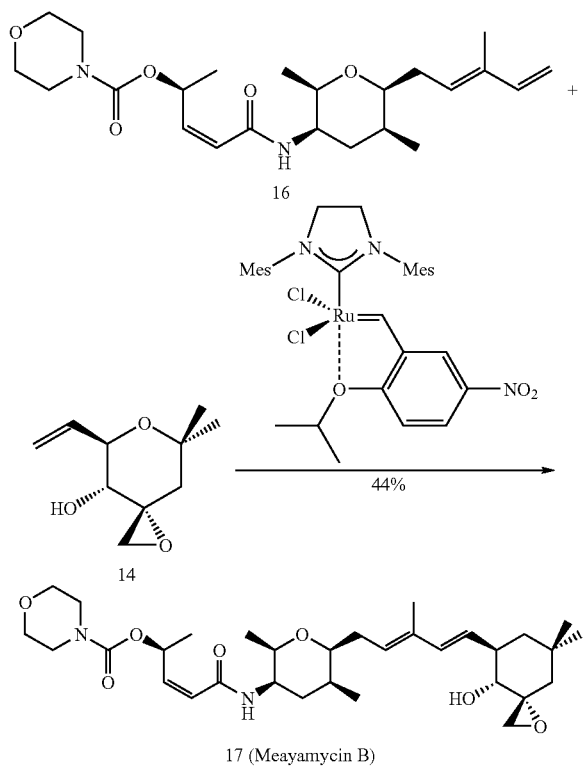

Preparation of (2Z,4S)-4-[(morpholinylcarbonyl)oxy]-N-[(2R,3R,5S,6S)-tetrahydro-6-[(2E,4E)-5-[(3R,4R,5R)-4-hydroxy-7,7-dimethyl-1,6-dioxaspiro[2.5]oct-5-yl]-3-methyl-2,4-pentadien-1-yl]-2,5-dimethyl-2H-pyran-3-yl]-2-pentenamide (Meayamycin B). A solution of (3R,4R,5R)-5-ethenyl-7,7-dimethyl-1,6-dioxaspiro[2.5]octan-4-ol (18 mg, 0.099 mmol) was prepared in ClCH$_2$CH$_2$Cl (200 µL) at 23° C. under an open atmosphere. To a stirred solution of (S,Z)-5-((2R,3R,5S,6S)-2,5-dimethyl-6-((E)-3-methylpenta-2,4-dienyl)-tetrahydro-2H-pyran-3-ylamino)-5-oxopent-3-en-2-yl morpholine-4-carboxylate (26 mg, 0.062 mmol) in ClCH$_2$CH$_2$Cl (200 µL) was added the solution of (3R,4R,5R)-5-ethenyl-7,7-dimethyl-1,6-dioxaspiro[2.5]octan-4-ol (100 µL), benzoquinone (1.4 mg, (0.012 mmol), followed by Grela catalyst (1.5 mg, 2.2 µmol) at 23° C. under an open atmosphere. The reaction mixture was then heated to 42° C. After 3 h at the same temperature, additional Grela catalyst (1.5 mg, 2.2 µmol) and (3R,4R,5R)-5-ethenyl-7,7-dimethyl-1,6-dioxaspiro[2.5]octan-4-ol (100 µL) were added. After 11 total hours, the reaction was concentrated under reduced pressure. The resulting residue was purified by flash chromatography (10→80% EtOAc in hexanes) on silica gel (8 mL) to give (2Z,4S)-4-[(morpholinylcarbonyl)oxy]-N-[(2R,3R,5S,6S)-tetrahydro-6-[(2E,4E)-5-[(3R,4R,5R)-4-hydroxy-7,7-dimethyl-1,6-dioxaspiro[2.5]oct-5-yl]-3-methyl-2,4-pentadien-1-yl]-2,5-dimethyl-2H-pyran-3-yl]-2-Pentenamide (10.4 mg, 29%), and a mixture of (S,Z)-5-((2R,3R,5S,6S)-2,5-dimethyl-6-((E)-3-methylpenta-2,4-dienyl)-tetrahydro-2H-pyran-3-ylamino)-5-oxopent-3-en-2-yl morpholine-4-carboxylate and (3R,4R,5R)-5-ethenyl-7,7-dimethyl-1,6-dioxaspiro[2.5]octan-4-ol (22.1 mg).

To a stirred solution of recovered (S,Z)-5-((2R,3R,5S,6S)-2,5-dimethyl-6-((E)-3-methylpenta-2,4-dienyl)-tetrahydro-2H-pyran-3-ylamino)-5-oxopent-3-en-2-yl morpholine-4-carboxylate and (3R,4R,5R)-5-ethenyl-7,7-dimethyl-1,6-dioxaspiro[2.5]octan-4-ol (22.1 mg) in ClCH$_2$CH$_2$Cl (200 µL) was added benzoquinone (1.0 mg, 0.010 mmol) and Grela Catalyst (2.0 mg, 3.0 µmol) at 23° C. under an open atmosphere. The reaction mixture was then heated to 42° C. After an additional 14 h at the same temperature, the reaction was concentrated under reduced pressure. The resulting residue was purified by flash chromatography (10→80% EtOAc in hexanes) on silica gel (8 mL) to give (2Z,4S)-4-[(morpholinylcarbonyl)oxy]-N-[(2R,3R,5S,6S)-tetrahydro-6-[(2E,4E)-5-[(3R,4R,5R)-4-hydroxy-7,7-dimethyl-1,6-dioxaspiro[2.5]oct-5-yl]-3-methyl-2,4-pentadien-1-yl]-2,5-dimethyl-2H-pyran-3-yl]-2-pentenamide as a pale tan solid. The combined yield of (2Z,4S)-4-[(morpholinylcarbonyl)oxy]-N-[(2R,3R,5S,6S)-tetrahydro-6-[(2E,4E)-5-[(3R,4R,5R)-4-hydroxy-7,7-dimethyl-1,6-dioxaspiro[2.5]oct-5-yl]-3-methyl-2,4-pentadien-1-yl]-2,5-dimethyl-2H-pyran-3-yl]-2-pentenamide after one cycle is 15.7 mg (44%). Some of the tan (2Z,4S)-4-[(morpholinylcarbonyl)oxy]-N-[(2R,3R,5S,6S)-tetrahydro-6-[(2E,4E)-5-[(3R,4R,5R)-4-hydroxy-7,7-dimethyl-1,6-dioxaspiro[2.5]oct-5-yl]-3-methyl-2,4-pentadien-1-yl]-2,5-dimethyl-2H-pyran-3-yl]-2-pentenamide was purified by semi-preparative HPLC (Conditions: flow rate=2.5 mL, from 30% to 100% MeCN in H$_2$O over 30 min; Column=Varian Pursuit XRs C18 column (5 µm packing, 250×10 mm); Retention time 16.70 min; Detection=237 nm) to afford (2Z,4S)-4-[(morpholinylcarbonyl)oxy]-N-[(2R,3R,5S,6S)-tetrahydro-6-[(2E,4E)-5-[(3R,4R,5R)-4-hydroxy-7,7-dimethyl-1,6-dioxaspiro[2.5]oct-5-yl]-3-methyl-2,4-pentadien-1-yl]-2,5-dimethyl-2H-pyran-3-yl]-2-pentenamide as a colorless oil that was subsequently used for biological experiments.

Data for (2Z,4S)-4-[(morpholinylcarbonyl)oxy]-N-[(2R,3R,5S,6S) -tetrahydro-6-[(2E,4E)-5-[(3R,4R,5R)-4-hydroxy-7,7-dimethyl-1,6-dioxaspiro[2.5]oct-5-yl]-3-methyl-2,4-pentadien-1-yl]-2,5-dimethyl-2H-pyran-3-yl]-2-pentenamide: R$_f$=0.24 (80% EtOAc in hexanes); IR (neat): 3366, 2971, 2925, 2856, 1700, 1670, 1640, 1516, 1425, 1242, 1116, 1058 cm$^{-1}$; $[\alpha]_D^{26}$ +27.2 (c 0.32, CH$_2$Cl$_2$); $^1$H NMR (500 MHz, 293K, CD$_2$Cl$_2$) δ 6.36 (d, 1H, J=15.5 Hz), 6.17-6.12 (m, 2H), 5.92 (dd, 1H, J=11.5, 8.0 Hz), 5.70 (dd, 1H, J=11.5, 1.0 Hz), 5.64 (dd, 1H, J=15.5, 6.5 Hz), 5.52 (br app t, 1H, J=7.0 Hz), 3.97 (dd, 1H, J=9.0, 6.5 Hz), 3.91-3.90 (m, 1H), 3.66 (ddd, J=13.0, 6.5, 2.0 Hz), 3.61 (t, 4H, J=4.5 Hz), 3.55-3.51 (m, 1H), 3.48 (t, 1H, J=10.0 Hz), 3.42 (t, 4H, J=4.5 Hz), 2.96 (d, 1H, J=4.5 Hz), 2.46 (d, 1H, J=4.5 Hz), 2.39-2.33 (m, 1H), 2.24-2.20 (m, 1H), 2.15 (dd, 1H, J=16.0, 14.0 Hz), 1.94-1.92 (m, 2H), 1.78 (s, 3H), 1.64-1.60 (m, 4H), 1.36 (s, 3H), 1.35 (d, 3H, J=7.0 Hz), 1.23 (s, 3H), 1.12 (d, 3H, J=6.5 Hz), 1.03 (d, 3H, J=7.5 Hz); $^{13}$C NMR (125 MHz, 293K, CD$_2$Cl$_2$) δ 165.3, 155.4, 144.4, 137.9, 135.1, 129.7, 126.0, 122.8, 81.4, 76.4, 75.1, 73.2, 70.1, 68.8, 67.1, 58.0, 48.0, 47.6, 43.2, 36.4, 32.6, 31.3, 30.2, 29.8, 23.9, 20.6, 18.1, 15.4, 12.9; HRMS (ES+) calcd. for C$_{31}$H$_{48}$N$_2$O$_8$ (M+Na)$^+$ 599.3308, found 599.3271.

The GI$_{50}$ of meayamycin B against MCF-7 was approximately 20 pM and that of meayamycin was 40 pM in the 5-day assay. The half-life of meayamycin B in murine serum is 13 hours whereas that of meayamycin is 2 hours. Therefore, although meayamycin B is only 2 times more potent than meayamycin in cultured cells, these data are suggestive of meayamycin B exhibiting better pharmacokinetics.

Example 58

High-Content Analysis

High-content analysis (HCA) is an analysis tool designed to yield information about the activity and spatial regulation of multiple targets in individual cells rather than in a cell population as a whole (Giuliano, K. A., DeBiasio, R. L., Dunlay, T., Gough, A., Volosky, J. M., Zock, J., Pavlakis, G. N., and Taylor, D. L. (1997). High-Content Screening: A new aproach to easing key bottlenecks in the drug discovery process. J. Biomol. Screen. 2, 249-259.; Taylor, D. L., Woo, E. S., and Giuliano, K. A. (2001). Real-time molecular and cellular analysis: the new frontier of drug discovery. Curr. Opin. Biotechnol. 12, 75-81.). HCA encompasses the automated acquisition, analysis, and archiving of fluorescence micrographs of monolayer cell populations with fluorescently labeled cellular constituents of interest. The multiparametric, automated nature of HCA enables the simultaneous, rapid and quantitative analysis of many cellular phenotypes. HCA has proven exeptionally valuable in cases where compound supply is limited (Wipf, P., Graham, T. H., Vogt, A., Sikorski, R. P., Ducruet, A. P., and Lazo, J. S. (2006). Cellular analysis of disorazole Cl and structure-activity relationship of analogs of the natural product. Chem. Biol. Drug Des. 67, 66-73).

High-content analysis of mitotic arrest by meayamycin and FR 901464. It had previously been shown that FR 901464 caused cell cycle arrest in both G1 and G2 (Kaida, D., Motoyoshi, H., Tashiro, E., Nojima, T., Hagiwara, M., Ishigami, K., Watanabe, H., Kitahara, T., Yoshida, T., Nakajima, H., Tani, T., Horinouchi, S., and Yoshida,M. (2007). Spliceostatin A targets SF3b and inhibits both splicing and nuclear retention of pre-mRNA. Nat. Chem. Biol. 3, 576-583). A multiparameter high-content analysis investigated the effects of meayamycin and FR 901464 on G2/M arrest and cellular microtubule perturbation as previously described (Wipf et al., 2006; Wang, Z., McPherson, P. A., Raccor, B. S., Balachandran, R., Zhu, G., Day, B. W., Vogt, A., and WipfP. (2007). Structure-activity and High-content Imaging Analyses of Novel Tubulysins. Chem. Biol. Drug Des 70, 75-86).

Thus, asynchronously growing HeLa cells were treated for 21 h with each compound in collagen-coated 384 well microplates, fixed, and incubated with primary antibodies against alpha-tubulin and the mitotic marker protein phospho-histone H3, followed by FITC and Cy3-conjugated secondary antibodies, respectively. Nuclei were detected by counterstaining with Hoechst 33342. The quantitative assessment of MT perturbation and mitotic arrest by meayamycin were compared with FR 901464 and two standard mitotic arresters, paclitaxel and vincristine. While both standard agents caused mitotic arrest, chromatin condensation, and changes in microtubule morphology, neither FR 901464 nor meayamycin were mitotic arresters.

Antiproliferative activity in multidrug resistant cells. This examples investigated the growth inhibitory activities of FR901464 and meayamycin in DC3F transformed Chinese hamster cells and the multidrug resistant subline VCRd5L (Peterson, R. H., Meyers, M. B., Spengler, B. A., and Biedler, J. L. (1983) Alteration of plasma membrane glycopeptides and gangliosides of Chinese hamster cells accompanying development of resistance to daunorubicin and vincristine. Cancer Res. 43, 222-228) using previously described methodology (Vogt, A., Kalb, E. N., and Lazo, J. S. (2004) A scalable high-content cytotoxicity assay insensitive to changes in mitochondrial metabolic activity. Oncol. Res. 14, 305-314). These cells are cross-resistant to a number of chemotherapeutic agents, including vincristine, paclitaxel, and actinomycin D and owe their resistance to expression of various membrane glycoproteins (p-gp) (Scotto, K. W., Biedler, J. L., and Melera, P. W. (1986). Amplification and expression of genes associated with multidrug resistance in mammalian cells. Science 232, 751-755).

The VCRd-5L cells were >250-fold resistant to vincristine and 60-fold resistant to paclitaxel. FR 901464 and meayamycin potently inhibited the growth of the parental DC3F cells (Table 2), with meayamycin being active in the subnanomolar range. While FR 901464 was about an order of magnitude less active in the multidrug resistant cells, meayamycin retained picomolar activity, suggesting that it is not a substrate for p-gp (Table 2).

TABLE 2

Antiproliferative activity of FR901464 and meayamycin in cultured cell lines [a]

| | DC3F (pm) | VCRd5L (pm) | fold resistance (pm) |
|---|---|---|---|
| FR901464 | 7.49 ± 1.26 (4) | >100 (4) | 13.5 |
| meayamycin | 0.46 ± 0.09 (4) | 0.71 ± 0.27 (4) | 1.5 |
| vincristine | 18.8 ± 16.2 (10) | >>5000 (6) | >>265 |
| paclitaxel | 45.4 ± 11.3 (8) | 2682 ± 109 (4) | 60 |

[a] average GI50 values ± SD (n)

Selectivity of meayamycin toward cancer cells. The ability to selectively affect transformed but not normal cells is a desired attribute for any antineoplastic agent. The effects of meayamycin in normal lung (IMR-90) were compared to thosein A-549 lung cancer cells. IMR-90 human lung fibroblasts were chosen because they are a well characterized normal cell line that is resistant to a variety of cytotoxic and antisignaling agents (Erickson, L. C., Bradley, M. O., Ducore, J. M., Ewig, R. A., and Kohn, K. W. (1980). DNA crosslinking and cytotoxicity in normal and transformed human cells treated with antitumor nitrosoureas. Proc. Natl. Acad. Sci. U.S.A 77, 467-471., Dusre, L., Covey, J. M., Collins, C., and Sinha, B. K. (1989). DNA damage, cytotoxicity and free radical formation by mitomycin C in human cells. Chem. Biol. Interact. 71, 63-78.; Hsieh, T. J., Liu, T. Z., Chem, C. L., Tsao, D. A., Lu, F. J., Syu, Y. H., Hsieh, P. Y., Hu, H. S., Chang, T. T., and Chen, C. H. (2005). Liriodenine inhibits the proliferation of human hepatoma cell lines by blocking cell cycle progression and nitric oxide-mediated activation of p53 expression. Food Chem. Toxicol. 43, 1117-1126.; Suzuki, H., Aoshiba, K., Yokohori, N., and Nagai, A. (2003). Epidermal growth factor receptor tyrosine kinase inhibition augments a murine model of pulmonary fibrosis. Cancer Res. 63, 5054-5059.). The cells have a finite lifespan of approximately 60 population doublings (Nichols, W. W., Murphy, D. G., Cristofalo, V. J., Toji, L. H., Greene, A. E., and Dwight, S. A. (1977). Characterization of a new human diploid cell strain, IMR-90. Science 196, 60-63) before entering crisis, which was confirmed. Cells were plated at high density (10,000 per well) in 384 well plates and treated for 24 h with vehicle (DMSO) or ten two-fold concentration gradients of meayamycin. At the end of the study, cells were fixed and immunostained with antibodies against p53 and the cleaved form of caspase-3. Nuclei were counterstained with Hoechst 33342 and enumerated.

Twenty-four (24) hours after treatment, meayamycin (10 nM) consistently caused a more pronounced cell loss in the A-549 lung cancer cells compared with normal cells. Both cell lines responded to meayamycin with p53 induction, although the magnitude of response was smaller in the normal cells. A low level of caspase cleavage that appeared to be selective for A-549 cells was observed in some experiments. Meayamycin did not cause nuclear fragmentation but instead enlarged nuclei. Thus, meayamycin preferentially affects the survival of lung cancer cells compared with normal lung fibroblasts.

We claim:

1. A compound, stereoisomer, or pharmaceutically acceptable salt or ester thereof having Formula I:

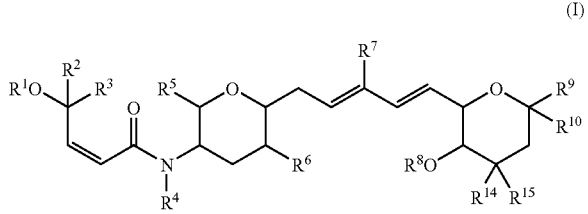

(I)

wherein
$R^1$ and $R^8$ are independently selected from the group consisting of H, $C_{1-6}$-alkyl, halo($C_{1-6}$-alkyl), C(O)$R^{11}$, C(O)O$R^{11}$, and C(O)N$R^{12}R^{13}$,
wherein each $R^{11}$ is independently H, $C_{1-6}$-alkyl, or halo($C_{1-6}$-alkyl), and
wherein $R^{12}$ and $R^{13}$ are selected independently from the group consisting of H, $C_{1-6}$-alkyl, and halo($C_{1-6}$-alkyl);
or $R^{12}$ and $R^{13}$, together with the nitrogen atom to which they are bound, form a heterocyclic or heterocyclic ring;
$R^2$, $R^3$, $R^4$, $R^5$, and $R^6$ are independently selected from the group consisting of H, $C_{1-6}$-alkyl, and halo($C_{1-6}$-alkyl);
$R^7$ is selected from the group consisting of H, $C_{1-6}$-alkyl and halo($C_{1-6}$-alkyl); and
$R^9$ and $R^{10}$ are independently selected from the group consisting of H, OH, $C_{1-6}$-alkyl, and $C_{1-6}$-alkyl substituted with one to three groups independently selected from halo, hydroxy, and $C_{1-6}$-alkoxy;
$R^{14}$ and $R^{15}$ are selected independently from the group consisting of halo($C_{1-6}$-alkyl), C(O)$R^{11}$, F, Cl, $NO_2$, and B(O$R^{11})_2$, wherein $R^{11}$ is as defined above;
or $R^{14}$ and $R^{15}$, together with the carbon atom to which they are bound, form an epoxide ring;
provided that when $R^1$ is C(O)$CH_3$, $R^2$, $R^4$, and $R^8$ are hydrogen, and $R^3$, $R^5$, $R^6$, $R^7$, and $R^9$ are methyl, then $R^{10}$ is not hydrogen or OH.

2. The compound according to claim 1 having Formula Ib:

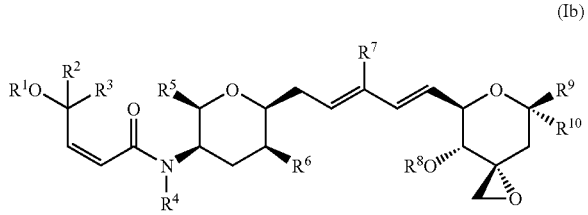

(Ib)

wherein $R^1$, $R^2$, $R^3$, $R^4$, $R^5$, $R^6$, $R^7$, $R^8$, $R^9$, and $R^{10}$ are as defined in claim 1.

3. The compound according to claim 2 wherein $R^1$ is C(O)$R^{11}$ and $R^{11}$ is $C_{1-6}$-alkyl or halo($C_{1-6}$-alkyl).

4. The compound according to claim 3 wherein $R^1$ is C(O)$CH_3$.

5. The compound according to claim 2 wherein at least one of $R^2$, $R^3$, $R^5$, and $R^6$ is $C_{1-6}$-alkyl.

6. The compound according to claim 5 wherein at least one of $R^2$, $R^3$, $R^5$, and $R^6$ is $CH_3$.

7. The compound according to claim 2 wherein $R^4$ is hydrogen.

8. The compound according to claim 2 wherein $R^7$ is $CH_3$ or $CF_3$.

9. The compound according to claim 2 wherein at least one of $R^9$ and $R^{10}$ is independently selected from the group consisting of $C_{1-6}$-alkyl and $C_{1-6}$-alkyl substituted with one to three groups independently selected from halo, hydroxy, and $C_{1-6}$-alkoxy.

10. The compound according to claim 9 wherein at least one of $R^9$ and $R^{10}$ is independently selected from the group consisting of $CH_3$, $CH_2I$, and $CH_2OH$.

11. The compound according to claim 1 having Formula (Ic):

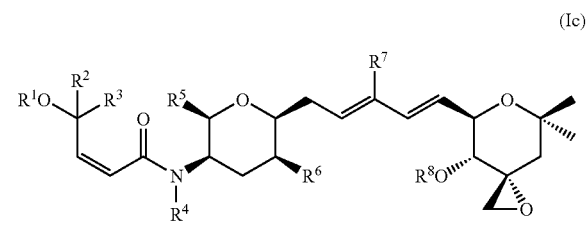

(Ic)

wherein $R^1$, $R^2$, $R^3$, $R^4$, $R^5$, $R^6$, $R^7$, and $R^8$ are as defined in claim 1.

12. The compound according to claim 11 wherein $R^1$ is C(O)$R^{11}$ and $R^{11}$ is $C_{1-6}$-alkyl or halo($C_{1-6}$-alkyl).

13. The compound according to claim 12 wherein $R^1$ is C(O)$CH_3$.

14. The compound according to claim 11 wherein at least one of $R^2$, $R^3$, $R^5$, and $R^6$ is $C_{1-6}$-alkyl.

15. The compound according to claim 14 wherein at least one of $R^2$, $R^3$, $R^5$, and $R^6$ is $CH_3$.

16. The compound according to claim 11 wherein $R^4$ is hydrogen.

17. The compound according to claim 11 wherein $R^7$ is $CH_3$ or $CF_3$.

18. The compound according to claim 1 that is selected from the group consisting of:

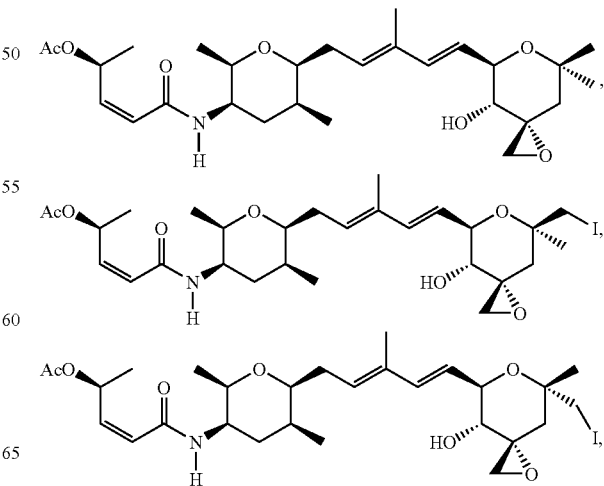

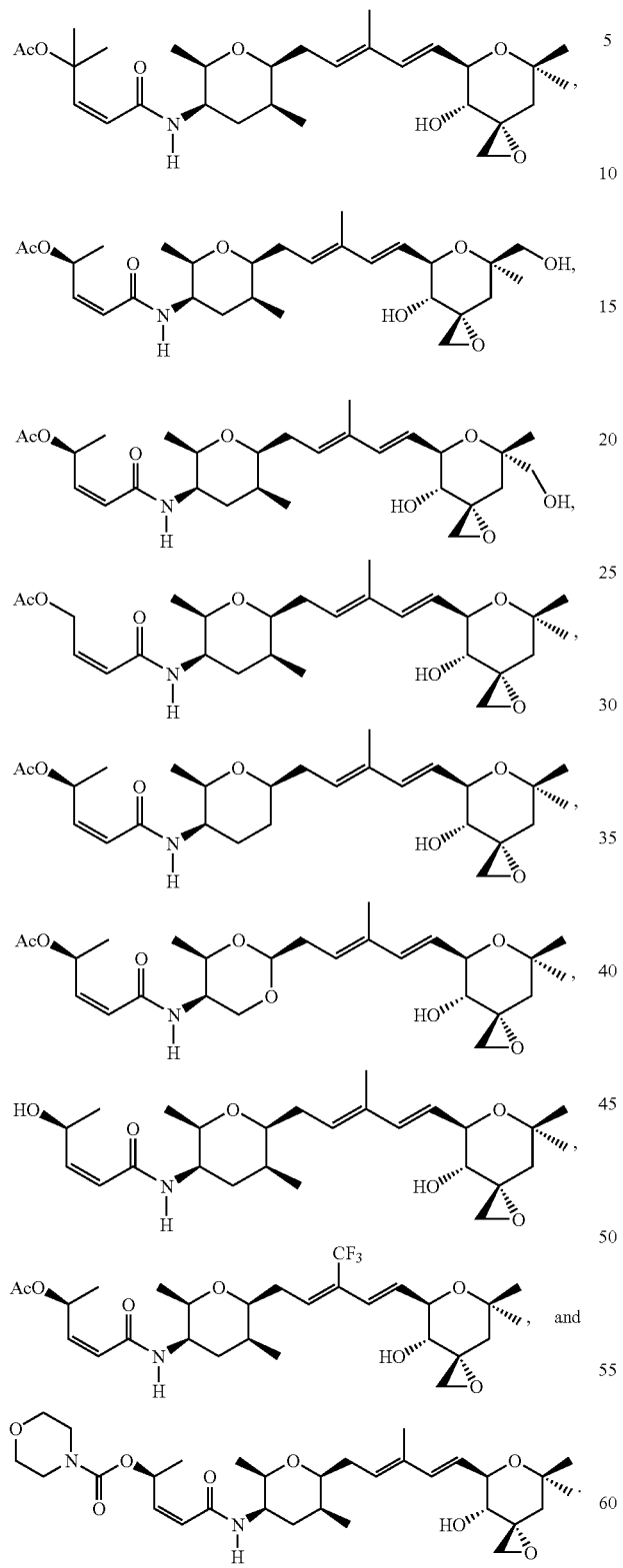

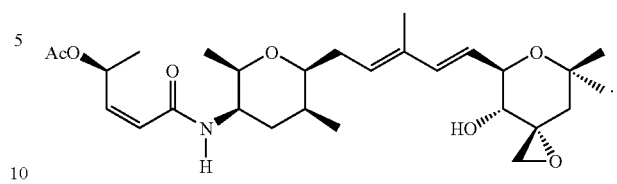

20. A pharmaceutical composition comprising a compound according to claim 1, a stereoisomer, or pharmaceutically acceptable salt or ester thereof and a pharmaceutically acceptable carrier.

21. The composition according to claim 20 comprising a compound or pharmaceutically acceptable salt or ester thereof of Formula (IX):

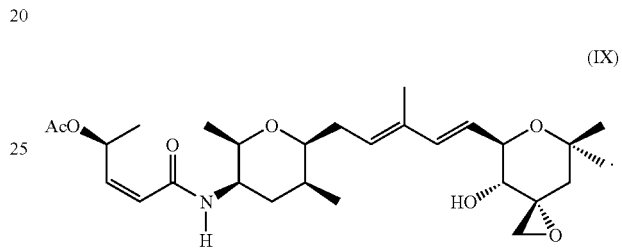

22. A process for preparing a compound, stereoisomer, or pharmaceutically acceptable salt or ester thereof having Formula I:

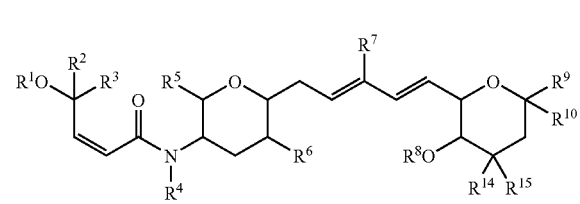

wherein
- $R^1$ and $R^8$ are independently selected from the group consisting of H, Pg, $C_{1-6}$-alkyl, halo($C_{1-6}$-alkyl), $C(O)R^{11}$, $C(O)OR^{11}$, and $C(O)NR^{12}R^{13}$,
  - wherein each $R^{11}$ is independently H, $C_{1-6}$-alkyl, or halo($C_{1-6}$-alkyl), and
  - wherein $R^{12}$ and $R^{13}$ are selected independently from the group consisting of H, $C_{1-6}$-alkyl, and halo($C_{1-6}$-alkyl);
  - or $R^{12}$ and $R^{13}$, together with the nitrogen atom to which they are bound, form a 5- to 6-membered heterocyclic or heteroaromatic ring;
- $R^2$, $R^3$, $R^4$, $R^5$, and $R^6$ are independently selected from the group consisting of H, $C_{1-6}$-alkyl, and halo($C_{1-6}$-alkyl);
- $R^7$ is selected from the group consisting of H, $C_{1-6}$-alkyl and halo($C_{1-6}$-alkyl); and
- $R^9$ and $R^{10}$ are independently selected from the group consisting of H, OH, $C_{1-6}$-alkyl, and $C_{1-6}$-alkyl substituted with one to three groups independently selected from halo, hydroxy, $C_{1-6}$-alkoxy, and OPg;

19. The compound according to claim 18 or a stereoisomer or pharmaceutically acceptable salt or ester thereof of Formula (IX):

$R^{14}$ and $R^{15}$ are selected independently from the group consisting of halo($C_{1-6}$-alkyl), $C(O)R^{11}$, F, Cl, $NO_2$, and $B(OR^{11})_2$, wherein $R^{11}$ is as defined above;

or $R^{14}$ and $R^{15}$, together with the carbon atom to which they are bound, form an epoxide ring; and each Pg is independently a hydroxy protecting group;

said method comprising contacting a compound of Formula (II) wherein E, $R^1$, $R^2$, $R^3$, $R^4$, $R^5$, $R^6$, and $R^7$ are as defined above:

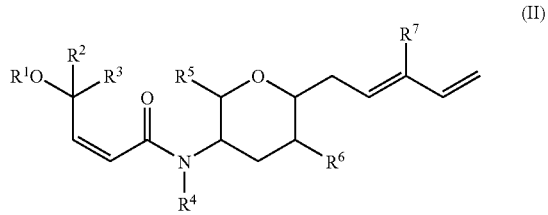

(II)

with a compound of Formula (III) wherein $R^8$, $R^9$, $R^{10}$, $R^{14}$, and $R^{15}$ are as defined above:

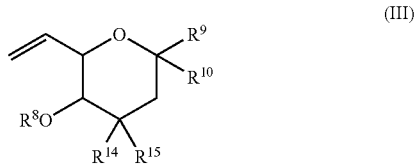

(III)

in the presence of an olefin metathesis catalyst to provide a compound of Formula I provided that when $R^1$ is $C(O)CH_3$; $R^2$, $R^4$, and $R^8$ are hydrogen; $R^3$, $R^5$, $R^6$, $R^7$, and $R^9$ are methyl; and $R^{10}$ is OH, then the compound of Formula (III) is a compound of Formula (IIIa):

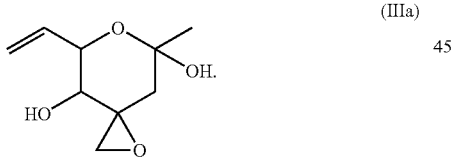

(IIIa)

23. The process according to claim 22, wherein the compound of Formula I is compound (IX):

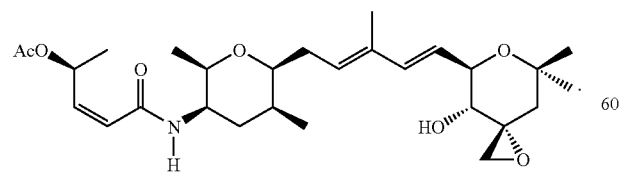

(IX)

24. A process for preparing compound, stereoisomer, or pharmaceutically acceptable salt or ester thereof having Formula I:

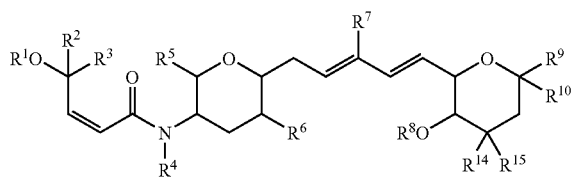

I wherein $R^1$ and $R^8$ are independently selected from the group consisting of H, Pg, $C_{1-6}$-alkyl, halo($C_{1-6}$-alkyl), $C(O)R^{11}$, $C(O)OR^{11}$, and $C(O)NR^{12}R^{13}$, wherein each $R^{11}$ is independently H, $C_{1-6}$-alkyl, or halo($C_{1-6}$-alkyl), and wherein $R^{12}$ and $R^{13}$ are selected independently from the group consisting of H, $C_{1-6}$-alkyl, and halo($C_{1-6}$-alkyl);

or $R^{12}$ and $R^{13}$, together with the nitrogen atom to which they are bound, form a 5- to 6-membered heterocyclic or heteroaromatic ring;

$R^2$, $R^3$, $R^4$, $R^5$, and $R^6$ are independently selected from the group consisting of H, $C_{1-6}$-alkyl, and halo($C_{1-6}$-alkyl);

$R^7$ is selected from the group consisting of H, $C_{1-6}$-alkyl and halo($C_{1-6}$-alkyl); and $R^9$ and $R^{10}$ are independently selected from the group consisting of H, OH, $C_{1-6}$-alkyl, and $C_{1-6}$-alkyl substituted with one to three groups independently selected from halo, hydroxy, $C_{1-6}$-alkoxy, and OPg;

$R^{14}$ and $R^{15}$ are selected independently from the group consisting of halo($C_{1-6}$-alkyl), $C(O)R^{11}$, F, Cl, $NO_2$, and $B(OR^{11})_2$, wherein $R^{11}$ is as defined above;

or $R^{14}$ and $R^{15}$, together with the carbon atom to which they are bound, form an epoxide ring;

said process comprising:

(a) contacting a compound of Formula (IVc), wherein $R^9$, $R^{14}$, and $R^{15}$ are as defined above and $P^1$ is a hydroxy protecting group, with an oxidizing agent to form a first compound of Formula (V) wherein $R^9$, $R^{14}$, and $R^{15}$ are as defined above, $P^1$ is a hydroxy protecting group, and $P^2$ is hydrogen:

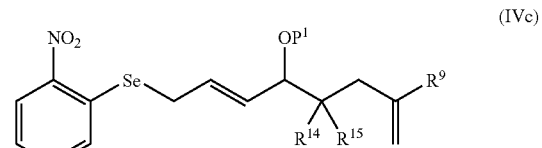

(IVc)

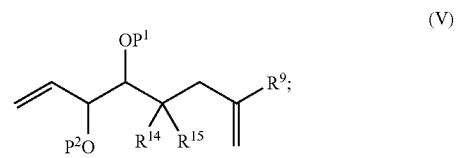

(V)

(b) converting said first compound of Formula (V) wherein $P^1$ is a hydroxy protecting group and $P^2$ is hydrogen to a second compound of Formula (V) wherein $P^1$ and $P^2$ are hydroxy protecting groups;

(c) optionally converting said first or second compound of Formula (V) under cyclization conditions to a compound of Formula (III) wherein $R^8$, $R^9$, and $R^{10}$ are as defined herein:

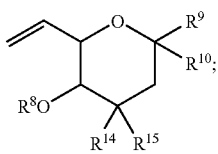

(III)

or (d) optionally converting said second compound of Formula (V) under oxidative conditions to a compound of Formula (VI) wherein $R^9$, $R^{14}$, and $R^{15}$ are as defined above, and $P^1$ and $P^2$ are hydroxy protecting groups; and converting the compound of Formula (VI) under cyclization conditions to a compound of Formula (III):

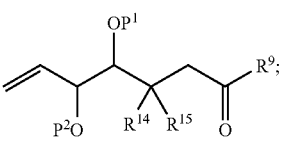

(VI)

(e) contacting a compound of Formula (III) with a compound of Formula (II) wherein $R^1$, $R^2$, $R^3$, $R^4$, $R^5$, $R^6$, and $R^7$ are as defined herein:

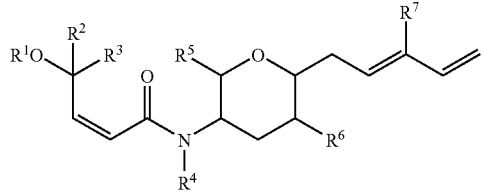

(II)

in the presence of an olefin metathesis catalyst to form a compound of Formula I.

25. The process according to claim 24, said process further comprising:

(a) contacting a compound of Formula (VII) with Ag—CC—CO$_2$Me and Cp$_2$ZrCl$_2$ to form a compound of Formula (VIII) wherein $R^9$, $R^{14}$, and $R^{15}$ are as defined in claim 24:

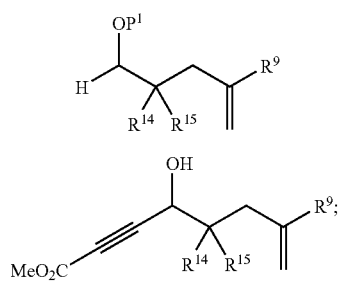

(VII)

(VIII)

(b) contacting a compound of Formula (VIII) with Red-Al to form a compound of Formula (IVa) wherein $P^1$ is hydrogen:

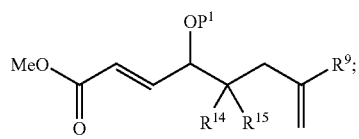

(IVa)

(c) converting a compound of Formula (IVa) wherein $P^1$ is hydrogen to a compound of Formula (IVa) wherein $P^1$ is a hydrogen protecting group;

(d) contacting a compound of Formula (IVa) wherein $P^1$ is a hydrogen protecting group with a reducing agent to form a compound of Formula (IVb) wherein $P^1$ is a hydrogen protecting group

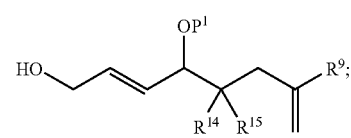

(IVb)

(e) reacting a compound of Formula (IVb) wherein $P^1$ is a hydrogen protecting group with o-O$_2$N-PhSeCN under selenide forming conditions to a compound of Formula (IVc:

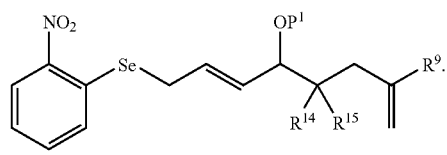

(IVc)

26. The process according to claim 24, wherein the compound of Formula I is compound (X):

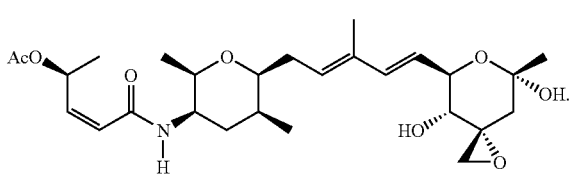

(X)

27. The process according to claim 24, wherein the compound of Formula I is compound (IX):

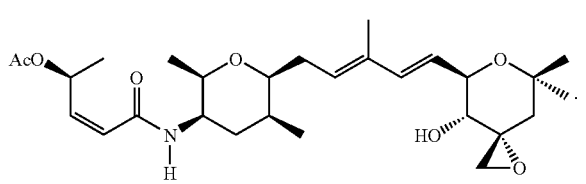

(IX)

28. An intermediate compound having Formula (IV):

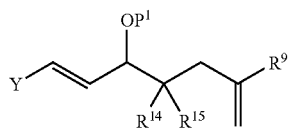

wherein
Y is selected from the group consisting of MeO$_2$C—, o-O$_2$N-PhSeCH$_2$—, and HOCH$_2$—;
R$^9$ is selected from the group consisting of C$_{1-6}$-alkyl and C$_{1-6}$-alkyl substituted with one to three groups independently selected from halo, hydroxy, C$_{1-6}$-alkoxy, and OPg;
R$^{14}$ and R$^{15}$ are selected independently from the group consisting of halo(C$_{1-6}$-alkyl), C(O)R$^{11}$, F, Cl, NO$_2$, and B(OR$^{11}$)$_2$, wherein each R$^{11}$ is independently H, C$_{1-6}$-alkyl, or halo(C$_{1-6}$-alkyl),
or R$^{14}$ and R$^{15}$, together with the carbon atom to which they are bound, form an epoxide ring; and
P$^1$ and Pg are independently a hydroxy protecting group.

29. The intermediate compound according to claim 28 wherein P$^1$ is triethylsilyl and R$^9$ is C$_{1-6}$-alkyl.

30. The intermediate compound according to claim 29 that is selected from the group consisting of:

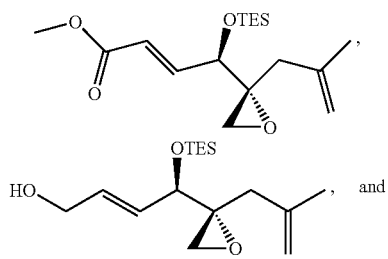

and

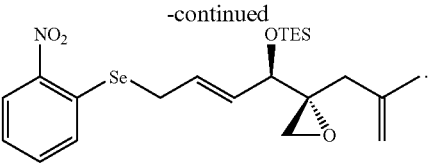

31. The composition according to claim 20 comprising a compound or pharmaceutically acceptable salt of ester thereof of:

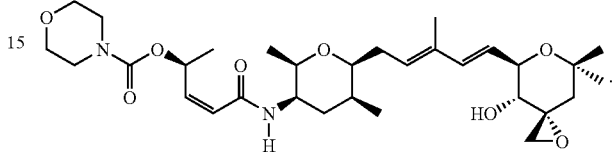

32. The process according to claim 22, wherein the compound of Formula I is

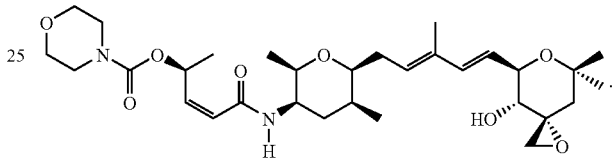

33. The process according to claim 24, wherein the compound of Formula I is

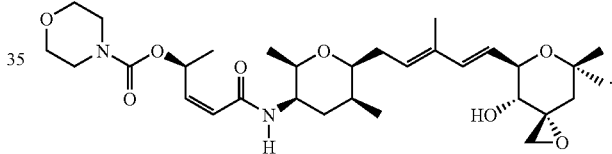

* * * * *